US008207262B2

(12) United States Patent
Calabro et al.

(10) Patent No.: US 8,207,262 B2
(45) Date of Patent: *Jun. 26, 2012

(54) HYDROXYPHENYL CROSS-LINKED MACROMOLECULAR NETWORK AND APPLICATIONS THEREOF

(75) Inventors: Anthony Calabro, Cleveland Heights, OH (US); Lee Akst, Boston, MA (US); Daniel Alam, Shaker Heights, OH (US); James Chan, Cleveland Heights, OH (US); Aniq B. Darr, Parma Heights, OH (US); Kiyotaka Fukamachi, Mayfield Heights, OH (US); Richard A. Gross, Plainview, NY (US); David Haynes, Waco, TX (US); Keiji Kamohara, Mayfield Heights, OH (US); Daniel P. Knott, Shaker Heights, OH (US); Hilel Lewis, Beachwood, OH (US); Alex Melamud, Durham, NC (US); Anthony Miniaci, Chagrin Falls, OH (US); Marshall Strome, Gates Mills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 726 days.

This patent is subject to a terminal disclaimer.

(21) Appl. No.: 12/283,661

(22) Filed: Sep. 15, 2008

(65) Prior Publication Data

US 2009/0042294 A1 Feb. 12, 2009

Related U.S. Application Data

(63) Continuation of application No. 11/176,544, filed on Jul. 7, 2005, now Pat. No. 7,465,766, which is a continuation-in-part of application No. 10/753,779, filed on Jan. 8, 2004, now Pat. No. 6,982,298.

(60) Provisional application No. 60/586,585, filed on Jul. 9, 2004, provisional application No. 60/439,201, filed on Jan. 10, 2003.

(51) Int. Cl.
*C08G 63/91* (2006.01)
*C08G 63/48* (2006.01)

(52) U.S. Cl. ............ 525/54.1; 525/54.2; 525/326.1; 525/420; 527/600

(58) Field of Classification Search ................ 525/54.1, 525/54.2, 326.1, 420, 540; 527/600
See application file for complete search history.

(56) References Cited

U.S. PATENT DOCUMENTS

| 4,024,073 A | 5/1977 | Shimizu et al. |
|---|---|---|
| 4,256,596 A | 3/1981 | Cohen |
| 4,277,582 A | 7/1981 | Mueller et al. |
| 4,350,629 A | 9/1982 | Yannas et al. |
| 4,500,676 A | 2/1985 | Balazs et al. |
| 5,017,229 A | 5/1991 | Burns et al. |
| 5,128,326 A | 7/1992 | Balazs et al. |
| 5,532,221 A | 7/1996 | Huang et al. |
| 5,667,778 A | 9/1997 | Atala |
| 5,705,488 A | 1/1998 | Janzen et al. |
| 5,739,113 A | 4/1998 | Lee |
| 5,769,899 A | 6/1998 | Schwartz et al. |
| 5,783,691 A | 7/1998 | Malson et al. |
| 5,976,526 A | 11/1999 | Atala |
| 6,060,053 A | 5/2000 | Atala |
| 6,251,876 B1 | 6/2001 | Bellini et al. |
| 6,586,493 B1 | 7/2003 | Massia et al. |
| 7,060,287 B1 | 6/2006 | Hubbard et al. |
| 7,157,080 B2 | 1/2007 | Radice et al. |
| 2001/0027237 A1 | 10/2001 | Mayes et al. |
| 2004/0047892 A1 | 3/2004 | Desrosiers et al. |
| 2004/0063206 A1 | 4/2004 | Rowley et al. |
| 2004/0127698 A1 | 7/2004 | Tsai et al. |
| 2004/0185021 A1 | 9/2004 | Hubbard |
| 2005/0065616 A1 | 3/2005 | Ankorina-Stark et al. |
| 2006/0040894 A1 | 2/2006 | Hunter et al. |
| 2006/0040895 A1 | 2/2006 | Thacker |
| 2007/0014729 A1 | 1/2007 | Farhat et al. |
| 2009/0305983 A1* | 12/2009 | Ying et al. ............ 514/12 |

FOREIGN PATENT DOCUMENTS

| EP | 0 516026 A1 | 12/1992 |
|---|---|---|
| EP | 0 718312 A2 | 6/1996 |
| EP | 1312383 A2 | 5/2003 |
| JP | 54-36388 | 3/1979 |
| JP | 62-64803 A | 3/1987 |
| JP | 6-105901 A | 4/1994 |
| JP | 7-102002 | 4/1995 |

(Continued)

OTHER PUBLICATIONS

Aeschbach, R., Amado, R. and Neukom, H., "Formation of Dityrosine Cross-Links in Proteins by Oxidation of Tyrosine Residues," Biochimica et Biophysica Acta, Protein Structure, vol. 439, No. 1, pp. 292-301, 1976. Akkara, J.A., Senecal, K.J. and Kaplan, D.L., "Synthesis and Characterization of Polymers Produced by Horseradish Peroxidase in Dioxane," J. Polymer Science, Polymer Chemistry, vol. 29, pp. 1561-1574, 1991.
Ishii, T., "Structure and functions of feruloylated polysaccharides," Plant Science, vol. 127, pp. 111-127, 1997.
Sofia, S.J., Singh, A. and Kaplan, D.L., "Peroxidase-Catalyzed Crosslinking of Functionalized Polyaspartic Acid Polymers," J. Macromolecular Science, Pure and Applied Chemistry, vol. A39, No. 10, pp. 1151-1181, 2002.

(Continued)

*Primary Examiner* — Irina S Zemel
(74) *Attorney, Agent, or Firm* — Pearne & Gordon LLP

(57) ABSTRACT

A dihydroxyphenyl cross-linked macromolecular network is provided that is useful in artificial tissue and tissue engineering applications, particularly to provide a synthetic macromolecular network for a wide variety of tissue types. In particular, artificial or synthetic cartilage, vocal cord material, vitreous material, soft tissue material and mitral valve material are described. In an embodiment, the network is composed of tyramine-substituted and cross-linked hyaluronan molecules, wherein cross-linking is achieved via peroxidase-mediated dityramine-linkages that can be performed in vivo. The dityramine bonds provide a stable, coherent hyaluronan-based hydrogel with desired physical properties.

48 Claims, 16 Drawing Sheets
(9 of 16 Drawing Sheet(s) Filed in Color)

FOREIGN PATENT DOCUMENTS

| | | |
|---|---|---|
| JP | 8085703 | 4/1996 |
| JP | 09-059303 A | 3/1997 |
| JP | 2000-041691 A | 2/2000 |
| JP | 2001-097908 A | 4/2001 |
| JP | 2002-080501 | 3/2002 |
| JP | 2003-010308 | 1/2003 |
| WO | 85/04413 A1 | 10/1985 |
| WO | 89/02445 A1 | 3/1989 |
| WO | 89/07426 A1 | 8/1989 |
| WO | 90/09769 A1 | 9/1990 |
| WO | 93/07862 A1 | 4/1993 |
| WO | 97/18244 A1 | 5/1997 |
| WO | 99/57301 A1 | 11/1999 |
| WO | 00/01733 A1 | 1/2000 |
| WO | 00/11038 A1 | 3/2000 |
| WO | 00/16818 A1 | 3/2000 |
| WO | 00/37124 A1 | 6/2000 |
| WO | 00/46252 A1 | 8/2000 |
| WO | 00/54762 A2 | 9/2000 |
| WO | 01/00246 A2 | 1/2001 |
| WO | 01/00792 A1 | 1/2001 |
| WO | 01/85845 A1 | 11/2001 |
| WO | 02/18450 A1 | 3/2002 |
| WO | 02/39948 A2 | 5/2002 |
| WO | 02/060375 A2 | 8/2002 |
| WO | 02/068383 A2 | 9/2002 |
| WO | 03/006068 A1 | 1/2003 |
| WO | 03/007879 A2 | 1/2003 |
| WO | 03/018033 A1 | 3/2003 |
| WO | 03/018044 A1 | 3/2003 |
| WO | 03/090765 A1 | 6/2003 |
| WO | 03/061626 A1 | 7/2003 |
| WO | 03/072157 A1 | 9/2003 |
| WO | 03/076475 A1 | 9/2003 |
| WO | 2004/050712 A1 | 6/2004 |
| WO | 2007/097710 A1 | 8/2007 |

OTHER PUBLICATIONS

Tomihata, K. and Ikada, Y., "Crosslinking and degradation of biopolymer," Recent Res. Devel. Biotech. & Bioeng., vol. 4, pp. 35-49, 2001.

Brown, A.L., Srokowski, E.M., Shu, X.Z., Prestwich, G.D. and Woodhouse, K.A., "Development of a model bladder extracellular matrix combining disulfide cross-linked hyaluronan with decellularized bladder tissue," Macromol. Biosci., vol. 6, No. 8, pp. 648-657, Aug. 2006.

Funakoshi, T., Majima, T., Iwasaki, N. Suenaga, N., Sawaguchi, N., Shimode, K., Minami, A., Harada, K. and Nishimura, S., "Application of tissue engineering techniques for rotator cuff regeneration using a chitosan-based hyaluronan hybrid fiber scaffold," Am. J. Sports Med., vol. 33, No. 8, pp. 1193-1201, 2005.

Ghosh, K., Ren, X.D., Shu, X.Z., Prestwich, G.D. and Clark, R.A.F., "Fibronectin functional domains coupled to hyaluronan stimulate adult human dermal fibroblast responses critical for wound healing," Tissue Eng., vol. 12, No. 3, pp. 601-613, 2006.

Goldberg, V.M. and Buckwalter, J.A., "Hyaluronans in the treatment of osteoarthritis of the knee: Evidence for disease-modifying activity," Osteoarthritis and Cartilage 13(3), pp. 216-224, 2005.

Hu, M., Sabelman, E.E., Cao, Y., Chang, J. and Hentz, V.R., "Three-dimensional hyaluronic acid grafts promote healing and reduce scar formation in skin incision wounds," J. Biomed. Mater. Res. Part B: Appl. Biomater., vol. 67, No. 1, pp. 586-592, Oct. 2003.

Shu, X.Z., Ahmad, S., Liu, Y. and Prestwich, G.D., "Synthesis and evaluation of injectable, in situ crosslinkable synthetic extracellular matrices for tissue engineering," J. Biomed. Mater. Res. A., vol. 79, No. 4, pp. 902-912, Dec. 2006.

Yang, S.H., Chen, P.Q., Chen, Y.F. and Lin, F.H., "An In-vitro Study on Regeneration of Human Nucleus Pulposus by Using Gelatin/Chondroitin-6-Sulfate/Hyaluronan Tri-copolymer Scaffold," Artificial Organs, vol. 29, No. 10, pp. 806-814, 2005.

Darr, A. and Calabro, A., "Synthesis and characterization of tyramine-based hyaluronan hydrogels," J. Mater. Sci.: Mater. Med., vol. 20, No. 1, pp. 33-44, Jan. 2009.

Anderson, Svend Olav, "Cross-links in resilin identified as dityrosine and trityrosine," Biochimica et Biophysica Acta, General Subjects, vol. 93, No. 1, pp. 213-215, XP002363818, Copenhagen, 1964.

Anderson, Svend Olav, "Regional differences in degree of resilin cross-linking in the desert locust, *Schistocerca gregaria*," Insect Biochemistry and Molecular Biology 34, pp. 459-466, 2004.

Aslam, M. and Dent A., Bioconjugation: Protein Coupling Techniques for the Biomedical Sciences, Chapters 5 and 6, pp. 216-482, Macmillan Reference Ltd., London, UK, 1998.

Blumenkrantz, N. and Asboe-Hansen, G. "New method for quantitative determination of uronic acids," Anal. Biochem. 54, pp. 484-489, 1973.

Brittberg, M., Lindahl, A., Nilsson, A., Ohlsson, C., Isaksson, O., and Peterson, L., "Treatment of deep cartilage defects in the knee with autologous chondrocyte transplantation," N. Engl. J. Med. 331, pp. 889-895, 1994.

Buckwalter, J.A. and Mankin, H.J., "Articular cartilage: Degeneration and osteoarthrosis, repair, regeneration, and transplantation," J. Bone Joint Surgery [Am] 79A, pp. 612-632, 1997.

Bulpitt, P. and Aeschlimann, D., "New strategy for chemical modification of hyaluronic acid: Preparation of functionalized derivatives and their use in the formation of novel biocompatible hydrogels," J. Biomed. Mater. Res. 47, pp. 152-169, 1999.

Calabro, A., Benavides, M., Tammi, M., Hascall, V.C., and Midura, R.J., "Microanalysis of enzyme digests of hyaluronan and chondroitin/dermatan sulfate by fluorophore-assisted carbohydrate electrophoresis (FACE)," Glycobiology 10, pp. 273-281, 2000.

Calabro, A., Hascall, V.C., and Midura, R.J., "Adaptation of FACE methodology for microanalysis of total hyaluronan and chondroitin sulfate composition from cartilage," Glycobiology 10, pp. 283-293, 2000.

De La Motte, C.A., Hascall, V.C., Calabro, A., Yen-Lieberman, B. and Strong, S.A., "Mononuclear leukocytes preferentially bind via CD44 to hyaluronan on human intestinal mucosal smooth muscle cells after virus infection or treatment with poly(I:C)," J. Biol. Chem. 274, pp. 30747-30755, 1999.

Gross, A.J., "The oxidation of tyramine and related compounds by peroxidase," Ph.D. Thesis, MIT, pp. 1-84, 1954.

Gross, A.J. and Sizer, I.W., "The Oxidation of Tyramine, Tyrosine and Related Compounds by Peroxidase," Dept. of Biology, MIT, vol. 234, No. 6, pp. 1611-1614, 1959.

Hunziker, E.B. and Rosenberg, L.C., "Repair of partial-thickness defects in articular cartilage: Cell recruitment from the synovial membrane," J. Bone Joint Surgery [Am] 78A, pp. 721-733, 1996.

Jurvelin, J.S., Buschmann, M.D. and Hunziker, E.B., "Optical and mechanical determination of Poisson's ration of adult bovine humeral articular cartilage," J. Biomech. 30(3), pp. 235-241, 1997.

Kalra, B., Kumar, A. and Gross, R.A., "Gel formation by enzyme-selective crosslinking of tyramine decorated poly(aspartamide)," Polymer Preprints 2000, 41(2), pp. 1804-1805, 2000.

Mow, V.C., Kuei, S.C., Lai, W.M. and Armstrong, C.G., "Biphasic creep and stress relaxation of articular cartilage in compression: theory and experiments," J. Biomech. Engin. 102, pp. 73-84, 1980.

Pouyani, T., Kuo, J.W., Harbison, G.S. and Prestwich, G.D., "Solid-state NMR of N-acylureas derived from the reaction of hyaluronic acid with isotopically-labeled carbodiimides," J. Am. Chem. Soc., 114, pp. 5972-5976, 1992.

Sehgal, D. and Vijay, I.K., "A method for the high efficiency of water-soluble carbodiimide-mediated amidation," Anal. Biochem. 218, pp. 87-91, 1994.

Soltz, M.A. and Ateshian, G.A., "A conewise linear elasticity mixture model for the analysis of tension-compression nonlinearity in articular cartilage," J. Biomech. Engin. 122, pp. 576-586, 2000.

Thornton, T.D. and Savage, P.E., "Phenol oxidation pathways in supercritical water," Industrial & Engineering Chemistry Research, vol. 31, pp. 2451-2456, XP002363819, 1992.

Wells-Knect, Mary C. et al., "Oxidized Amino Acids in Lens Protein with Age," J. Biol. Chem., vol. 268, No. 17, pp. 12348-12352, 1993.

Office action issued Aug. 13, 2010 in related Canadian Patent Application No. 2,512,730.

English translation of Office action issued Aug. 4, 2009 in related Japanese Patent Application Serial No. 2006-500869.

Kurisawa, M. et al., "Injectable biodegradable hydrogels composed of hyaluronic acid-tyramine conjugates for drug delivery and tissue engineering," 2005, Chem. Commun., 26, 4312-4314.

Raja, et al., "Preparation of Alkylamine and 125I-Radiolabeled Derivatives of Hyaluronic Acid Uniquely Modified at the Reducing End," 1984, Analytical Biochemistry, vol. 139, pp. 168-177.

Fukuoka et al., "Polymerization of Polyfunctional Macromolecules: Synthesis of a New Class of High Molecular Weight Poly(amino acid)s by Oxidative Coupling of Phenol-Containing Precursor Polymers," 2004, Biomacromolecules vol. 5, No. 3, pp. 977-983.

Extended European search report issued Jan. 16, 2012 in corresponding European Patent Application No. 05773274.5.

* cited by examiner

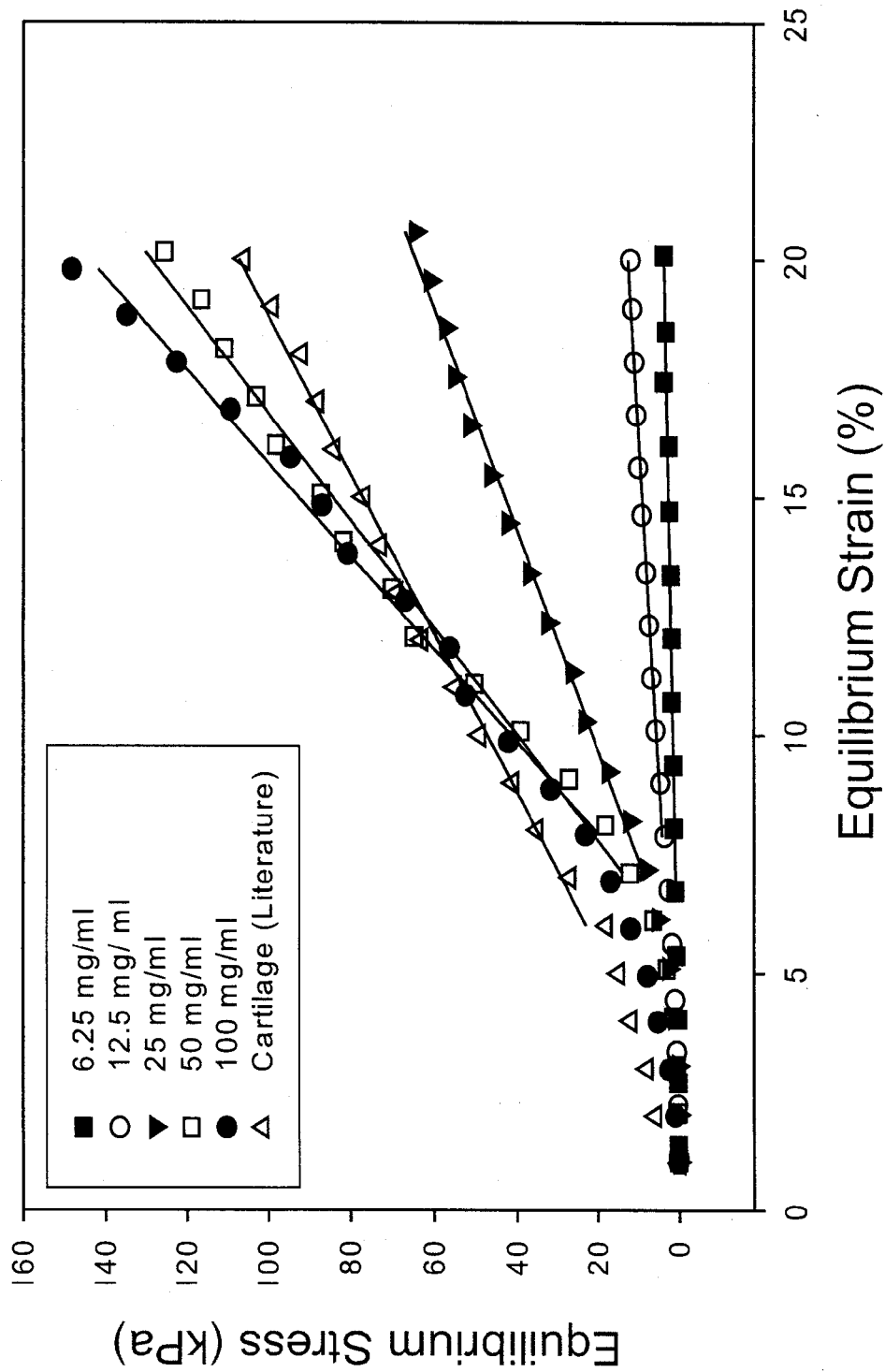

Equilibrium Stress Versus Equilibrium Strain Curves for T-Aggrecan Hydrogels

Relationship of Aggregate Modulus to Hexuronic Acid Concentration of T-Based Hydrogels Rabbit Vocal Cord Augmentation Model
(Two Weeks)

Subcutaneous Rat Transplanted
100 mg/ml T-HA Hydrogel Plugs
(1 Month)

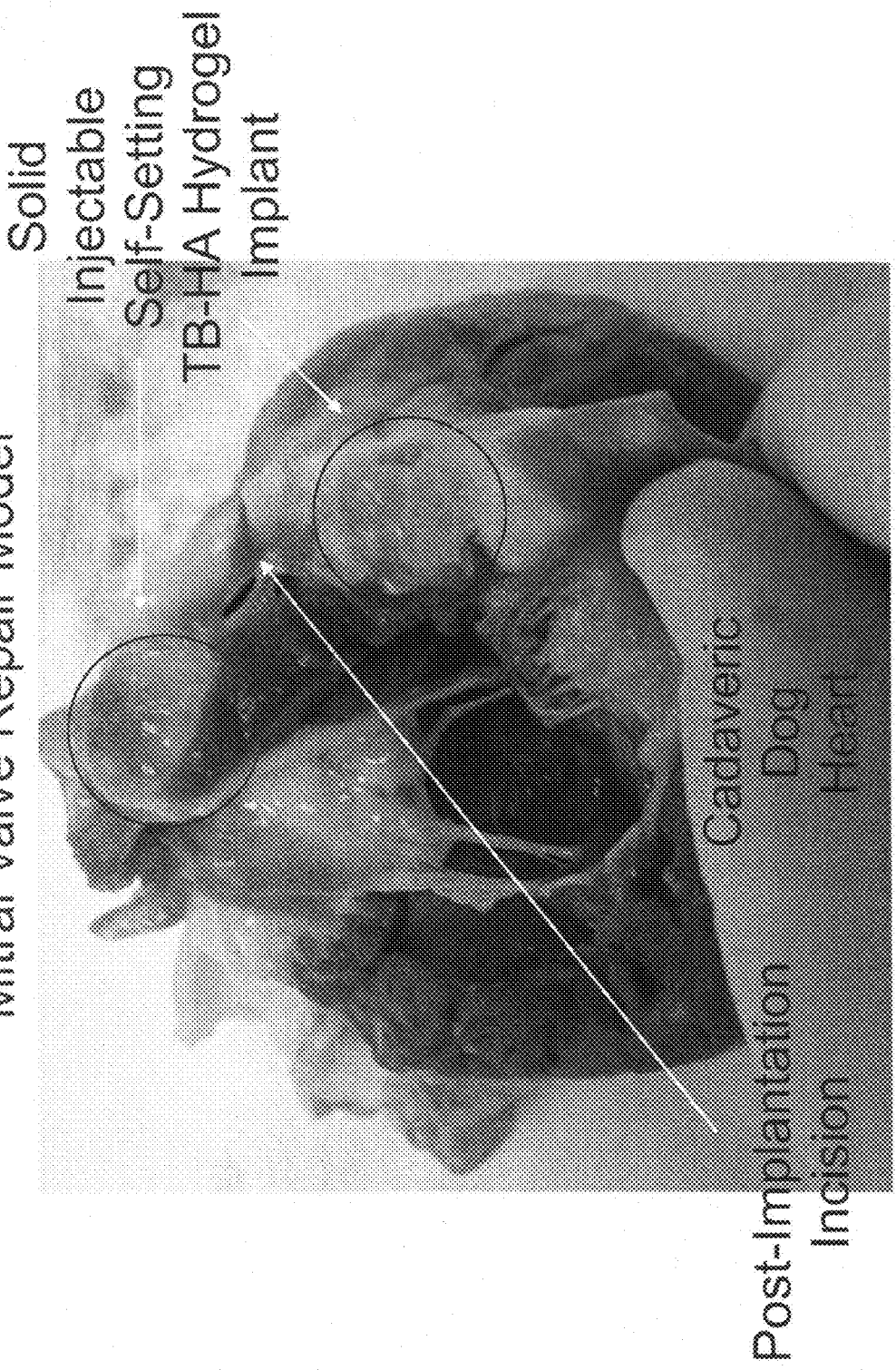

HYDROXYPHENYL CROSS-LINKED MACROMOLECULAR NETWORK AND APPLICATIONS THEREOF

This application is a continuation of application Ser. No. 11/176,544 filed Jul. 7, 2005 (now Pat. No. 7,465,766), which application claims the benefit of U.S. Provisional Patent Application Ser. No. 60/586,585 filed Jul. 9, 2004, and is a continuation-in-part of application Ser. No. 10/753,779 filed Jan. 8, 2004 (now U.S. Pat. No. 6,982,298), which application claims the benefit of U.S. Provisional Patent Application Ser. No. 60/439,201 filed on Jan. 10, 2003.

BACKGROUND OF THE INVENTION

Articular cartilage performs an essential function in healthy joints. It is responsible for absorbing and dissipating impact and frictional loads in order to divert these loads away from bones, to protect the bones from damage. Cartilage performs this function by transferring the loading force to a fluid phase within a three-dimensional network of aggrecan molecules, themselves constrained (described in the next paragraph) within the joint space. Aggrecan molecules have up to 100 chondroitin sulfate (CS) chains attached to a core protein, with each chondroitin sulfate chain possessing multiple negatively charged sulfate groups along their length. The effect of all these sulfate groups is to cause each of the chondroitin sulfate chains in a single aggrecan molecule to repel one another, (resulting in the aggrecan molecule having the maximum possible volume at rest), and also to cause adjacent aggrecan molecules in a cartilage aggregate to repel one another.

In healthy cartilage, aggrecan molecules are attached to long hyaluronan chains, which are in turn constrained in large cartilage aggregates within the joint space by an extracellular collagen fibril matrix. Thus, even though adjacent chondroitin sulfate chains in each aggrecan molecule (and adjacent aggrecan molecules attached to the same or a different hyaluronan chain) repel one another, they are nonetheless constrained within the collagen matrix. See FIG. 1 depicting normal, healthy cartilage. Because the chondroitin sulfate chains are so repulsive, the hyaluronan-aggrecan network (or macromolecular network) expands as much as possible within the constraints of the collagen matrix to achieve the lowest possible energy state at rest; i.e. to allow the maximum possible spacing between adjacent negatively charged sulfate groups. As a result, network molecules are highly resistant to being shifted or displaced in order to avoid approaching an adjacent network molecule. These large cartilage aggregates are trapped at one fifth their free solution volume within a meshwork of collagen fibers, which resist any further swelling. Cartilage aggregates with their high negative charge density bind large solvent domains, and contribute to cartilage's ability to absorb loads and resist deformation. Upon compression, the distance between the fixed-negative charge groups on the proteoglycans decreases, which increases the charge-to-charge repulsive forces as well as the concentration of free-floating positive counterions (such as $Ca^{2+}$ and $Na^+$). Both effects contribute to the viscoelastic nature of cartilage and its ability to resist deformation and absorb compressive loads, further described below.

Within the macromolecular network are water molecules which provide a substantially continuous fluid phase. The macromolecular network diverts impact and frictional loads away from bones by transferring them to the continuous fluid (water) phase as follows. As a joint undergoes a load, the force is absorbed first by the macromolecular network, where it acts on and tends to deform or compress the network. The force sets up pressure gradients in the fluid phase in order to induce fluid flow to accommodate network deformation or compression resulting from the load. But the fluid cannot negotiate the tight macromolecular network, packed with the repulsive chondroitin sulfate chains, sufficiently to accommodate a bulk flow of water without shifting or displacing the network molecules. Hence, individual water molecules may diffuse within the network, but the bulk fluid phase is substantially constrained from flowing through the network except at a much slowed rate due to the resistance to displacement of network molecules. Because the water molecules cannot flow readily despite the pressure gradients, the energy from the impact or frictional load is transferred to and absorbed by the fluid phase where it contributes to compressing the liquid water until the water can be sufficiently displaced to accommodate the network conformation and the pressure gradients have subsided. The overall result is that cartilage absorbs the potentially harmful load, thereby diverting it from bone.

Through this elegant mechanism, normal cartilage is capable of absorbing significant loads by transferring the bulk of the loading force to a fluid phase constrained within a macromolecular network. This arrangement has yet to be adequately duplicated via artificial or synthetic means in the prior art. Consequently, there is no adequate remedy for cartilage degenerative disorders, such as arthritic disorders, where the aggrecan molecules become separated from their hyaluronan chains and are digested or otherwise carried out from the cartilage aggregates.

Osteoarthritis and rheumatoid arthritis affect an estimated 20.7 and 2.1 million Americans, respectively. Osteoarthritis alone is responsible for roughly 7 million physician visits a year. For severe disabling arthritis, current treatment involves total joint replacement with on average 168,000 total hip replacements and 267,000 total knee replacements performed per year in the U.S. alone. Defects in articular cartilage present a complicated treatment problem because of the limited capacity of chondrocytes to repair cartilage. Treatment strategies to date have focused on the use of autologous chondrocytes expanded in culture or the recruitment of mesenchymal stem cells in vivo by chemotactic or mitogenic agents. The intent of these strategies is to increase and/or activate the chondrocyte population so as to resynthesize a normal, healthy articular cartilage surface. One major difficulty associated with these strategies is the inability to maintain these agents at the site of the defect. Hyaluronan has been proposed as a candidate for the development of biomaterials for local delivery of chondrocytes or bioactive agents because of its unique properties, including excellent biocompatibility, degradability, and rheological and physiochemical properties. However, it has been unknown whether chondrocytes suspended in a tissue engineered hyaluronan matrix would be able to synthesize a new cartilage matrix with mechanical properties comparable to normal, healthy articular cartilage. This is because conventional biomaterials made from hyaluronan are formed through chemistries that are incompatible with maintaining cell viability. Chondrocytes must be introduced to the matrices after matrix formation with variable and normally poor results.

Accordingly, there is a need in the art for an artificial or synthetic matrix that can effectively divert a loading force from bones in an effective manner. Preferably, such a matrix can be provided in situ or in vivo to repair or replace articular cartilage during an orthopedic surgical procedure. Most preferably, the artificial or synthetic matrix can be provided to an in situ or in vivo target site as a liquid or a plurality of liquids, and can set up in place to provide a substantially seamless integration with existing cartilaginous and/or bony tissue in a patient.

It also is desirable to provide an artificial or synthetic matrix that can be used or adapted to synthesize a variety of replacement tissues.

SUMMARY OF THE INVENTION

A synthetic macromolecular network is provided including a macromolecular network that includes the following structure

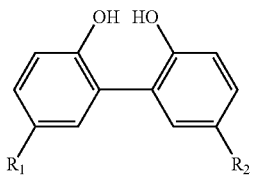

wherein $R_1$ and $R_2$ each comprises a structure selected from the group consisting of polycarboxylates, polyamines, polyhydroxyphenyl molecules, and copolymers thereof, and wherein $R_1$ and $R_2$ can be the same or different structures.

More generally, a synthetic macromolecular network is provided that comprises macromolecules selected from the group consisting of hydroxyphenyl-substituted polycarboxylates, hydroxyphenyl-substituted polyamines, other polyhydroxyphenyl molecules, and copolymers thereof, as well as at least one dihydroxyphenyl linkage linking different macromolecules or linking different sites on the same macromolecule.

A variety of synthetic, implantable tissue materials also are provided which include or are composed of the macromolecular network mentioned in the preceding paragraph, including a synthetic, implantable cartilage material; a synthetic, implantable vocal cord material; a synthetic, implantable vitreous material; a synthetic, implantable soft tissue material; and a synthetic, implantable mitral valve material.

BRIEF DESCRIPTION OF THE DRAWINGS

The file of this patent contains at least one drawing executed in color. Copies of this patent with color drawings will be provided by the Patent Office upon request and payment of the necessary fee.

FIG. 14 is a photograph of a cadaveric canine heart used to specify T-HA hydrogel materials for mitral valve repair as described in Example 10.

DETAILED DESCRIPTION OF PREFERRED EMBODIMENTS OF THE INVENTION

As used herein, the term polycarboxylate means a molecule, structure or species having a chain length of at least two functional groups or units, wherein at least two such groups or units of the chain are or comprise carboxylic acid groups that are sterically accessible to a nucleophilic substitution reaction as described herein. Also as used herein, the term polyamine means a molecule, structure or species having a chain length of at least two functional groups or units, wherein at least two such groups or units of the chain are or comprise primary amine groups that are available for a nucleophilic substitution reaction. Also as used herein, a polyhydroxyphenyl molecule means a molecule having a chain length of at least two functional groups or units, wherein at least two such groups or units of the chain are or comprise hydroxyphenyl groups that can be linked to another hydroxyphenyl group via a C—C bond. Also as used herein, a hydrogel is a material that is prepared comprising a macromolecular network that is used or useful in tissue replacement or engineering applications, e.g. as artificial cartilage, as a material to coat surgical instruments to prevent tissue irritation, or to provide a semi-permeable membrane such as for use in an artificial kidney, etc.

The invention includes a novel structure of a macromolecular network that has been formed by linking hydroxyphenyl groups attached to adjacent long chain macromolecules, resulting in effectively cross-linking the macromolecules to provide a large network. The basic cross-linking structure of the network is shown below

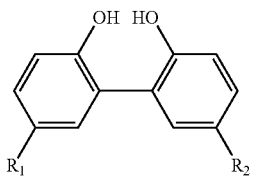

where $R_1$ and $R_2$ are each long chain macromolecules. $R_1$ and $R_2$ can be the same molecule or different molecules, but it will be understood that to provide a suitable network, $R_1$ and $R_2$ will be different molecules for at least a portion of the dihydroxyphenyl linkages in a network according to the invention. It is not necessary, though it is preferred, that $R_1$ and $R_2$ are the same species of molecule.

Figure 1:
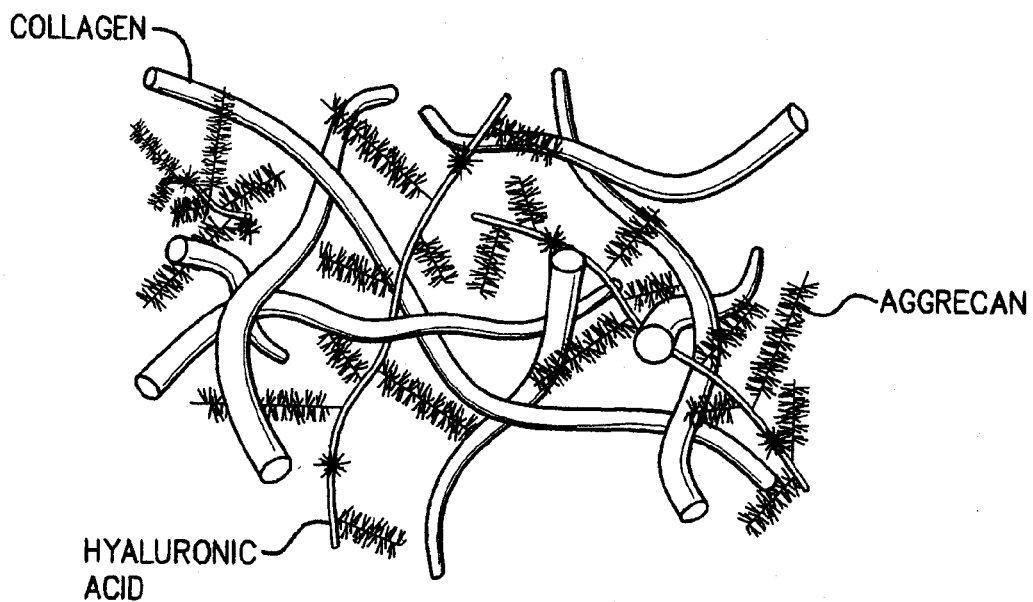
FIG. 1 is a schematic diagram of normal, healthy human cartilage.
Figure 2:
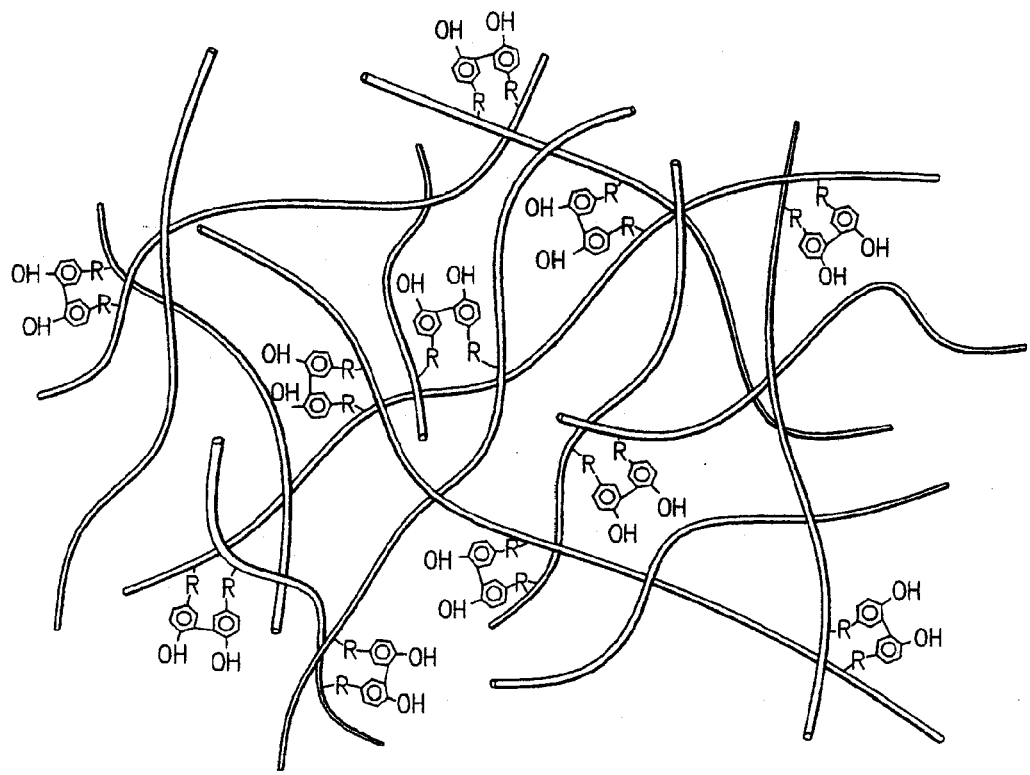
FIG. 2 is a schematic diagram of a dihydroxyphenyl cross-linked macromolecular network according to the invention.

By providing a plurality of these dihydroxyphenyl linkages between adjacent macromolecules, a network of dihydroxyphenyl cross-linked macromolecules is provided as shown schematically in FIG. 2. In the figure, the macromolecules are represented schematically by cylindrical strands, each preferably having at least two hydroxyphenyl groups attached along its length. It is noted that not every hydroxyphenyl group must be linked to another hydroxyphenyl group.

Briefly, the disclosed invention involves covalent coupling of hydroxyphenyl containing compounds, including but not limited to tyramine, through their primary amine (or carboxyl) groups to carboxyl (or primary amine) groups on various polymeric scaffold materials, including but not limited to hyaluronan or chondroitin sulfate (e.g. in the form of aggrecan), via a carbodiimide-mediated reaction. After isolation and purification of the hydroxyphenyl-substituted polymeric scaffolds, the hydroxyphenyl residues are selectively cross-linked by horseradish peroxidase (HRP) in the presence of very dilute hydrogen peroxide to form hydrogels. As will become apparent, the hydrogels made as described herein are or can be used as a fully implantable, non-immunogenic synthetic tissue matrix material that can be implanted into the body for a variety of purposes as will be described. As used herein, 'implantable' refers both to surgical implantation of a hydrogel as through a surgical incision, and to provision of the hydrogel within the body via injection, e.g. using a syringe. Whether surgically implanted or injected, the implantable hydrogels can be provided within the body already cross-linked (ex vivo cross-linking) or otherwise it can be cross-linked in situ at the site of implantation within the body as will be further described.

The first step in providing the macromolecular network is to prepare or provide the long-chain macromolecules having periodic hydroxyphenyl groups attached. In one embodiment, the macromolecules are polyhydroxyphenyl molecules which already have multiple or periodic hydroxyphenyl groups, such as polyphenols. Suitable polyphenols include polyamino acids (e.g. polytyrosine), epigallocatechin (EGC), and epigallocatechin gallate (EGCG) isolated from green tea, less preferably other polyphenols.

In a further embodiment, the hydroxyphenyl groups can be added to the macromolecules periodically or randomly along their length via a chemical reaction. A preferred method of adding hydroxyphenyl groups to the macromolecules is to utilize a carbodiimide-mediated substitution reaction pathway to provide an amide bond between a primary amine having a hydroxyphenyl group and a carboxylic acid group attached to the macromolecules. In this method, the long-chain macromolecule preferably is a polycarboxylate molecule, having periodic carboxylic acid groups along its length. The hydroxyphenyl groups are provided as part of smaller molecules having primary amine groups that can be attached to the carboxyl carbon atoms of a carboxylic acid group on the long-chain macromolecules via the carbodiimide pathway. The reaction proceeds as follows:

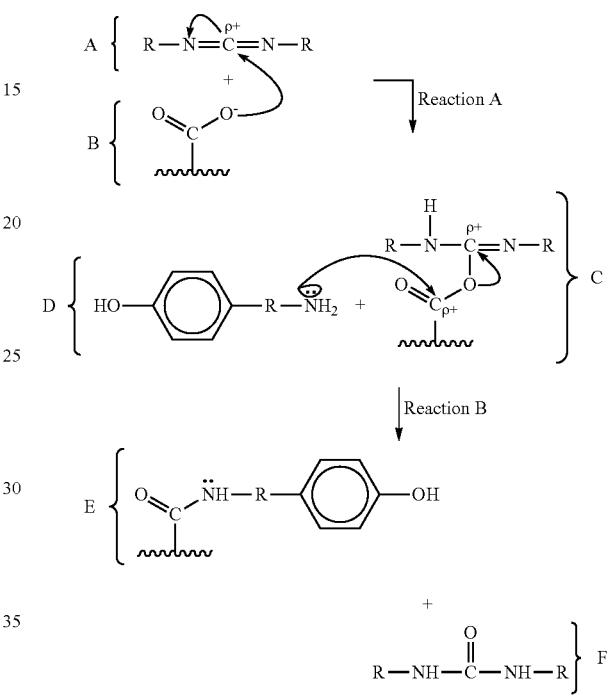

where:
Structure A is a carbodiimide;
Structure B is a polycarboxylate (though only one $CO_2H$ group is shown);
Structure C is the product of Reaction A and is an activated O-acylisourea;
Structure D is a primary amine having a hydroxyphenyl group;
Structure E is a hydroxyphenyl-substituted polycarboxylate; and
Structure F is an acylurea byproduct;
wherein individual Rs can be individually selected, the same or different from one another, to be a straight chain or branched alkane or acyl group, or any other structure that does not interfere with the carbodiimide reaction pathway to provide the amide bond between the $NH_2$ and $CO_2H$ groups as shown in Structure E above.

In the above-illustrated pathway, Reaction A represents a carbodiimide activation of the carboxyl group to provide an activated O-acylisourea intermediate. The electropositive carbon atom of this intermediate is receptive to nucleophilic attack by the lone pair of electrons on a nitrogen atom of an adjacent primary amine molecule having an attached hydroxyphenyl group. The products of this nucleophilic substitution reaction (Reaction B) are a hydroxyphenyl-substituted polycarboxylate and an acylurea byproduct which can be dialyzed out to provide a substantially pure hydroxyphenyl-substituted polycarboxylate product.

Certain side-reactions are possible in the above-described carbodiimide reaction pathway chemistry and should be considered by the person having ordinary skill in the art. First, the carbodiimide can react with nucleophiles other than the carboxylate oxygen atom of the polycarboxylate molecule required to form the desired O-acylisourea (reaction A). Such nucleophiles may include the amine and/or hydroxyphenyl groups of Structure D illustrated above. In particular, there are three potential side-reactions for Reaction A which can reduce the effective concentration of the carbodiimide and the primary amine having the hydroxyphenyl group (Structures A and D), and potentially lead to the creation of undesired adducts on the polycarboxylate (Structure B):

Reaction C:

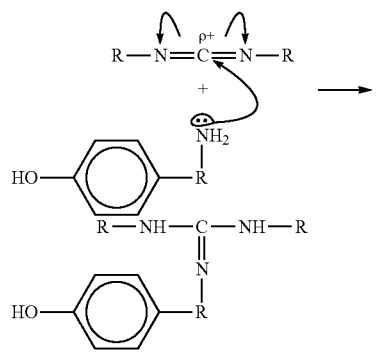

Reaction D:

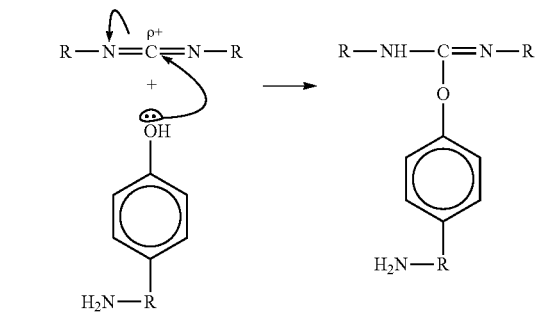

Reaction E:

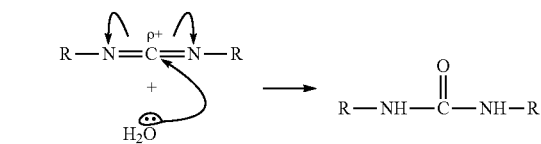

The product of an amine reaction with the carbodiimide (Reaction C) will not have a free amine group effectively reducing the amount of tyramine available for reaction with the O-acylisourea. This reaction also reduces the amount of carbodiimide available for formation of the desired O-acylisourea. The products of the hydroxyphenyl reaction (Reaction D) are not UV absorbent, which will make their detection by UV-spectroscopy in the final hydroxyphenyl-substituted polycarboxylate product (explained below) more difficult. However, because these products still contain free amine groups, they can form amide bonds with the polycarboxylate molecule via Reaction B. This can give rise to two unproductive hyaluronan-substituted structures, neither of which can participate in the peroxidase cross-linking reaction in the second step (described below) of preparing the cross-linked network due to the absence of an extractable phenolic hydroxyl hydrogen atom needed to generate the free radical (also explained below). Finally, the carbodiimide can react non-productively with water (Reaction E) to produce the same acylurea shown above as a byproduct of Reaction B, but with none of Structure E, the desired product.

Once the desired O-acylisourea product has been formed in Reaction A, there is again the possibility for certain additional side-reactions:

Reaction F:

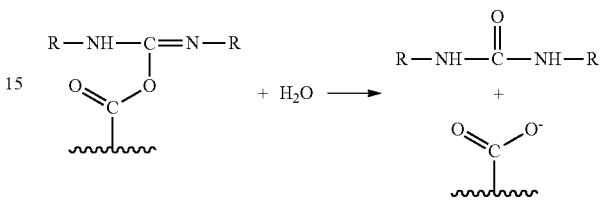

Reaction G:

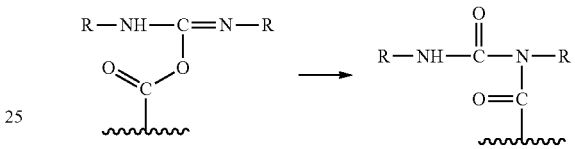

Reaction H:

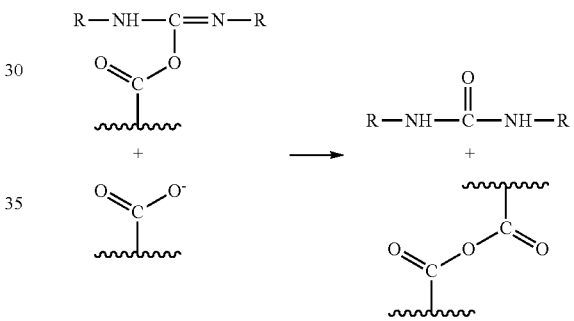

The O-acylisourea (Structure C) can be hydrolyzed as shown in Reaction F releasing the original unmodified polycarboxylate (Structure B) and the acylurea of the carbodiimide (Structure F). This is an unproductive reaction similar to reaction E, which reduces the effective concentration of the carbodiimide. The O-acylisourea, can also undergo an intramolecular rearrangement (Reaction G) to form two unreactive N-acylureas. These structures form unproductive adducts on the carboxylate molecule which cannot contribute to the peroxidase catalyzed cross-linking reaction (step 2 discussed below) for preparing a network according to the invention. The O-acylisourea can also react (Reaction H) with a second carboxyl group on either the same or a different polycarboxylate molecule to form an acid anhydride. This molecule can then react with Structure D to form the desired amide and regenerate the second carboxyl group. Thus there are two potential side-reactions for the O-acylisourea, which can reduce the effective concentration of the carbodiimide (Reactions F and G), and potentially lead to creation of undesired adducts on the polycarboxylate molecule.

Negative effects of these side reactions can be addressed through conventional techniques without undue experimentation.

Alternatively to the pathway shown above where the macromolecule (Structure B) is a polycarboxylate, the macromolecule can be a polyamine having multiple or periodic amine groups along its length, wherein the hydroxyphenyl groups then are provided as part of smaller carboxylic acid molecules. Suitable polyamines include: polyhexosamines such as chitosan (polyglucosamine); polyamino acids such as polylysine; polydeoxyribonucleotides such as poly (dA) (polydeoxyadenylic acid), poly(dC) (polydeoxycytidylic acid), and poly(dG) (polydeoxyguanylic acid); and polyribonucleotides such as poly(A) (polyadenylic acid), poly(C) (polycytidylic acid), and poly(G) (polyguanylic acid). The carbodimide-mediated reaction pathway proceeds exactly as explained above to form the amide bond between the amine group and carboxylic acid group except that, as will be understood by a person having ordinary skill in the art, the resulting product will be hydroxyphenyl-substituted polyamine instead of a polycarboxylate. Other peptides and/or proteins also can be used as the macromolecules in the present invention, either which have hydroxyphenyl groups disposed along their length, or to which hydroxyphenyl groups can be provided via a substitution reaction as described herein. For example, in addition to the peptides already disclosed herein, polyarginine can be used as the macromolecule.

When substituting onto a polycarboxylate molecule, suitable hydroxyphenyl-containing compounds for use in the present invention include those having a free primary amine that can be used to modify scaffold materials having multiple or periodic $CO_2H$ groups, including tyrosine (2-amino-3-(4-hydroxyphenyl) proprionic acid) and tyramine (tyrosamine or 2-(4-hydroxyphenyl) ethylamine). When substituting onto a polyamine, suitable hydroxyphenyl-containing compounds include those having a free $CO_2H$ group that can be used to modify scaffold materials having multiple or periodic primary $NH_2$ groups, including tyrosine, 3-(4-hydroxyphenyl) propionic acid and 4-hydroxyphenylacetic acid.

The second step in preparing a cross-linked macromolecular network according to the invention is to link the resulting macromolecules, now having one or more hydroxyphenyl groups attached, via a dihydroxyphenyl linking structure. In this step hydroxyphenyl groups attached to different macromolecules are linked via the reaction mechanism shown below using a peroxide reagent in the presence of a peroxidase:

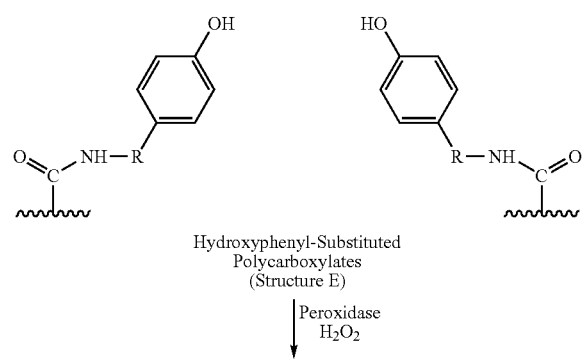

Hydroxyphenyl-Substituted
Polycarboxylates
(Structure E)

Peroxidase
$H_2O_2$

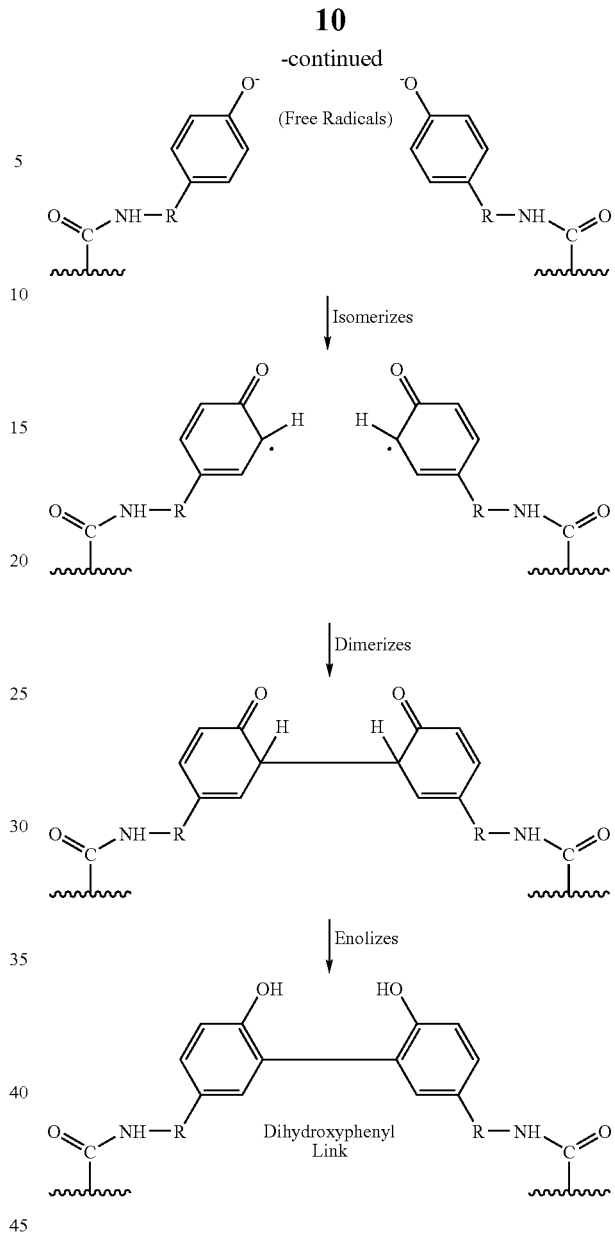

(It is noted that some dihydroxyphenyl linking may occur between different hydroxyphenyl groups attached to the same molecule as well). Peroxidase in the presence of a dilute peroxide (preferably $H_2O_2$) is able to extract the phenolic hydroxyl hydrogen atom from hydroxyphenyl containing compounds (such as tyramine) leaving the phenolic hydroxyl oxygen with a single unshared electron, an extremely reactive free radical. The free radical isomerizes to one of the two equivalent ortho-position carbons and then two such structures dimerize to form a covalent bond effectively crosslinking the structures, which after enolizing generates a dihydroxyphenyl dimer (a dihydroxyphenyl linkage such as dityramine linkage as described below).

For clarity, only a single dihydroxyphenyl linking reaction is shown above, but it will be understood that several or multiple such linkages will be produced when macromolecules having attached hydroxyphenyl groups are subjected to the reaction conditions (peroxide and peroxidase). Hydrogen peroxide is indicated in the above mechanism, but other suitable peroxides can be used. Also, the peroxidase preferably is horseradish peroxidase (HRP). Alternatively, any other suitable enzyme (or other agent) can be used that is capable of generating free-radicals for cross-linking scaffold materials containing hydroxyphenyl groups, preferably under ordinary metabolic conditions as described below.

We have shown that the interaction of horseradish peroxidase (Type II) and hydrogen peroxide ($H_2O_2$) is suitable for the production of cross-linked macromolecular networks. The mechanism comprises four distinct steps: (a) binding of peroxide to the heme-Fe(III) complex of the peroxidase to form an unstable peroxide complex, "Compound I"; (b) oxidation of the iron to generate a ferryl species with a pi-cation radical in the heme porphyrin ring, "Compound II"; (c) reduction of Compound II by one substrate (i.e. hydroxyphenyl or water) molecule to produce a product (i.e. hydroxyphenyl or superoxide) radical and another ferryl species, "Compound III"; (d) reduction of Compound III by a second substrate (i.e. hydroxyphenyl or water) molecule to release a second product (i.e. hydroxyphenyl or superoxide) radical and regenerate the native enzyme. Thus the peroxidase enzyme can either form hydroxyphenyl radicals required for cross-linking through interaction of hydroxyphenyl groups at the enzyme active site to directly create the desired radicals or through first generation of superoxide radicals, which then diffuse from the enzyme and interact with hydroxyphenyl groups to generate the desired radicals. Other compounds that have the potential to produce the same effect include any porphyrin containing compound (i.e. Photofrin below), which includes the peroxidase family, hemoproteins, or the structurally related chlorine compounds.

A number of other free radical initiators can be used to crosslink the hydroxyphenyl modified macromolecules described herein. A majority are based on the formation or inclusion of reactive oxygen species (ROS) such as, but not limited to, molecules of hydrogen peroxide, ions of hypochlorite, radicals like the hydroxyl radical, and the superoxide anion which is both ion and radical. Additional reactive molecules such as reactive nitrogen species or reactive sulfur species, or those free radical species involved in synthetic polymerization have the potential to be used for hydroxyphenyl cross-linking.

ROS are commonly produced in nature through the use of enzymes, and substrates. Additional enzymatic systems which have the potential to be used in the cross-linking process, as a result of production of superoxide radicals, include, but are not limited to xanthine-xanthine oxidase and NADPH-NADPH oxidase.

Another class of ROS free radical initiators that can be used involves the use of metallic cations. One example is based on the Fenton reaction, which takes place between hydrogen peroxide and a bivalent cation, such as $Fe^{2+}$. This process generates powerful free radicals when the catalyst reacts with hydrogen peroxide. The principal chemical reaction associated with Fenton's reaction is shown below:

$$H_2O_2 + Fe^{2+} \Rightarrow OH \cdot + OH^- + Fe^{3+}$$

where, $Fe^{2+}$=ferrous ion, $Fe^{3+}$=ferric ion, OH.=hydroxyl radicals

In addition to the initiation reaction described above that produces hydroxyl radicals, the Fenton's process can also produce superoxide radicals and hydroperoxide anions by additional chain propagation reactions described below. The perhydroxyl radical is known to be a weaker reductant compared to superoxide radical and hydroperoxide anions.

$$H_2O_2 + OH \cdot \Rightarrow HO_2 \cdot + H_2O$$

$$HO_2 \cdot \Rightarrow H^+ + O_2 \cdot^-$$

$$HO_2 \cdot + O_2 \cdot^- \Rightarrow HO_2^- + O_2$$

where $O_2 \cdot^-$=superoxide radical anion, $HO_2^-$=hydroperoxide anion, $HO_2.$=perhydroxyl radical.

We have demonstrated the ability for this reaction to crosslink tyramine substituted hyaluronan in the laboratory using ferrous sulfate in conjunction with hydrogen peroxide. Compounds which include, but are not limited to, bivalent cations of copper, chromium, vanadium and cobalt can be used in a similar manner. It is to be noted that while the hydroxyl free radical can be used to form a dityramine crosslink, it has also been shown to cleave HA chains, and thus may ultimately be unsuitable for ideal hydrogel formation.

Additional molecules or methods which can generate ROS include:

rubidium or cesium ions in the presence of oxygen to form superoxide radicals;

trivalent cations, which with hydrogen peroxide form free radicals and bivalent cations as shown below, which can subsequently follow the reactions involved in the Fenton process.

$$Fe^{+3} + H_2O_2 = Fe^{+2} + \cdot OOH + H^+$$

the cytotoxic and antitumor therapy Photofrin, which upon illumination with laser light at a wavelength of 630 nm causes propagation of a radical generating reaction that produces superoxide and hydroxyl radicals. In the absence of light, but the presence of hydrogen peroxide, the porphorin ring in Photofrin should operate by the same reaction as for the peroxidase enzyme above.

UV light and hydrogen peroxide to form hydroxyl and superoxide free radicals.

the persulfate family in combination with TEMED.

As noted above, one alternative method for generating such free-radicals is to use Photofrin as an alternative, non-enzymatic, light-activated cross-linking agent to cross-link the macromolecular network described herein, e.g. tyramine-substituted hyaluronan to form tyramine cross-linked hyaluronan hydrogels. Photofrin®, which is known in the art, generates free radicals which could initiate the cross-linking reaction as described herein in a manner similar to the peroxidase-$H_2O_2$ mechanism described above. Photofrin® is a porfimer sodium manufactured in powder or cake form by Wyeth-Ayerst Lederle Parenterals, Inc.

The dihydroxyphenyl cross-linked macromolecular network is superior to conventional cartilage or other tissue replacement or substitution methods and products, at least with respect to the ability to carry out an in situ cross-linking procedure, because the preferred cross-linking reaction is enzyme driven (peroxidase). This means the cross-linking reaction is carried out under ordinary in vivo or metabolic conditions of temperature such as 35-39° C. (e.g. about 37° C.), pH range of 6-7 (e.g. about 6.5), reagents etc. (A peroxide, such as hydrogen peroxide, is the only required reagent for the cross-linking reaction). In addition, Photofrin already is used in in vivo applications, e.g. ablative treatment of Barrett's esophagus, and the iron-based cross-linking mechanism also can be optimized for in vivo performance. Thus, the cross-linking reaction can be performed in vivo, to provide a cross-linked hydrogel at a surgical situs, such as an orthopedic surgical situs, to promote maximum seamless integration between the hydrogel and native tissue such as bony and cartilaginous tissue. Integration of the new hydrogel scaffold with native cartilage matrix may occur immediately as the hydroxyphenyl-substituted macromolecular scaffold quickly penetrates into the existing cartilage matrix prior to cross-linking, and cross-links not only with other hydroxyphenyl-substituted macromolecular scaffold material but potentially with tyrosine residues of resident proteins in the existing cartilage matrix. This would eliminate a typical problem found with pre-formed matrix plugs, which is their poor integration into the native cartilage tissue. The ability to cross-link the hydrogel directly on the articular surface eliminates the need to surgically enlarge a defect to fit a pre-cast plug, as is necessary for hydrogels whose chemistries are toxic to or otherwise prohibit their formation inside the patient. It should be noted that most cartilage damage as a result of arthritis presents as a variable thinning of the articular surface, not holes of defined shape.

For the peroxidase mechanism, because the cross-linking reaction requires both the peroxide and a peroxidase (preferably horseradish peroxidase), solutions containing all but one of these components can be prepared for convenient application to a surgical site. For example, a solution comprising a tyramine—(or other hydroxyphenyl containing species) substituted polycarboxylate (such as tyramine-substituted hyaluronan, etc.) and the peroxidase can be prepared, with a second solution prepared containing the peroxide. Alternatively, the peroxide and the peroxidase can be swapped between the first and second solutions, the important thing being that the peroxide and peroxidase are kept separate (i.e. in separate solutions) until the cross-linking reaction is to be carried out. Then, the first solution is applied, (e.g. to an in vivo surgical situs), and the second solution is applied or sprayed over the first, in vivo, to cause in situ cross-linking of the tyramine residues. The cross linking reaction occurs in vivo. Other combinations will be evident from the present disclosure which are within the skill of a person of ordinary skill in the art.

Furthermore, because the cross-linking reaction occurs under ordinary metabolic conditions, additional living cells, such as chondrocytes, progenitor cells, stem cells, etc., can be provided directly to a medium containing the non-cross-linked hydroxyphenyl-substituted polycarboxylates or polyamines (or polyphenols), i.e. to the first or second solution from the preceding paragraph, wherein the cell-rich medium is applied with the macromolecules to the site in vivo, and the molecules are subsequently cross-linked via addition of peroxidase and peroxide. The result is a cross-linked macromolecular network containing the desired cells dispersed within it. Such a cell-enriched network is not possible in conventional tissue replacement matrices due to the harsh conditions of temperature and pH under which they are prepared. Further, as described below in Example 5, it has been demonstrated that the cells provided to the network as described above remain viable even after cross-linking of tyramine-substituted hyaluronan (also described below).

In a preferred embodiment particularly suitable for preparing synthetic cartilage as well as other synthetic or artificial tissues, the macromolecule used to produce the network is hyaluronan or hyaluronic acid (HA), and the hydroxyphenyl group is supplied in the form of tyramine. Hyaluronan (HA) is a ubiquitous molecule, which is most concentrated in specialized tissues such as cartilage, vocal cords, vitreous, synovial fluid, umbilical cord, and dermis. In these tissues, its function is manifold, influencing tissue viscosity, shock absorption, wound healing, and space filling. HA has been shown to influence many processes within the extracellular matrix (ECM) in native tissues where it is present including matrix assembly, cell proliferation, cell migration and embryonic/tissue development.

Figure 3:
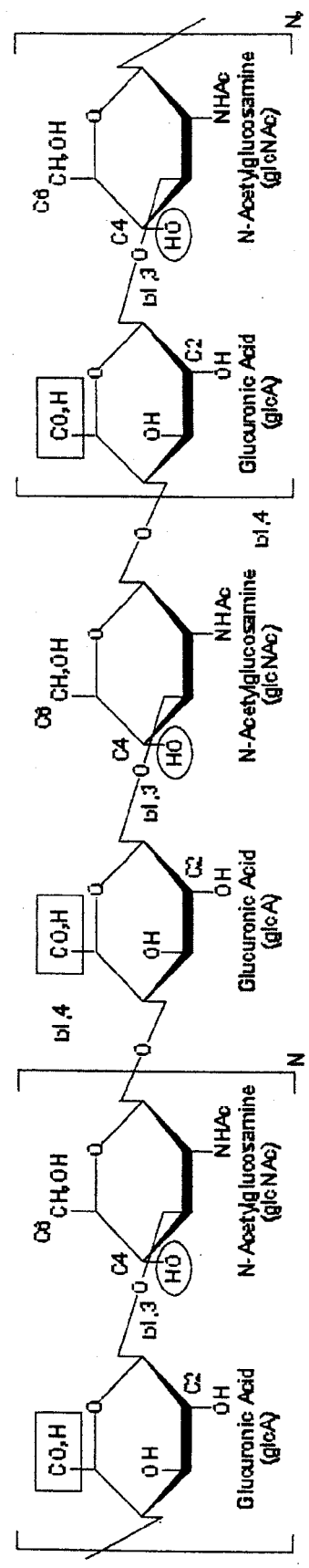
FIG. 3 is a structural formula of a hyaluronan molecule.

HA is composed of repeating pairs of glucuronic acid (glcA) and N-acetylglucosamine (glcNAc) residues linked by a β1,3 glycosidic bond as shown in FIG. 3. The glucuronic acid residue is particularly pertinent to the production of a macromolecular network as described herein as this sugar provides an available carboxyl group periodically along the repeat disaccharide structure of HA that is useful for hydroxyphenyl, i.e. tyramine, substitution. For each hyaluronan chain, this simple disaccharide is repeated up to 10,000 times or greater resulting in macromolecule that can have a molecular weight on the order 10 million daltons (10 megadaltons). Adjacent disaccharide units of HA are linked by a β1,4 glycosidic bond, also seen in FIG. 3. Each glcA residue has a carboxylic acid group ($CO_2H$) attached to the number 5 carbon atom of the glucose ring. Under biological conditions, HA is a negatively charged, randomly coiled polymer filling a volume more than 1,000 times greater than would be expected based on molecular weight and composition alone. As noted above, the strong negative charges attract cations and water, which allow HA to assume the form of a strongly hydrated gel in vivo, giving it a unique viscoelastic and shock-absorbing property. HA represents a readily available and desirable scaffolding material for tissue engineering applications as it is non-immunogenic, non-toxic and non-inflammatory. Also as a naturally occurring extracellular matrix (ECM) molecule it offers the advantages of being recognized by cell receptors, of interacting with other ECM molecules, and of being metabolized by normal physiological pathways.

Tyramine is a phenolic molecule having an ethyl amine group attached para to the OH group on the benzene ring. When these species are used, the mechanism for tyramine substitution onto the singly bound oxygen atom of a $CO_2H$ group on HA proceeds via the carbodiimide-mediated reaction mechanism described above as illustrated immediately below. The preferred carbodiimide species is 1-ethyl-3-(3-dimethylaminopropyl)carbodiimide (EDC) as shown.

where:
Structure A is EDC;
Structure B is hyaluronan (though only one $CO_2H$ group is shown);
Structure C is the product of Reaction A and is 1-ethyl-3-(3-dimethylaminopropyl) isourea;
Structure D is tyramine;
Structure E is tyramine-substituted hyaluronan; and
Structure F is 1-ethyl-3-(3-dimethylaminopropyl)urea (EDU).

In the above pathway, a negatively charged oxygen atom of the carboxyl group of the hyaluronan molecule attacks, via a nucleophilic reaction mechanism, the electron-deficient diamide carbon atom on the carbodiimide molecule (EDC) to form the activated O-acylisourea (Reaction A). The result is that the carbon atom of the HA carboxylate group becomes sufficiently electron deficient to be susceptible to nucleophilic attack by the unshared pair of electrons on the amine group of a tyramine molecule (Reaction B). Reaction A is preferably catalyzed by a suitable catalyst that will result in the formation of an active ester during Reaction A, thus permitting the reaction to be carried out at substantially neutral pH (e.g. pH=6.5). Suitable catalysts include N-hydroxysuccinimide (NHS), less preferably 1-hydroxybenzotriazole (HOBt) or N-hydroxysulfosuccinimide (NHSS), less preferably another suitable catalyst or combinations thereof effective to enhance the carbodiimide reaction by formation of an active ester in order to minimize the unproductive hydrolysis of carbodiimides at higher pHs. Less preferably other carbodiimides besides EDC can be used, including 1-cyclohexyl-3-[2-(4-methylmorpholino)ethyl]carbodiimide (CMC), and dicyclohexylcarbodiimide (DCC).

The result of Reaction A above is O-acylisourea-substituted hyaluronan; essentially the EDC molecule has been temporarily substituted onto the carboxylic acid group of a glcA residue from the HA molecule, making the carbon atom of the carboxylic acid group slightly positively charged. The electron pair from the terminal amine group of a tyramine molecule is then substituted onto the carbon atom via a nucleophilic substitution reaction as explained in the preceding paragraph (Reaction B). The result of Reaction B is the tyramine-substituted HA molecule (T-HA) and acylurea, a byproduct. It will be understood that Reactions A and B will result in a plurality of tyramine substitutions on the periodic glcA residues of HA molecules; a single substitution has been shown here for brevity and clarity.

After formation of T-HA, a plurality of T-HA molecules are reacted via peroxide and peroxidase enzyme to cross-link T-HA molecules as previously described and illustrated above. That is, the hydroxyphenyl groups on the tyramine residues now attached to HA molecules react with peroxide (preferably $H_2O_2$) in the presence of a peroxidase to remove the phenolic hydrogen atom resulting in a tyramine free radical, with the unpaired electron associated with the phenolic oxygen atom. This free radical species isomerizes or resonates, resulting in a resonance structure (or free radical isomer) with the unpaired electron now associated with an ortho carbon atom on the phenolic ring. In this position, the unpaired electron quickly reacts with a similarly situated unpaired electron on another tyramine free radical to form a covalent bond therebetween. The result is a free-radical driven dimerization reaction between different tyramine free radical residues attached to different glcAs of the same or different HA molecules. This dimerized species further enolizes to restore the now-linked tyramine residues, resulting in a dityramine linkage structure. It will be understood that a plurality of reactions as herein described will occur between adjacent tyramine residues, resulting in a cross-linked macromolecular network of T-HA molecules having the following cross-linking structure:

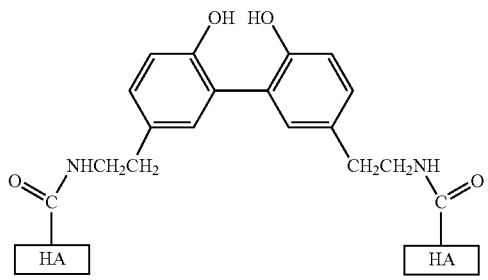

The cross-linked T-HA network can be provided with aggrecan molecules in a conventional manner, e.g. via link proteins, to provide a cross-linked T-HA network having aggrecan molecules attached to the HA chains. Thus, a network similar to that found in a normal cartilage aggregate can be provided, with the dityramine bonds holding the network together thereby constraining the contained aggrecan network, instead of collagen fibrils as in normal cartilage.

It will be understood from the present invention that other glycosaminoglycans (GAGs), polysaccharides and polycarboxylic acids can be used as the macromolecules for producing the cross-linked network disclosed herein. For example, suitable GAGs, other than HA, include chondroitin, chondroitin sulfate, dermatan sulfate, heparan sulfate and heparin. Other suitable polycarboxylates include: proteoglycans such as versican, aggrecan, and cartilage aggregates composed of aggrecan, hyaluronan and link protein; polyuronic acids such as polypectate (polygalacturonic acid), polyglucuronic acid, pectin (polygalacturonic acid methyl ester), colominic acid (poly[2,8-(N-acetylneuraminic acid)]), and alginate (poly [mannuronate-co-guluronate]); and amino acids (having at least 2 amino acid units) that meet the definition of polycarboxylate given above, such as polyaspartic acid, and polyglutamic acid. All of these can be substituted with one or a plurality of hydroxyphenyl groups using the carbodiimide-mediated reaction pathway disclosed herein by a person of ordinary skill in the art without undue experimentation.

As mentioned above, it is also to be understood that native polyphenol compounds, which already contain two or more hydroxyphenyl groups that can be cross-linked using the described enzyme catalysis chemistry can be used in place of the polycarboxylates and polyamines described above which must have the hydroxyphenyl groups added by a chemical reaction.

In another preferred embodiment, a network of tyramine cross-linked chondroitin sulfate molecules (either alone or provided as part of aggrecans) is provided to simulate or replace normal cartilage. Chondroitin sulfate is identical to hyaluronan except: 1) the repeat disaccharide structure contains N-acetylgalactosamine (galNAc) rather than glcNAc, a difference in only the position of the hydroxyl group attached to the 4-carbon (circled in FIG. 3); 2) the presence of O-sulfation on the hydroxyl groups at the 4- and/or 6-position of the galNAc residue and/or the 2-position of the glcA residue (FIG. 3); and 3) the size of the chondroitin sulfate chains, which are smaller than hyaluronan with between 20 to 100 repeating disaccharide units. (An aggrecan molecule is made up of multiple—roughly 100—chondroitin sulfate chains linked to a core protein through a linkage saccharide located at each chain's reducing end). In this embodiment, the negatively charged $SO_4^{2-}$ groups of adjacent (cross-linked) chondroitin sulfate molecules provide the principal repulsive force contributing to the compression resistance of the network aggregate while the tyramine cross-links constrain the chondroitin sulfate network from breaking or dissipating. The result is a similarly non-displaceable chondroitin sulfate network (and concomitant water-impermeability) as in normal cartilage, but without the extracellular collagen fibril matrix or the HA chains found in normal cartilage. In fact, by directly cross-linking chondroitin sulfate molecules, (instead of their core HA molecules as in the previously described embodiment), the repulsive force between adjacent chondroitin sulfate molecules may be strengthened, resulting in even stronger fluid flow resistance compared to normal cartilage. This may result in greater loading force absorption and dissipation capacity than normal cartilage because the interstitial fluid phase is even more constrained from flowing. In this embodiment, where chondroitin sulfate molecules are directly cross-linked, certain cartilage degenerative conditions are entirely circumvented; e.g. conditions where the core protein to which chondroitin sulfate molecules are ordinarily bonded in normal cartilage becomes cleaved between the HA binding domain (G1) and the second globular domain (G2) thus allowing the chondroitin sulfate rich region to diffuse out from the cartilage aggregate. In this embodiment, because the chondroitin sulfate molecules are directly cross-linked to one another, unassociated with an aggrecan or other proteoglycan molecule, they cannot be cleaved or carried away as in normal cartilage.

Nonetheless, a tyramine cross-linked T-HA network (having an HA backbone chain with attached aggrecan molecules, which in turn include chondroitin sulfate chains) may be preferred because of the high availability of HA. This may be beneficial in the case of cartilage replacement or repair using the present invention, because the body's normal metabolic pathway for generating cartilage may be able to build directly onto an implanted tyramine cross-linked T-HA network as will be described.

One further particular application where a cross-linked network according to the invention will have substantial utility is in the production of an artificial kidney. The kidney filters blood by two mechanisms: one is by size exclusion and the second is by charge exclusion. MEMS devices have been designed for use in artificial kidney devices, which contain precisely defined micropores that can effectively mimic only the size exclusion characteristics of the kidney. In a healthy kidney, the charge exclusion related filtration is the result of heparan sulfate proteoglycans present in a basement membrane, which separates two distinct cell types important for other kidney related functions. To mimic this charge barrier in the MEMS engineered artificial kidney, hydrogels can be prepared composed of either heparan sulfate or heparin that are cross-linked via dihydroxyphenyl (dityramine) links as described herein and provided within the pores of the MEMS device. This heparin/heparan sulfate hydrogel can then be sandwiched between two hyaluronan derived hydrogels (e.g. T-HA described above) as described herein, and containing one of each of the cell types normally found in a normally functioning kidney. The central heparin/heparan sulfate hydrogel provides the charge exclusion properties for the device. The outer two hyaluronan hydrogel layers provide protection from the immune system and fouling by normal cellular and molecular debris. Inclusion of the two cell types on opposite sides of the filtration barrier provides a cellular component in its normal physiologic orientation.

In another promising application, the hydrogels herein described can be applied in developing an artificial pancreas. A problem in development of an artificial pancreas is the short half life of MEMS engineered glucose sensors due to fouling of the detector electrode in vivo. Coating of the surface of these detectors with a hyaluronan hydrogel (e.g. T-HA) as described herein would permit diffusion of the small molecular weight glucose molecules that they are designed to detect while providing protection from the immune system and fouling by normal cellular and molecular debris.

In summary, it will be evident from the foregoing that macromolecules useful as scaffold materials for formation of hydrogels include but are not limited to polycarboxylates (containing free carboxylate groups), polyamines (containing free primary amine groups), polyphenols (containing free hydroxyphenyl groups) and their copolymers, examples of which have been described above. When polyphenols are used, the first step in preparing the network described above can be omitted because polyphenols already contain multiple or periodic hydroxyphenyl groups. Otherwise, both polycarboxylates and polyamines must have hydroxyphenyl groups added or substituted along their length, preferably via the above-described carbodiimide reaction pathway. The second step in preparing the network is to carry out an enzyme driven dimerization reaction between two hydroxyphenyl groups attached to adjacent macromolecules (whether polycarboxylates, polyamines or polyphenols) in order to provide a cross-linked structure. This step is carried out using a peroxide reagent (preferably hydrogen peroxide) in the presence of a suitable enzyme (preferably HRP) under metabolic conditions of temperature and pH.

In the case of the preferred dityramine cross-linked T-HA network, in the first step the carboxyl groups on high molecular weight hyaluronan (HA) are substituted with tyramine which introduces reactive hydroxyphenyl groups into the HA molecule. This tyramine substitution reaction preferably is mediated by the carbodiimide, 1-ethyl-3-(3-dimethylaminopropyl)carbodiimide (EDC) with the degree of tyramine substitution on HA controlled by the molar ratios and absolute concentrations of tyramine, EDC and HA used in the reaction mix. Excess reagents such as unused tyramine and EDC are subsequently removed by dialysis, allowing isolation and recovery of high molecular weight tyramine-substituted HA (T-HA). The percent tyramine substitution within each T-HA preparation is easily calculated by measuring: 1) the concentration of tyramine present in the preparation, which is quantitated spectrophotometrically based on the unique UV-absorbance properties of tyramine at 275 nm (see Example 2 below); and 2) the concentration of total carboxyl groups in the HA preparation, which is quantitated spectrophotometrically by a standard hexuronic acid assay. By this technique, T-HA preparations which contain a percent tyramine substitution of only 4-6% have been routinely synthesized experimentally. At this level of tyramine substitution, the vast majority (preferably at least 60, 70, 80, 90, or 95, percent) of the HA molecule remains chemically unaltered, and therefore biologically functional. From this formulation of T-HA (i.e. 4-6% tyramine substitution) a wide range of biomaterials with a wide range of physical properties can be produced by simply varying the concentration of the T-HA used in the second step of the process.

In the cross-linking reaction, solutions of T-HA are cross-linked to form hydrogels through an enzyme (peroxidase) driven reaction, which catalyzes the formation of a covalent bond between two tyramine adducts on adjacent HA molecules, producing a single dityramine cross-link. The formation of multiple, e.g. hundreds, of these dityramine cross-links per HA molecule result in formation of a stable 3-dimensional scaffold or hydrogel. Addition of very dilute peroxide (preferably $H_2O_2$) is required to initiate the cross-linking reaction as it is the peroxide, not —HA, that is the actual substrate for the peroxidase enzyme. The products of the reaction of the peroxidase enzyme on peroxide are free radicals that are preferentially taken up by the hydroxyphenyl rings of tyramine resulting in the formation of the dityramine cross-links. The dityramine linked structures are fluorescent blue (see Example 2), a property which is used to both image the hydrogels and to quantify the degree of cross-linking within the hydrogels. Since the cross-linking reaction is enzyme driven, the hydrogels can be formed under physiologic conditions, and therefore can be formed in the presence of included cells or bioactive agents, or directly adjacent to living tissue while maintaining cell and tissue viability.

The resulting hydrogels are optically clear with a wide range of physical properties depending on the initial T-HA concentration. For example, hydrogels formed from T-HA solutions of 6.25, 12.5, 25, 50 and 100 mg/ml T-HA have been shown experimentally to have physical properties (rigidity, rheology and texture) of a jelly, a gelatin, a dough, a resilient rubber-like composition (similar to a rubber ball), and a cartilage-like material respectively—see Example 3. These materials have potential applications in a wide range of clinical settings including tissue engineering of both orthopedic (i.e. cartilage, bone, tendon, meniscus, intervertebral disc, etc.) and non-orthopaedic (kidney, liver, pancreas, etc.) tissues, gene and drug delivery, coating of non-biological devices for in vivo implantation (i.e. glucose sensors, artificial hearts, etc.), wound repair, biosensor design, and vocal cord reconstruction.

Advantageous properties of the hydrogels described herein include the ability to: 1) provide easy characterization and quality control; 2) integrate with existing tissue matrices; 3) directly incorporate into newly formed matrices; 4) directly include cells and bioactive factors; 5) maintain biocompatibility; 6) control bioresorption; 7) cast easily into complicated anatomical shapes (see Example 4 below); and 8) exhibit the mechanical properties of native tissues such as articular cartilage.

Current biologically-based surgical procedures for cartilage repair include autologous chondrocyte implantation, drilling, abrasion chondroplasty, microfracture, and mosaic arthroplasty. All these procedures treat only focal articular cartilage injuries, and not cartilage denuded joint surfaces such as seen in severe osteoarthritis and rheumatoid arthritis. Also, they use either cartilage tissue plugs or expanded chondrocytes harvested from the patient to fill cartilage defects. These tissues or chondrocytes are expected to fill the defect by synthesizing entirely de novo material, such as newly synthesized hyaline cartilage, that has integrated with existing cartilage matrices and has the biomechanical properties of normal cartilage. However, such procedures all promote the formation of a reparative tissue (fibrocartilage) rather than true hyaline cartilage with further mechanical damage to fibrocartilage thought to predispose the joint to osteoarthritis. Furthermore, the availability of endogenous cartilage as a repair material is quite limited with its acquisition presenting its own risks and morbidity to the patient. As evident from the foregoing discussion and as will become further apparent based on the following Examples, the synthetic macromolecular networks and resulting hydrogels disclosed herein present practical materials for promising new therapies in patients suffering from cartilage degenerative diseases. The materials are entirely synthesized from commercially available ex vivo reagents and so involve no morbidity to the patient which conventionally would be required to harvest endogenous material. In addition, the hydrogel (particularly T-HA) can be implanted as an effective cartilage substitute in cartilage denuded joints as a direct intervention for patients suffering from cartilage-degenerative diseases because they can be synthesized so as to emulate the behavior of normal, healthy cartilage.

Rather than relying on synthetic or natural materials or on chondrocytes to produce de novo an implantable, synthetic cartilage-like extracellular matrix (ECM), the present inventors initially focused on purifying the molecules that give cartilage its form and structural characteristics, and then minimally modifying these molecules to make a material resistant to biological degradation. While chondrocytes still may be relied on for maintenance of the synthetic ECM provided by the macromolecular (e.g. T-HA) network post-implantation (e.g. chondrocytes can be embedded into the hydrogel materials as described above), they are not relied on for de novo synthesis. Instead, the basic structure of the synthetic materials described here is modified by cross-linking via a dihydroxyphenyl, preferably dityramine linkage chemistry, to ensure its survival. On further development and experimentation, as will be seen in the following Examples it was discovered that hydrogels can be made from such materials having a wide array of viscoelastic and other physical properties that can be tuned by appropriate and judicious selection of reagent concentrations and cross-linking conditions to approximate or simulate the properties of other native tissues for which it is or may be desirable to provide a synthetic implantable substitute.

As the Examples below demonstrate, the present hydrogels can be prepared having widely varying properties that are suitable for any number of synthetic tissue implantation or augmentation, as well as other clinical applications. As already described, the present materials can be used to repair cartilage defects produced as a result of either injury or disease. Defects due to injury that can be so repaired can be sports- or accident-related, and may involve only the superficial cartilage layer, or may include the underlying subchondral bone. Defects due to disease which can be repaired using the compositions described herein include those resulting from osteoarthritis and rheumatoid arthritis. Whether from injury or disease, such defects may be in either mature or growth plate cartilage. Formulations for hydrogels for synthetic growth plate cartilage may require the inclusion of unsubstituted scaffold material in order to allow for controlled bioresorption of the biomaterial during growth.

Another potential clinical application for treatment of damaged or arthritic joints is as a replacement for synovial fluid. Conventionally referred to as viscosupplementation therapy, this currently involves injection of a solution of uncross-linked HA into a damaged or arthritic joint, which provides sustained pain relief for weeks even though the HA is cleared from the joint in 1-2 days. Use of the T-HA hydrogels described herein should provide an extended benefit due to their longer in vivo persistence compared to uncross-linked HA.

Another field where the hydrogels described herein will be useful is the repair, reconstruction or augmentation of cartilaginous as well as soft tissues of the head and neck. The availability of biomaterials for soft tissue augmentation and head and neck reconstruction has remained a fundamental challenge in the field of plastic and reconstructive surgery. Significant research and investment has been undertaken for the development of a material with appropriate biological compatibility and life span. The outcomes of this research have not been promising. When placed in immunocompetent animals the structural integrity of currently proposed materials has been shown to fail as the framework is absorbed. Furthermore, though conventional synthetic materials offer excellent lifespan, they present certain unavoidable pitfalls. For example, silicones have been fraught with concerns of safety and long-term immune related effects. Synthetic polymers PTFE (gortex) and silastic offer less tissue reactivity but do not offer tissue integration and can represent long term risks of foreign body infections and extrusion. The materials described in this application will be useful to prepare a synthetic soft-tissue scaffold material for the augmentation or repair of soft-tissue defects of the head and neck. In particular, a cross-linked tyramine-substituted hyaluronan (T-HA) hydrogel, which is non-inflammatory, non-immunogenic, and which can be prepared having the appropriate degree of viscoelasticity (see Examples below), could be used as an effective implantable scaffold material. In addition, the unique ability of the preferred enzyme-driven cross-linking chemistry to maintain cell viability permits inclusion of cells such as chondrocytes directly into the hydrogels during formation which can be performed in situ at a defect site. Thus, the need to sculpt or mold an anatomically compatible graft shape to fit a particular defect site is eliminated.

The dityramine cross-linked T-HA network described above has particular utility for producing artificial or synthetic cartilage. The present hydrogel materials can be used, for example, as a novel, biocompatible and biocompliant material to prepare cartilage implants which are frequently used in reconstructive procedures of the head and neck to repair cartilaginous or bony defects secondary to trauma or congenital abnormalities. Applications specific to the ear include otoplasty and auricular reconstruction, which are often undertaken to repair cartilaginous defects due to trauma, neoplasm (i.e., squamous cell carcinoma, basal cell carcinoma, and melanoma), and congenital defects such as microtia. Applications specific to the nose include cosmetic and reconstructive procedures of the nose and nasal septum. Dorsal hump augmentation, tip, shield and spreader grafts are frequently used in cosmetic rhinoplasty. Nasal reconstruction following trauma, neoplasm, autoimmune diseases such as Wegeners granulomatosis, or congenital defects require cartilage for repair. Septal perforations are difficult to manage and often fail treatment. Cartilage grafts would be ideal for these applications, as autologous or donor cartilage is often unavailable. Applications specific to the throat include laryngotracheal reconstruction, which in children usually requires harvesting costal cartilage, which is not without morbidity. Auricular and septal cartilage is often inadequate for this application. Synthetic cartilaginous materials prepared from hydrogels disclosed herein can be synthesized to suit each of the foregoing applications, based on tuning parameters of hydrogel synthesis such as reagent concentration, substitution and cross-linking rates, etc., as evident from the below Examples. Laryngotracheal reconstruction is usually performed for airway narrowing due to subglottic or tracheal stenosis. The etiology may be traumatic (i.e., intubation trauma, or tracheotomy) or idiopathic. Other possibilities include chin and cheek augmentation, and use in ectropion repair of the lower eyelid, in addition to numerous craniofacial applications. It should be noted that these applications may not need cartilage with the exacting mechanical properties of articular cartilage. Inclusion of a cell population or bioactive agents may also be desirable.

The hydrogel materials described herein also can be used for repair and narrowing of the nasal cavity, normally following overly aggressive surgical resection, to prevent the chronic pooling of fluid in the nasal passages that leads to infection and encrustation. Another promising application is in laryngotracheal reconstruction in both children and adults, as a result of laryngotracheal injury due for example to intubation during a surgical procedure such as cardiovascular surgery. Damaged tracheal cartilage at the anterior and posterior portion of the tracheal ring can be replaced with pre-cast hydrogel formed in the shape of an elongated blocked "T" or an inside out canoe, e.g. via methods disclosed below in Example 4. Hydrogels as herein described also can be used:

to provide cricoid ring replacements.

to protect the carotid artery following neck resection for cancer—the hydrogel can be placed between the carotid artery and the skin as a protective barrier for the carotid artery against loss of the skin barrier.

as a protective coating during neuronal repopulation of a resected nerve—often fibrous tissue forms faster than the neuronal repopulation preventing its eventual formation. Placement of the nerve ends within a hydrogel pre-cast tube could exclude fibrous tissue formation from the site of repopulation.

for reconstruction of the mastoid cavity following ablative ear resection normally as a result of ear infection.

for inner ear reconstruction; specifically in place of prosthetic silastic implants for anvil/stapes replacements. The hydrogels can be used to replace natural cartilage used as the top portion of these graphs, or to completely replace these graphs with an entirely hydrogel graph construct.

for repair of soft tissue defects including chin and cheek augmentation, and use in ectropion repair of the lower eyelid, in addition to numerous craniofacial applications.

for cosmetic and reconstructive purposes in sites other than the head and neck, for example use as breast implants for breast augmentation.

as a wound sealant, for example to fill the void left after removal of lymph nodes (i.e. due to cancer) in the breast or neck, to seal the lymphatics and abate uncontrolled fluid drainage into the resection site that may lead to infection and other complications.

In addition to synthetic cartilaginous tissues as described above, the macromolecular network materials described herein and the hydrogels made from them also can be used in other tissue engineering applications to produce other synthetic orthopaedic tissues, including, but not limited to, bone, tendon, ligament, meniscus and intervertebral disc, using similar strategies and methodologies as described above for the synthesis of artificial forms of cartilage. As evidenced in the Examples below, the materials also can be used to make synthetic non-orthopaedic tissues including but not limited to vocal cord, vitreous, heart valves, liver, pancreas and kidney, using similar strategies and methodologies as described above for the synthesis of artificial forms of cartilage.

Another field where the hydrogel materials disclosed herein present promising utility is in certain gastrointestinal applications where it is necessary to treat or prevent the formation of scar tissue or strictures in abdominal or gastrointestinal organs. There already are a number of products at various stages of clinical and FDA approval, which generally are termed 'hydrogels,' that are designed or intended to be useful in the treatment and prevention of scarring and/or stricture formation. The hydrogels of the present invention are superior to these other hydrogels in that the ones disclosed here can be made entirely from non-immunogenic materials as opposed to exogenous materials such as silicones or other synthetic polymers, and they can be cross-linked in situ within a patient. The hydrogel compositions disclosed herein can be used in similar applications as the already known hydrogels are used or intended to be used, including the following:

for treatment of strictures or scarring of the gastrointestinal tract. The treatment involves injection of the hydrogel material at the site of an anticipated stricture to prevent scarring, or at a site of existing stricture after therapy to enlarge the narrowed GI tract to prevent the stricture from reoccurring.

for treatment of esophageal strictures. Esophageal strictures are a common complication of gastroesophageal reflux disease (GERD). GERD is caused by acid, bile and other injurious gastric contents refluxing into the esophagus and injuring the esophageal lining cells. Approximately 7-23% of GERD patients develop an esophageal stricture, or fibrous scarring of the esophagus. Esophageal scarring also can be caused by ablative therapies used to treat Barrett's esophagus. The major complication of such ablative therapies is that the ablative injury extends too deeply into the esophageal wall and results in an esophageal scar or stricture. Esophageal strictures prevent normal swallowing and are a major cause of patient morbidity. The hydrogel materials described herein may be used to treat or prevent esophageal strictures resulting from GERD, Barrett's esophagus, and esophageal ablative therapies.

for treatment of Crohn's disease. Crohn's disease causes strictures or scars that block off or narrow the lumen of the bowel, preventing normal bowel function. The present hydrogels may be useful to treat or prevent such strictures.

for treatment of primary sclerosing cholangitis (PSC). PSC is a rare disease of the bile ducts of the liver. The bile ducts form a branching network within the liver and exit the liver via two main branches that are combined into the common bile duct which drains the liver and gallbladder of bile into the duodenum. The bile ducts are very narrow in diameter, measuring only up to 2 mm normally at their largest most distal portions, and yet they must normally drain liters of bile every day from the liver into the duodenum. Any blockage of these ducts can result in a serious condition known as jaundice, which allows many toxins and especially hemoglobin breakdown products to accumulate in the body. PSC is a scarring or structuring disease of the bile ducts within the liver and in the extrahepatic bile ducts described above that connect the liver to the small intestine. The bile duct strictures of PSC may be treated or prevented with the present hydrogels.

for treatment of chronic pancreatitis. Chronic pancreatitis is a chronic inflammatory disease of the pancreas that may be complicated by scars or strictures of the pancreatic ducts. These strictures block the drainage of pancreatic juice, which normally must exit the pancreas through a system of ducts or drainage conduits into the small intestine. The pancreatic juice contains many digestive enzymes and other elements important to normal digestion and nutrient absorption. Blockage or narrowing of the pancreatic ducts by chronic pancreatitis can results in severe complications in which the pancreas autodigests and forms life-threatening abdominal infections and or abscesses. The pancreatic strictures of chronic pancreatitis may be treated or prevented with the present hydrogels.

for treatment of gallstone-induced bile duct and pancreatic duct strictures. Gallstones are a very common disorder, a principal complication of which is the formation of bile duct and pancreatic duct strictures, which may be treated or prevented with the hydrogels.

for treatment of ischemic bowel disease. The intestines are prone to the formation of scars or strictures when their blood supply is compromised. Compromised blood flow is called ischemia, and can be caused by many pathologies, including cardiovascular disease, atherosclerosis, hypotension, hypovolemia, renal or hepatic disease-induced hypoalbuminemia, vasculitis, drug-induced disease, and many others. The end stage result of all of these etiologies can result in intestinal strictures that block off the bowel and prevent its normal function. The present hydrogels may be used to treat or prevent ischemic bowel strictures.

for treatment of radiation-induced intestinal strictures. Radiation therapy for cancer is associated with numerous morbidities, important among which is intestinal stricture formation. The present hydrogels may be used to treat or prevent radiation-induced intestinal strictures.

In addition to making synthetic tissues, the hydrogels disclosed here also can be used to provide a coating for non-biological structures or devices to be used in surgery or otherwise for in vivo implantation, such as surgical instruments, or ceramic or metal prostheses. Such a coating would provide a barrier between the non-biologic device material and living tissue. The role of hydrogels as a barrier for non-biologic devices includes, but is not limited to: 1) prevention of absorption of macromolecules and/or cells on the surfaces of non-biologic devices, which can lead to protein fouling or thrombosis at the device surface; 2) presentation of a non-toxic, non-inflammatory, non-immunogenic, biologically compatible surface for devices made from otherwise non-biologically compatible materials; 3) compatibility with device function such as diffusion of glucose for a glucose sensor, transmission of mechanical force for a pressure sensor, or endothelization of a vascular graft or stent; 4) enhancement of device function, such as providing a charge barrier to an existing size barrier in a MEMS based artificial nephron; 5) incorporation into non-biologic devices of a viable cell population entrapped within an aqueous, physiologically compatible environment; and 6) inclusion of drugs or bioactive factors such as growth factors, anti-viral agents, antibiotics, or adhesion molecules designed to encourage vascularization, epithelization or endothelization of the device.

Based on the foregoing, the hydrogels of the present invention may be used to provide a non-allergenic coating for a variety of implantable devices including an implantable glucose sensor for management of diabetes. In addition, the hydrogels may be used to provide: a charge barrier for the development of MEMS-based artificial nephrons; an aqueous, physiologically compatible environment in which embedded kidney cells such as podocytes can be incorporated into a MEMS-based artificial nephron design; and a coating for implantable MEMS devices designed for a variety of purposes including, but not limited to, drug delivery, mechanical sensing, and as a bio-detection system.

The disclosed hydrogels, and particularly a hyaluronan-based hydrogel, also may be covalently attached to silicon-based devices, e.g. through first covalent attachment of the primary amine of tyramine to the silicon surface to provide a hydroxyphenyl coated surface chemistry. This may use the same chemistry used to bind DNA that has been modified with a free amine to silicon surfaces. The HA-based hydrogel then is covalently coupled to the hydroxyphenyl coated surface by the same peroxidase driven chemistry used in its preferred cross-linking mode described above.

The hydrogels also can be used for coating non-biologic cardiovascular devices such as catheters, stents and vascular grafts. These would include devices made from materials conventionally not used because of their biological incompatibility, but which have superior design characteristics to those devices currently in use. Bioactive factors could be incorporated into the hydrogels to promote endothelization or epithelization of the hydrogel, and thus of the implanted device.

A particularly promising application mentioned above is in the design and implementation of an implantable artificial glucose sensor for the treatment and management of diabetes. Effective glycemic control requires frequent measurement of blood glucose levels, which currently requires a pin prick (or "finger stick") to obtain a blood sample. There is tremendous clinical interest in a reliable, cost-effective method of blood glucose measurement and in preventing hypoglycemia, which is the cause of most severe life-threatening events. From a technological standpoint, microsensors have been very successful over the last decade in a wide variety of applications. The successful development of a biocompatible long term implantable glucose sensor would significantly impact routine monitoring of glucose levels by diabetic individuals and play a major contributory role in the further development of a bioartificial pancreas.

A design of a sensor for use during cardiovascular surgery has been published, Clark L C, Lyons C, "Electrode system for continuous monitoring in cardiovascular surgery," *Annals of New York Academy of Science,* 102:29-45 (1962). Subsequently, efforts have been directed toward developing and testing an implantable device that could mimic the native glucose/insulin control system. Besides the obvious advantage of serving as part of a bioartificial pancreas, such a system could be coupled with telemetry hardware and thereby give the patient advance warning of hypoglycemia.

Prior work on implantable glucose sensors generally follows one of two approaches. The first involves placing sensors into blood vessels such as the vena cava or the carotid artery. The second involves placing sensors subcutaneously. These sensors may involve a microdialysis probe or more commonly, an amperometric enzymatic-based transducer. It is believed the risk of thrombosis and hematogenous spread of infection mitigate against the long term use of intravascular sensors. While the exact relationship between blood and subcutaneous glucose concentrations is still being investigated, recent work suggests that mass transfer modeling methods can significantly improve the estimates of blood glucose levels that are based on subcutaneous data. Furthermore, there are significant advantages associated with subcutaneous sensors: clinical safety, ease of insertion and removal, ease of coupling these sensors to a telemetry system and cost. There is substantial evidence that subcutaneous placement of a glucose sensor will work and will lead to much longer life of the sensor than if it were to contact blood directly.

However, a major problem in the design of any continuous glucose sensor for clinical use remains the long-term drift of the sensor, usually caused by fouling of the electrode when exposed to human tissue or the gradual loss of enzyme activity. The introduction of various membranes to act as a glucose or a hydrogen peroxide barrier has, in general, improved sensor performance but it has not resulted in long term stability. The much heralded membrane for this purpose, Nafion, rapidly deteriorates when implanted in the body. Introduction of an implant into subcutaneous tissue elicits both acute and chronic inflammatory responses. Together these result in a complexly orchestrated growth of new tissue which ultimately envelops the implant with a foreign body capsule (FBC). In the short term, it is likely that inflammatory cells metabolize glucose and thereby cause artifacts in the glucose readings. When discussing the problems with long-term use of subcutaneous sensors, experts maintain that the diminished response in vivo can be ascribed to the protein or cellular coating around the sensor which interferes with the mass transport of glucose. If suitable covering membranes for the sensor could be provided to exclude interfering substances or control coating or encapsulation with proteins and cells, the excellent performance in vitro may be matched in vivo. The use of the HA-based hydrogels described herein as a coating agent to both minimize the FBC and keep it away from the sensor membrane should prove a useful solution.

The purpose is to control the tissue response to an implantable glucose sensor using a HA-coating on the sensor membrane. A sheath of HA-based hydrogel will give the sensor membrane "breathing space" by preventing proteins and cells from clogging the diffusion of glucose and oxygen into the sensor. Prior experience has indicated that HA and its derivatives are extremely biocompatible and as a consequence are used in situations where the host tissue response needs to be minimized (e.g., in eye implantation surgery). Thus, sensor performance should be enhanced in the long term when HA-based hydrogels are cast around sensor membranes as it relates to the development of an implantable glucose sensor with the long term perspective that such a sensor should result in improved blood glucose monitoring and ultimately improved quality of life for the diabetic population. In addition, the novel cross-linking structure of the HA-based hydrogels herein disclosed will ensure long-term maintenance of such a coating which will provide significant longevity to a subcutaneously implanted glucose sensor.

Still another promising application is in the production of a bioartificial kidney for the treatment of end-stage renal disease (ESRD). The only current treatment options for ESRD patients are renal replacement therapy (all forms of dialysis) and transplantation. Transplantation is limited by the shortage of donor organs, and is complicated by the necessary and expensive life-long use of immunosuppressive drugs. Alternatively, although dialysis can prolong the life of ESRD patients, average life expectancy on dialysis is reduced by 50%, and the remaining quality of life is far from ideal. Repeated vascular access and handling of the patient's blood leads to frequent and sometimes life threatening infections.

The functional unit of the kidney is the nephron. The nephron begins with a filtering structure, the glomerulus, which is of a tuft of capillaries surrounded by epithelial cells (podocytes) and supported by mesenchymal cells (the mesangium). The glomerulus is connected directly to the tubule of the nephron, a long tube lined with a single layer epithelium of polarized cells. The tubule cells function to salvage fluid, electrolytes and nutrients from the filtrate (by both intracellular transport and pericellular movement) concentrating the filtrate into urine. All nephrons connect into the collecting system, a network of epithelial-lined tubes, which has some additional reabsorptive properties, but primarily functions to direct the urine to the bladder. The filtration unit of the nephron, the glomerulus, consists of the endothelial cell of the capillary arteriolar wall, the podocyte surrounding the exterior of the capillary, and the glomerular basement membrane (GBM) sandwiched between the two cell types. The glomerular capillaries are some of the smallest vascular beds in the body, and the glomerular endothelial cells are specialized for their function by being fenestrated to allow direct contact of the blood plasma to the filtration barrier. Although these fenestrated endothelia do restrict the movement of leukocytes and very large molecules into the filtrate, the permselectivity of the filtration barrier is defined by the podocyte and the GBM.

The GBM is a classic basement membrane structure composed of the prototypic molecules: type IV collagen ($\alpha3$, $\alpha4$, $\alpha5$ heterotrimers), laminin (Laminin-11, $\alpha5$, $\beta2$, $\gamma1$ heterotrimers), HS proteoglycans (perlecan and agrin) and nidogen (nidogen-1 and -2); as well as several additional ECM molecules including, collagen V, fibronectin, a CS proteoglycan (bamacan) and several small leucine-rich proteoglycans (biglycan, decorin, podocan). The GBM is synthesized by both the endothelial cell and the podocyte. Each cell produces a complete basement membrane which subsequently fuses during development to form one, double thickness basement membrane. The GBM has important functions in providing the appropriate microenvironment and substrata for the podocytes and endothelial cells. Without a normal GBM, both cell types lose their typical morphology and cellular differentiation characteristics, which subsequently destroys glomerulus function. The GBM also functions in filtration by restricting the movement of water and has some contribution to the size and charge selectivity, however, the majority of permselectivity is dictated by the podocyte.

The podocyte is a highly specialized epithelial cell and has unique function in the glomerulus. The podocyte extends lamellipodia that wrap around the capillaries, branching into very fine interdigitations with other podocytes. On cross section, these interdigitated cellular extensions are called foot processes (FP) and the spaces between the FPs, where filtration occurs, are called slits. The podocyte synthesizes a macromolecular structure that spans the slit, the slit diaphragm (SD), which forms a bridge between two adjacent FPs. The molecular composition and structure of the SD is not fully understood. The SD appears to be a modified adherens junction containing additional podocyte-specific proteins, the most notable being nephrin. Nephrin extends from the plasma membrane of one FP and forms a homodimeric interaction with another nephrin molecule extending from the adjacent FP, creating a zipper-like structure when viewed in cross section by electron microscopy. How the SD and nephrin function as a permselective barrier is not known, but is currently a very active area of research.

Biological microelectromechanical systems (bioMEMS) are a promising area of exploration for development of next generation bioartificial kidneys. Drug delivery systems, immunoisolators, and capillary networks, as well as precise control of cell differentiation and growth have been demonstrated for bioMEMS. The kidney is the first organ for which chronic substitutive therapy has been accepted, and application of the bioMEMS toolkit to treatment of ESRD is both evolutionary in the technology and revolutionary in the end product. Silicon micromachining technology has evolved such that structures with feature sizes on the order of 1-100 nanometers can be reliably produced in quantity. These dimensions are on the order of those for the glomerular slit diaphragm. The facility with which standard silicon bulk and surface micromachining technology permits microfluidic control, patterned deposition of cells and extracellular matrix proteins, and immunoisolation of cells, lends itself to tissue engineering of artificial organs. The engineering of nanoscale semiconductor filtration membranes could permit independent control and investigation of charge-size selectivity with the potential to lead to the tissue engineering of a bioartificial glomerulus and eventually a complete nephronal unit.

One of the first components in the miniaturization of a bioartificial kidney is development of a nanofabricated hemofiltration membrane (NHM) from bioMEMS components. The NHM is intended to serve the hemofiltration function of the glomerulus in the nephron-like devices of a bioartificial kidney. NHM arrays can be fabricated using standard silicon micromachining techniques containing slit pores of approximately the dimensions of the glomerular slit diaphragm, and conducted experiments to demonstrate its size barrier characteristics similar to those of the glomerular basement membrane. The chemistries and hydrogels described in this patent application can be used to provide two additional and necessary components to the filtration characteristics of the NHM that are required for glomerular function. The first is a charge barrier component similar to those of the glomerular basement membrane. This would be provided by application of a layer of heparan sulfate (HS) based hydrogel. HS is a type of GAG similar to HA and CS. The second addition is inclusion of the podocytes, which are responsible for the majority of the filtration function of the glomerulus through the slit diaphragm. The podocytes would be applied to the surface of the HS-based hydrogel layer in a HA-based hydrogel layer, which would also serve to provide a layer of biocompatibility. The presence of the HS layer should facilitate proper matrix-cell interactions and stimulate the deposition of an appropriate basement membrane.

The hydrogels described herein, including but not limited to tyramine-based hyaluronan hydrogels, also can be used as research and clinical reagents. One promising application is controlled or extended release drug delivery. In this application, the drug can be trapped within a sphere or other suitable shape of hydrogel material composed of a central spherical or other shaped core of hydrogel formulated at a relatively high macromolecular concentration (and thus lowest porosity), onto which concentric spherical layers of hydrogel are coated, each successively coated layer being formulated of a progressively lower macromolecular concentration (and thus higher porosity). Release of the drug is then controlled by the rate of hydrogel degradation if so engineered, binding of the drug to the hydrogel scaffold and diffusion of the drug through the scaffold pores. The hydrogel sphere then is implanted into a patient at an appropriate location to effect extended release of the drug.

Targeted drug deliver also can be achieved through an affinity-based strategy based on designed affinity of drug laden hydrogel particles to specific tissue and cell types. To this end, the hydrogels can be used as an affinity-based medium for the selective binding and thus purification of specific cell populations through incorporation of targeted cell binding molecules within the hydrogels during or prior to cross-linking. Once a select cell population is bound to the hydrogel affinity-based medium they could be released for further investigation, or directly entrapped while bound to the hydrogel affinity-based medium into other formulations of the hydrogels for other tissue engineering or clinical applications.

Such an affinity-based medium also can be used for the selective binding and purification of hyaluronan binding proteins. As the entire medium can be made solely of hyaluronan with no other support material background binding should be quite low. By using other materials as the scaffold material (such as aggrecan) other affinity-based media can be prepared for purification of molecules that selectively bind to those scaffold materials.

Such an affinity-based medium also can be used for selective binding and purification of specific macromolecules or cell populations through incorporation of protein A within the hydrogels during cross-linking. Antibodies specific to the macromolecule or cell population of interest can then be used to coat the protein A infused hydrogels with the antibodies optimally oriented with their antigen binding ($F_{ab}$) arms directed outward and their constant ($F_c$) domain bound to the protein A. Once a select cell population or macromolecule is bound to the protein A hydrogel, it could be released for further investigation, or directly entrapped while bound to the protein A hydrogel into other formulations of the hydrogel for other tissue engineering or clinical applications. Alternatively antibody could be directly incorporated into the hydrogels.

The disclosed hyaluronan-based hydrogel materials also have utility as a diagnostic for the presence of hyaluronidases which can be predictive of the metastatic potential of certain cancers; e.g. by coating of a biopsy slide with hyaluronan hydrogel and measurement of the extent and localization of the loss of intrinsic fluorescence of the hydrogel material due to its dityramine cross-links as the hydrogel is digested by endogenous hyaluronidases. By using other materials as the scaffold material (such as aggrecan) other degradative enzymes could be detected such as metaloproteinases.

Further aspects of the invention will be understood in conjunction with one or more of the following examples, which are provided by way of illustration.

EXAMPLES

Example 1

Experimental quantities of tyramine-substituted hyaluronan hydrogels having dityramine cross-links according to the invention have been prepared as follows. HA is dissolved at 1 mg/ml based on hexuronic acid in 250 mM 2-(N-morpholino) ethanesulfonic acid (MES), 150 mM NaCl, 75 mM NaOH, pH 6.5 containing a 10-fold molar excess of tyramine relative to the molar concentration of HA carboxyl groups. Tyramine substitution onto the carboxyl groups is then initiated by the addition of a 10-fold molar excess of EDC relative to the molar concentration of the HA carboxyl groups. A 1/10th molar ratio of N-hydroxysuccinimide (NHS) relative to the molar amount of EDC is added to the reactions to assist the EDC catalyzed amidation reaction by formation of active esters. Reactions are carried out at room temperature for 24 hours, after which the macromolecular fraction is recovered from unreacted small molecular weight reactants such as tyramine, EDC, NHS, and MES by exhaustive dialysis versus 150 mM NaCl and then ultrapure water followed by lyophilization. After lyophilization, the tyramine-substituted HA (T-HA) product is dissolved to working concentrations of between 5 and 100 mg/ml in PBS (which is a buffer compatible with cell suspension, in vivo tissue contact, and the cross-linking reaction) to provide various concentration preparations depending on the desired rigidity of the final hydrogel. Alternatively, the solvent can be any other suitable solvent besides PBS that will not substantially negatively impact the enzyme activity and that will not interfere with cross-linking reaction via selective uptake of free radicals generated by the enzyme. Suitable alternative solvents include water, conventional biological tissue culture media, and cell freezing solution (generally composed of about 90% blood serum and about 10% dimethyl sulfoxide). Prior to suspension of cells (see Example 5) or contact with tissues in vivo, the T-HA should be filtered through a 0.2 μm filter. Next, tyramine-tyramine linking is carried out by adding 10 U/ml of type II horseradish peroxidase (HRP) to each T-HA preparation. Cross-linking is initiated by the addition of a small volume (1-5 μl) of a dilute hydrogen peroxide solution (0.012%-0.00012% final concentration) to yield the final hydrogel with desired rigidity. For preparation of larger quantities or volumes of a desired hydrogel, quantities of reagents provided in this paragraph could be scaled up appropriately by a person of ordinary skill in the art.

Example 2

An experiment was conducted to determine the degree of tyramine substitution (and consequent dityramine cross-linking) for a T-HA macromolecular network according to the invention. Initially, three formulations of (uncrosslinked) tyramine-substituted hyaluronan (T-HA) were prepared as described above, designated 0×, 1× or 10×. The 0× formulation was prepared using no EDC (i.e. containing no carbodiimide), meaning there was no carbodiimide present to mediate the reaction for creating an amide bond between the $NH_2$ group on tyramine and a $CO_2H$ group on the HA molecules. Thus, the 0× formulation can be considered a control. The 1× formulation contained a 1:1 stoichiometric ratio of EDC based on the quantity of $CO_2H$ groups present on the HA molecules in the reaction mixture. The 10× formulation contained a 10:1 stoichiometric ratio (or 10-fold excess) of EDC based on the quantity of $CO_2H$ groups present on the HA molecules in the reaction mixture. In all three formulations, a stoichiometric excess of tyramine was provided relative to the quantity of $CO_2H$ groups on HA. In all three formulations (0×, 1× and 10×) the reactants and the appropriate amount of EDC for the formulation were combined in a vial and agitated to facilitate the tyramine-substitution reaction. All three formulations were allowed to react for 24 hours at room temperature, after which the vial contents were dialyzed to remove unreacted tyramine molecules, EDC and acylurea (EDU) byproducts of the reaction. These molecules were easily separated from HA and any formed T-HA molecules through dialysis due to the relatively small size of tyramine, EDC and EDU compared to macromolecular HA. Once unreacted tyramine and EDC were removed, the remaining contents for each formulation were analyzed to determine the rate of tyramine substitution relative to the total number of available $CO_2H$ sites present on HA molecules.

Tyramine exhibits a UV absorbance peak at 275 nm, making the degree of tyramine substitution easily detectable against a tyramine calibration curve. Based on UV-spectroscopic analysis of the above three T-HA formulations, it was discovered that the HA-tyramine substitution reaction carried out with no EDC present (formulation 0×) resulted in substantially zero tyramine substitution onto the HA molecules. This confirmed the importance of using a carbodiimide reaction pathway in the tyramine substitution reaction. However, the tyramine absorption in the T-HA formulation prepared using a 1:1 EDC:$CO_2H$ stoichiometric ratio in the tyramine substitution reaction (formulation 1×) resulted in a tyramine substitution rate of about 1.7% relative to all available $CO_2H$ groups on the HA chains. The 10× formulation (10:1 EDC:$CO_2H$ ratio) resulted in about a 4.7% substitution rate.

Subsequently, hydrogen peroxide and horseradish peroxidase (HRP) were added to each of the three dialyzed HA/T-HA formulations (0×, 1× and 10×) at 5 mg/mL and the resulting formulations were allowed to react to completion. After reaction in the presence of peroxide and HRP, it was observed that the 0× formulation remained entirely liquid, having a strong meniscus; no gel formation was observed, confirming the fact that no or substantially no tyramine substitution had occurred when no EDC was used in the tyramine substitution reaction. For the 1× formulation, only a very weak meniscus was observed and the contents of the vial had gelled, confirming that both tyramine substitution and cross-linking had occurred. For the 10× formulation, a relatively rigid gel had formed, and in fact had shrunk relative to the initial volume of fluid in the container, leaving a quantity of liquid (having a meniscus) on top. The gel prepared from the 10× formulation (having a 4.7% tyramine substitution rate) was much firmer and more rigid than that from the 1× formulation having a 1.7% tyramine substitution rate.

The dityramine structure exhibits a blue fluorescence on exposure to UV light. The products of each of the above formulations were exposed to UV light to detect the presence of dityramine cross-links; As expected, both the 1× and 10× hydrogels exhibited blue fluorescence (the 10× hydrogel fluorescence being more intense than that of the 1× hydrogel), while the 0× formulation exhibited no blue fluorescence at all. This confirmed the presence of dityramine cross-links in both hydrogels, and that the occurrence of dityramine in the more rigid hydrogel (10×) was greater than in the less rigid hydrogel (1×).

The overall result was that the importance of the carbodiimide-mediated reaction pathway was demonstrated, and it was confirmed that the relative rigidity of a hydrogel formed from a cross-linked T-HA network is proportional to the degree of dityramine cross-linking, which is in turn proportional to the degree of tyramine-substitution onto HA. It was quite a surprising and unexpected result that even a 1.7% tyramine-substitution rate (and subsequent cross-linking rate to form dityramine links) provided a suitably firm T-HA gel (or hydrogel). A 4.7% substitution (and cross-linking) rate resulted in even a firmer T-HA gel. Also surprising was that a ten-fold stoichiometric excess of carbodiimide (EDC) relative to the quantity of carboxylic acid groups present in the reaction mixture (formulation 10×) resulted in only about a 4.5-4.7% tyramine substitution rate, yet stable and cohesive tyramine cross-linked T-HA networks were nonetheless achieved.

This means that the majority of the carboxylic acid groups on the HA molecules are unsubstituted and not tyramine cross-linked, essentially remaining the same as in the native HA molecule, yet the resulting network is a cohesive and stable hydrogel. Therefore, when used as a cartilage substitute in vivo, because a majority of the HA molecules in the invented T-HA network or gel are essentially unaltered compared to HA in normal cartilage, it is believed that the body's native metabolic pathways (aided or unaided by cells provided within the T-HA network) may recognize the invented network as native biologic material, and will be able to carry out ordinary synthesis and metabolism functions with respect thereto. In addition, it is noted that HA is a highly ubiquitous material in the body, and is non-immunogenic in humans. As a result, the cross-linked macromolecular network, comprised a majority of unaltered native HA, will have substantial application in a wide variety of tissue engineering applications where it is desirable or necessary to provide synthetic tissue in a human body. This represents a significant advance over the state of the art. Therefore, quite surprisingly, a high degree of tyramine substitution, e.g. greater than about 10-20%, may be undesirable; the above described experiments demonstrated that such high degrees of substitution are unnecessary to provide a suitable T-HA network. Preferably, a dihydroxyphenyl (e.g. dityramine) cross-linked polycarboxylate (e.g. HA) network has a hydroxyphenyl (tyramine) substitution rate of less than 50, preferably less than 40, preferably less than 30, preferably less than 20, preferably less than 15, preferably less than 10, preferably less than 9, preferably less than 8, preferably less than 7, preferably less than 6, preferably less than 5, percent based on the total quantity of $CO_2H$ groups present on the polycarboxylate (HA) molecules.

Example 3

Conventionally, it has been believed that natural cartilage exhibits its viscoelastic properties and its ability to resist deformation and absorb compressive loads principally as a result of the repulsive forces between negatively charged $SO_4^{2-}$ groups on adjacent chondroitin sulfate chains present in the aggrecan matrix. An experiment was performed to determine the efficacy of various macromolecular networks within the scope of the invention to resist deformation and absorb compression compared to natural cartilage. In particular, three such networks were prepared, respectively, composed of the following: 1) dityramine cross-linked HA molecules (T-HA); 2) dityramine cross-linked chondroitin sulfate molecules in the form of aggrecan (T-Aggrecan); and 3) a composite material composed of 50% T-HA and 50% T-Aggrecan. Formulations of uncross-linked T-HA and T-Aggrecan were prepared and purified as in Example 1, each having a tyramine substitution rate of about 5%. From these T-HA and T-Aggrecan formulations, five different concentrations of the T-HA alone, T-Aggrecan alone and a 50:50 mixture of T-HA and T-Aggrecan were prepared:

Concentration 1: 6.25 mg total T-GAG/mL water
Concentration 2: 12.5 mg total T-GAG/mL water
Concentration 3: 25 mg total T-GAG/mL water
Concentration 4: 50 mg total T-GAG/mL water
Concentration 5: 100 mg total T-GAG/mL water.

The notation T-GAG is used herein to embrace both T-HA and T-Aggrecan. Though aggrecan technically is not a glycosaminoglycan (GAG), for purposes of this example T-GAG nonetheless is defined to embrace both T-HA and T-Aggrecan hydrogels. Each of the above preparations was then reacted in the presence of hydrogen peroxide and horseradish peroxidase, also as in Example 1, to form dityramine cross-links between the T-GAG molecules and provide respectively Hydrogels 1, 2, 3, 4 and 5 for each of the three material compositions. Each of the fifteen hydrogels (five concentrations for each of the three material compositions) was found to be a stable and substantially coherent material with the physical properties of each hydrogel varying relative to the concentration of T-GAG in the preparation from which it was made. For example, qualitatively T-HA Concentration 1 resulted in T-HA Hydrogel 1 having rigidity and rheological properties comparable to that of Vaseline or jelly; the hydrogel was stable and coherent yet could be caused to flow or spread on application of an external force, e.g. from a spatula or other conventional tool. T-HA Hydrogel 1 exhibited excellent adhesive properties making it an ideal candidate for a nonallergenic coating material for surgical instruments during surgery, e.g. ophthalmologic surgery. T-HA Hydrogel 2 was more rigid than T-HA Hydrogel 1 due to the greater concentration of T-HA in the preparation from which it was made, and the consequent predicted decrease in intramolecular cross-linking and increase in intermolecular cross-linking associated with increased T-HA concentration. T-HA Hydrogel 2 exhibited rheological and rigidity properties characteristic of gelatins, with a degree of viscoelastic reboundability on external loading. On greater loading, T-HA Hydrogel 2 was found to break up into smaller pieces instead of flowing, also characteristic of a gelatinous material. T-HA Hydrogel 3 had the properties and consistency of a dough or malleable paste, also not flowing on application of an external loading force. This material also exhibited substantially greater viscoelastic properties compared to T-HA Hydrogels 1 and 2. T-HA Hydrogel 4 was a highly rigid and coherent gel that strongly resisted breaking up on application of an external loading force. T-HA Hydrogel 4 was a highly resilient rubber-like composition that actually generated substantial springing force upon sudden compression (e.g. dropping onto the floor). This ability of T-HA Hydrogel 4 to generate such a springing force in response to a sudden compression may make this material ideal for certain joint replacement/repair applications where the joint undergoes repeated and periodic compressional loading (e.g. the ankle joint). In addition to the properties described for T-HA Hydrogel 4, T-HA Hydrogel 5 had cartilage-like properties with both the appearance of articular cartilage and the feel of cartilage upon cutting with a surgical blade.

Confined compression tests were performed to quantitatively determine the compressive mechanical properties of the fifteen different hydrogels. A custom built polycarbonate confining chamber, and porous polypropylene filter platen (20 μm pores, 20% porosity) were used to perform the confined compression testing. Five cylindrical plugs (7.1 mm in diameter, approximately 3 mm in thickness) at each hydrogel concentration for each of the three material compositions were made using the confining chamber and the freeze-thaw technique described in Example 4 below. The following testing protocol was followed for a series of stress relaxation tests in confined compression. All testing was performed using an Instron 5543 machine under computer control, which recorded the time-displacement-load data at a frequency of 10 Hz. A ±5 N or ±50 N load cell (Sensotec) was used to monitor load throughout each test. A step of 30 μm (30 μm/sec), representing 1% strain, was applied until the sample reached equilibrium. This was defined as a relaxation rate that slowed to less than 10 mN min$^{-1}$, at which time the next step was automatically started, until 20 cycles (representing approximately 20% strain) were completed. The thickness of each sample tested in confined compression was determined mechanically, by measuring the displacement at which the compressive response initiated relative to the bottom of the chamber as measured with the Instron 5543 machine. The measured thickness was used to calculate the strain percentage for each step.

Figure 4B:
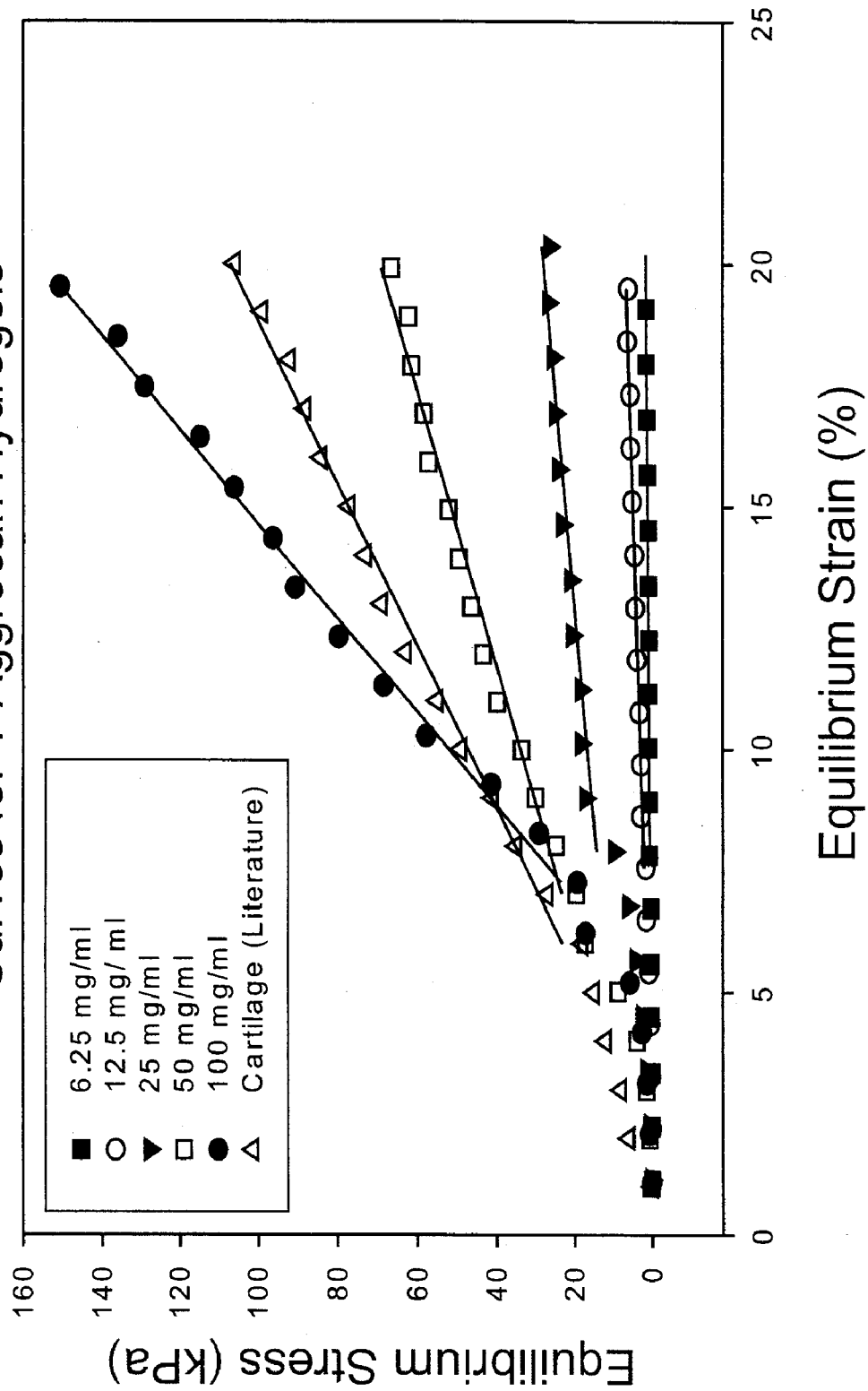
FIGS. 4a-4c are graphs showing comparative results for mechanical testing in a confined compression test (equilibrium stress versus applied strain) of T-HA (FIG. 4a), T-Aggrecan (FIG. 4b) and 50% T-HA/50% T-Aggrecan composite (FIG. 4c) hydrogels according to the invention versus published results for articular cartilage plugs (Example 3). The relationship between glycosaminoglycan (GAG) concentration and material compressive strength is shown in FIG. 4d.
Figure 4C:
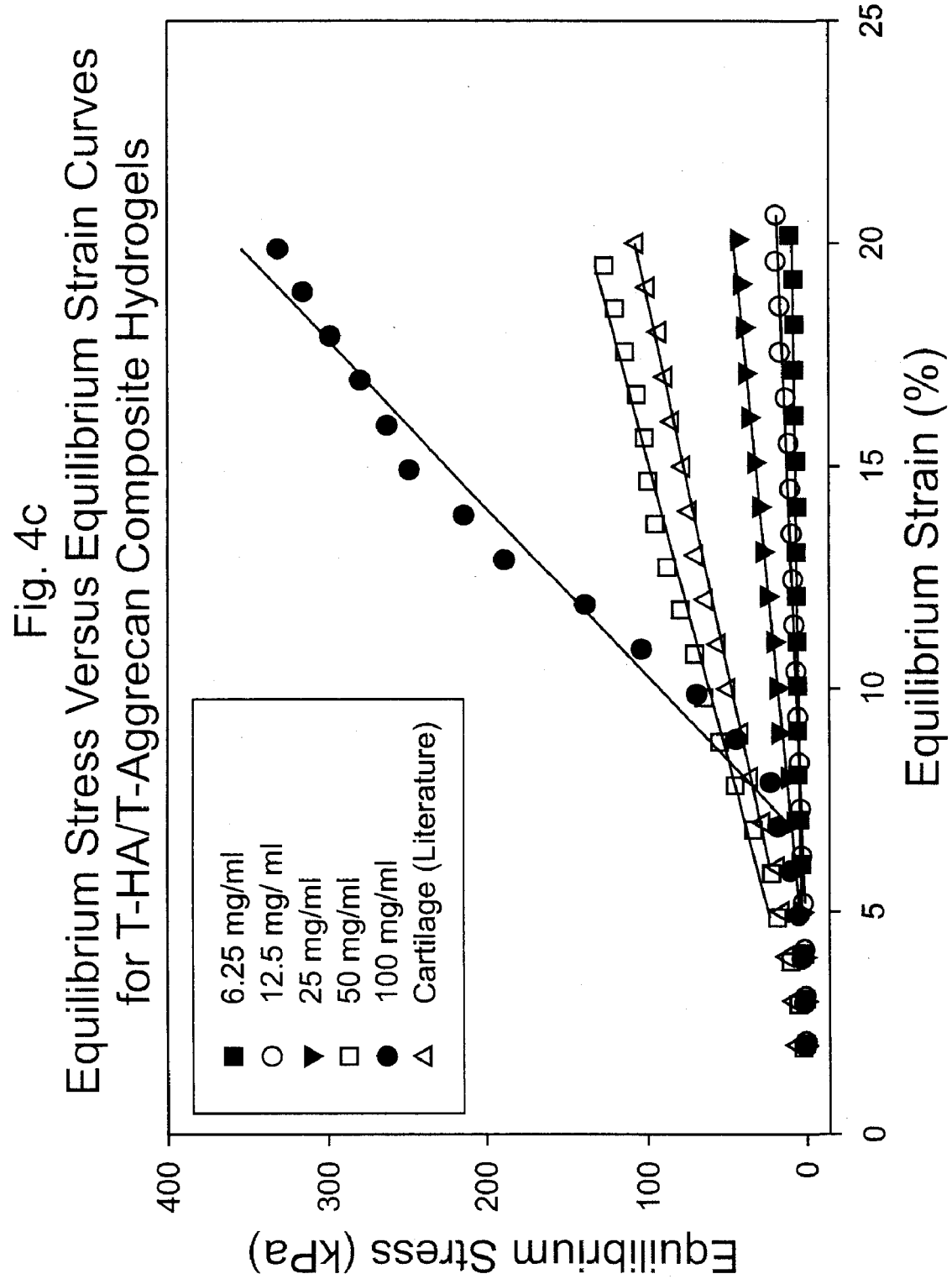

The compressive mechanical properties of the fifteen hydrogels were determined as described in the preceding paragraph. Load data was normalized by sample cross-sectional area (39.6 mm$^2$) to compute stress. The equilibrium stress was plotted against the applied strain for each material formulation. The aggregate modulus at each step was defined as the equilibrium stress divided by the applied strain. For each material, the aggregate modulus was defined as the slope of the equilibrium stress-strain data in the most linear range. FIGS. 4a, 4b and 4c display the equilibrium compression behavior for the five concentrations of T-HA, T-Aggrecan and 50:50 T-HA/T-Aggrecan composite hydrogels, respectively. All fifteen hydrogels were testable in confined compression, and demonstrated characteristic stress relaxation responses typical of biphasic materials (such as cartilage). The aggregate moduli for the 6.25 mg/ml and 12.5 mg/ml T-GAG hydrogels were 1-2 orders of magnitude lower than articular cartilage. The 25 mg/ml T-GAG hydrogels, as well as the 50 mg/ml T-aggrecan hydrogel, displayed aggregate moduli on the order of, but at least 30% lower than that of articular cartilage. All the 100 mg/ml T-GAG hydrogels, as well as the 50 mg/ml T-HA and the all the composite hydrogels, displayed aggregate moduli, equal to or exceeding reported literature values for articular cartilage. These data demonstrate the ability to characterize hydrogels using standard mechanical assays, and to generate hydrogels with similar mechanical properties to a wide variety of tissues including that of articular cartilage, using a variety of glycosaminoglycans as the hydrogel scaffold material.

The aggregate moduli for the five concentrations of the T-HA, T-Aggrecan and composite materials composed of 50% T-HA and 50% T-aggrecan are summarized below in Table 1.

TABLE 1

| | Aggregate Modulus (MPa) | | |
|---|---|---|---|
| | HA (n = 5) | Aggrecan (n = 5) | 50/50 Composite (n = 5) |
| 6.25 mg/ml | *0.024 ± 0.014 | *0.008 ± 0.003 | 0.064 ± 0.019 |
| 12.5 mg/ml | 0.072 ± 0.024 | *0.032 ± 0.006 | 0.108 ± 0.004 |
| 25 mg/ml | 0.482 ± 0.131 | 0.111 ± 0.021 | 0.277 ± 0.021 |
| 50 mg/ml | 1.023 ± 0.164 | 0.366 ± 0.065 | 0.754 ± 0.071 |
| 100 mg/ml | 1.241 ± 0.351 | 0.748 ± 0.179 | 2.850 ± 0.377 |

*(n = 3)

Figure 4D:
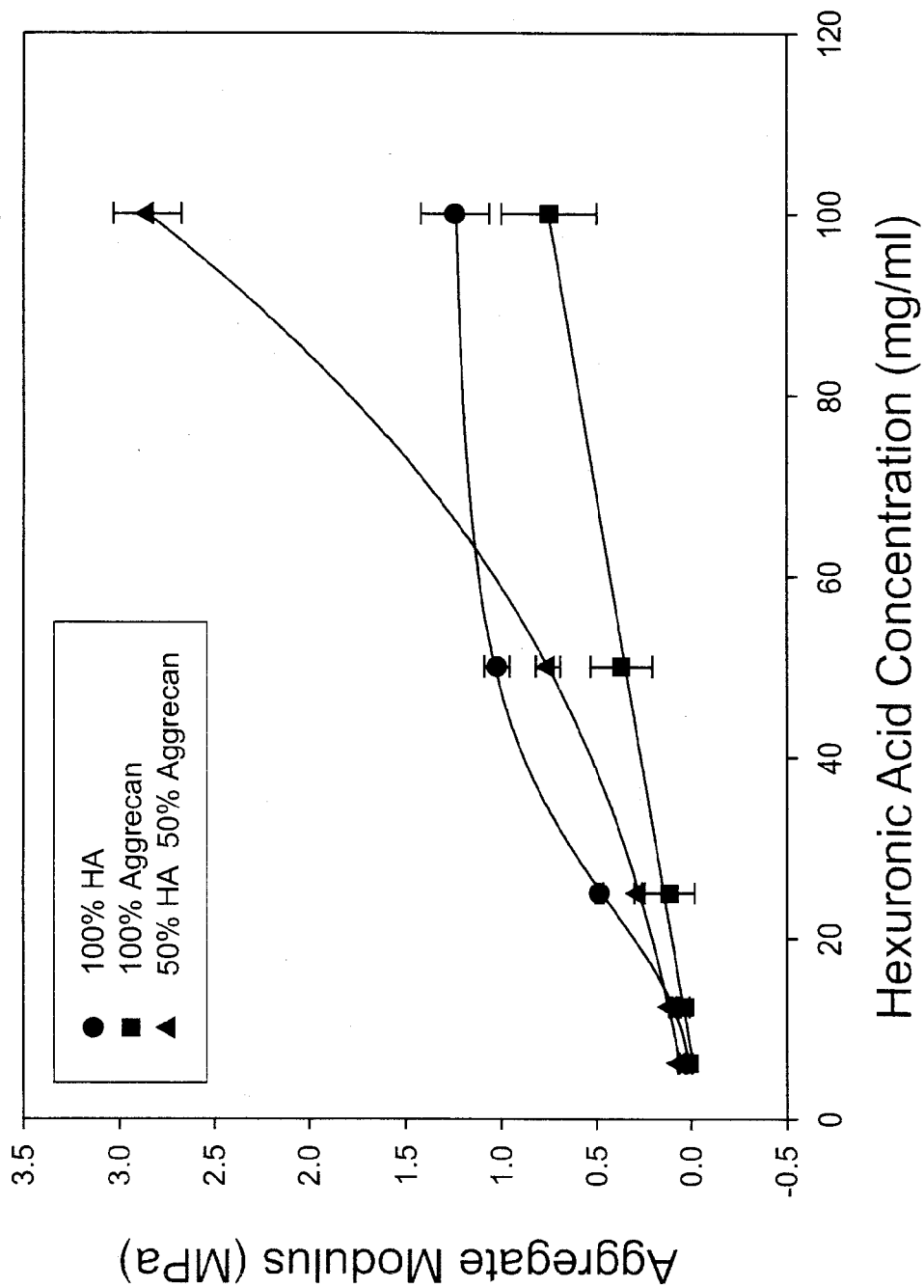

FIG. 4d shows the measured aggregate modulus as a function of concentration for the T-HA, T-Aggrecan and composite hydrogels. As the concentration of the T-HA hydrogels increases, a plateau is reached for the aggregate modulus while the T-Aggrecan hydrogels display a linear relationship. Interestingly, the composite hydrogels show a relationship indicative of an exponential increase in compressive properties as concentration increases. This indicates that the moduli of other hydrogel materials can be predicted by further exploring and modeling these relationships.

Based on the above experiments it was surprisingly and unexpectedly discovered that a dityramine cross-linked GAG network (HA or aggrecan) will produce a coherent hydrogel material whose rigidity and other physical (rheological) properties can be tuned by varying the T-GAG concentration prior to cross-linking the tyramine groups to suit a particular application. The coherence and elastic properties of these hydrogels was observed even absent any (or substantially any) $SO_4^{2-}$ groups in the network to supply the charge-to-charge repulsive forces to generate the material's compression resistance and elasticity. This was a highly surprising and unexpected result with substantial positive consequences in tissue engineering applications. Hyaluronan is a highly ubiquitous and non-immunogenic molecule found in humans. Therefore, hydrogels comprised of dityramine cross-linked hyaluronan networks can be used to provide suitable tissue replacement materials that can be implanted within a human body, whose rigidity can be tuned based on the application as evidenced by this example. As these materials can or will be composed of predominantly unaltered hyaluronan which is non-immunogenic, the hydrogels should result in zero or substantially zero immune response. This is an important advantage over many conventional tissue engineered materials whose formation chemistries prevent their application in vivo due to harsh reaction conditions or reagents, and whose final chemical structures are more likely to induce an immune response.

Example 4

A number of methods of preparing hydrogels such as those described in Example 3 have been developed to cast or form the hydrogel into a predetermined three-dimensional shape. This is important for myriad tissue engineering applications where it is necessary to provide artificial tissue material to fill a native tissue defect or void within a patient. A first method is to employ an in situ forming technique where the hydrogel is formed in place, i.e. in position and in the shape of its final application and structure. The in situ formation method has been carried out experimentally as follows. Tyramine-substituted hyaluronan (T-HA) was prepared via the carbodiimide-mediated pathway described herein. Following dialyzation to remove unreacted tyramine, EDC, NHS, etc., and dissolution at the desired concentration in PBS (see Example 1 above), a small quantity of horseradish peroxidase enzyme was added to the T-HA liquid preparation to form a first solution. This first solution was provided into a laboratory container (to simulate an in vivo situs) having a specific interior geometry. Subsequently, a second solution was prepared containing very dilute hydrogen peroxide (0.012%-0.00012% final concentration). A small volume of this second solution relative to the first solution was then injected into the container already containing the first solution to initiate the dityramine cross-linking reaction to yield the hydrogel. Hydrogels prepared by this technique have been prepared having varying rigidity and rheological properties as described above in Example 3, and conformed well to the interior surface contour of the container in which they were formed. Because the principal reagents ($H_2O_2$, hyaluronan and peroxidase) are either non-allergenic or diffusible molecules, and because the cross-linking reaction proceeds under metabolic conditions of temperature and pH, this technique can be performed in vivo at a surgical situs in a patient as a surgical procedure to produce a defect-conforming hydrogel. This method is particularly attractive for reconstructive facial surgery in which the uncross-linked T-HA preparation (with peroxidase) can be injected and manipulated subcutaneously by the surgeon to produce the desired facial contours and then the hydrogel subsequently cross-linked by injection of a small volume of the hydrogen peroxide solution.

A second method is a porous mold technique and is suitable for forming hydrogels into more complex three-dimensional structures. In this technique a porous hollow mold is first cast conforming to the shape and contour of the intended final structure. For illustration, a mold can be prepared having an interior surface in a cuboid shape if a cuboid shaped hydrogel were desired. The mold can be prepared or cast via conventional techniques from conventional porous materials, e.g. plaster of paris, porous or sintered plastics or metals, etc. In a particularly preferred embodiment the mold is prepared using a cellulosic dialysis membrane. The first and second solutions are prepared as above, and the first solution is provided into the hollow mold cavity of the porous mold. Subsequently, the now-filled mold is submersed in a bath of very dilute peroxide. The macromolecular T-HA and peroxidase molecules are unable to diffuse out of the porous mold due to their size, however the very small peroxide molecules ($H_2O_2$) are able to diffuse in and react in the presence of the peroxidase enzyme to yield dityramine cross-links. It is inherent in this method that cross-linking occur from the outside inward to produce the finished hydrogel shape, and a certain degree of trial and error may be required to determine optimal or sufficient immersion times in the peroxide bath. Determination of these time periods is within the skill of a person having ordinary skill in the art. Successfully completed three-dimensional hydrogel shapes have been prepared in laboratory bench experiments via this porous mold technique.

A third method is a freeze-thaw technique that is suitable for casting hydrogels according to the invention in highly intricate predetermined three-dimensional shapes, e.g. having internal folds such as a human ear. In this technique, a mold is prepared from a soft or malleable material such as a polymeric material having a low glass transition temperature, e.g. below −80° C. The preferred mold materials are silicones having low glass transition temperatures, such as polydimethylsiloxane whose glass transition temperature is about −127° C., however other suitably low glass transition (e.g. below −80° C.) silicones, as well as other polymers, can be used. The silicone (preferred material) is first prepared such that it has an inner mold cavity conforming to the surface shape, contour and volume of a desired hydrogel part via any conventional or suitable technique (i.e. press-molding, carving, etc.). First and second solutions are prepared as above, and the first solution is provided into the inner mold cavity of the silicone mold. The now-filled silicone mold is then cooled to about −80° C. by contacting with solid $CO_2$ (dry ice). Because the first solution is principally water, it freezes into a solid ice form conforming to the shape and contour of the inner mold surface. However, the silicone mold, having a glass transition temperature below −80° C., remains soft and malleable and the solid ice form of the first solution is easily removed. Because the first solution expands as it freezes, suitable mechanical hardware should be used to ensure the silicone mold does not deform or expand as the solution freezes. Preferably, port holes are provided in the mold to allow for expansion and discharge of the first solution as it expands during the freezing process.

Once the solid ice form of the first solution has been demolded, minute defects or flaws in the three-dimensional structure can be repaired by carving with a suitable tool, and more of the liquid first solution can be added to fill surface voids, which liquid instantly freezes on contact with the solid ice form. Also, the ice form can be placed back on the dry ice surface if desired to ensure uniform temperature and freezing of any added first solution material. Once the three-dimensional shape of the ice form has been perfected, it is immersed in a liquid peroxide solution to initiate thawing of the frozen water and dityramine cross-linking from the outside-in. This is possible do to the rapid kinetics of the cross-linking reaction. Cross-linking is determined to be complete once the last remaining frozen water has melted at the center of the forming hydrogel form, which can be easily observed because the forming hydrogel is substantially clear.

Very successful experiments have been performed according to this freeze-thaw technique to produce a solid hydrogel in the shape of a human ear. Other structures that could be formed by this method, such as intervertebral discs, meniscus, etc. will be evident to those skilled in the art. It should be noted in this freeze-thaw technique, the threshold glass transition temperature of −80° C. for the mold material is selected to correspond roughly with the surface temperature of solid $CO_2$ (dry ice), to ensure the mold material does not become brittle when the first solution is frozen to produce the solid ice form. However, if another cooling material, other than $CO_2$ is used, then the threshold glass transition temperature for suitable mold materials may be adjusted accordingly.

For the three methods of hydrogel formation described above, the first solution contained both the peroxidase and T-HA, while the second solution contained the peroxide. While it may be possible to switch the peroxidase and peroxide in the first and second solutions respectively, it is less preferred to provide the peroxide in the first solution with the T-HA. This is because once the peroxide, peroxidase and T-HA are combined, the T-HA rapidly begins to form a cross-linked macromolecular network. If the peroxidase (which is a macromolecular molecule) is not already uniformly distributed with the T-HA it may be unable or substantially hindered from diffusing through the pore structure of the forming hydrogel to facilitate uniform cross-linking throughout the entire T-HA/peroxide solution. The result could be non-uniform and/or incomplete cross-linking of the T-HA and a non-uniform hydrogel. Conversely, the relatively small peroxide molecule (hydrogen peroxide is only one oxygen atom larger than water) can diffuse through the hydrogel pore structure with relative ease, resulting in a uniform hydrogel structure.

In addition, the macromolecular size of the peroxidase allows it to be similarly retained as the T-HA within porous molds that are only porous to small molecular weight peroxides which easily and uniformly diffuse through both the molds and newly forming macromolecular networks (i.e. hydrogels). For these reasons it is preferred to start with the peroxidase uniformly distributed with the T-HA in the first solution, and to provide the peroxide separately in the second solution.

A fourth method is an alternating sprayed or brushed layering technique. The first solution is prepared as described above and contains both the peroxidase and T-HA. However, the second solution not only contains the peroxide as described above, but also T-HA at the same concentration as in the first solution. Then a thin layer of the first solution is applied at the desired location (in situ) followed by an overlying thin layer of the second solution. This procedure is repeated such that alternating layers of the first and second solutions are successively applied until the defect or application situs has been completed. The very thin alternating layers of the first and second solutions promote virtually complete dityramine cross-linking ensuring a highly coherent final hydrogel having the desired rheological properties based on the initial T-HA concentration of the two solutions. The thin nature of the layers is desirable to ensure that free radicals produced by the peroxidase in the first solution layers are able to penetrate completely adjacent second solution layers and complete cross-linking independent of peroxidase diffusion into the second solution layer (see above). T-HA is included in both solutions to ensure uniform T-HA concentration throughout the final hydrogel. This technique has been performed in laboratory bench experiments and has provided contour-conforming and volume-filling coherent hydrogels.

This technique is highly applicable where it is desired to provide a thin, but variable layer of tyramine cross-linked HA, such as on the surface of a denuded osteoarthritic joint in which little if any native healthy cartilage remains in the patient at the implant site.

All four of the above techniques have been described with respect to dityramine cross-linked hyaluronan, however it will be understood that other combinations within the scope of the present invention (other dihydroxyphenyl cross-linked macromolecules, such as polycarboxylates, polyamines, polyhydroxyphenyl molecules and copolymers thereof) can be molded via the above techniques.

Example 5

Figure 5:
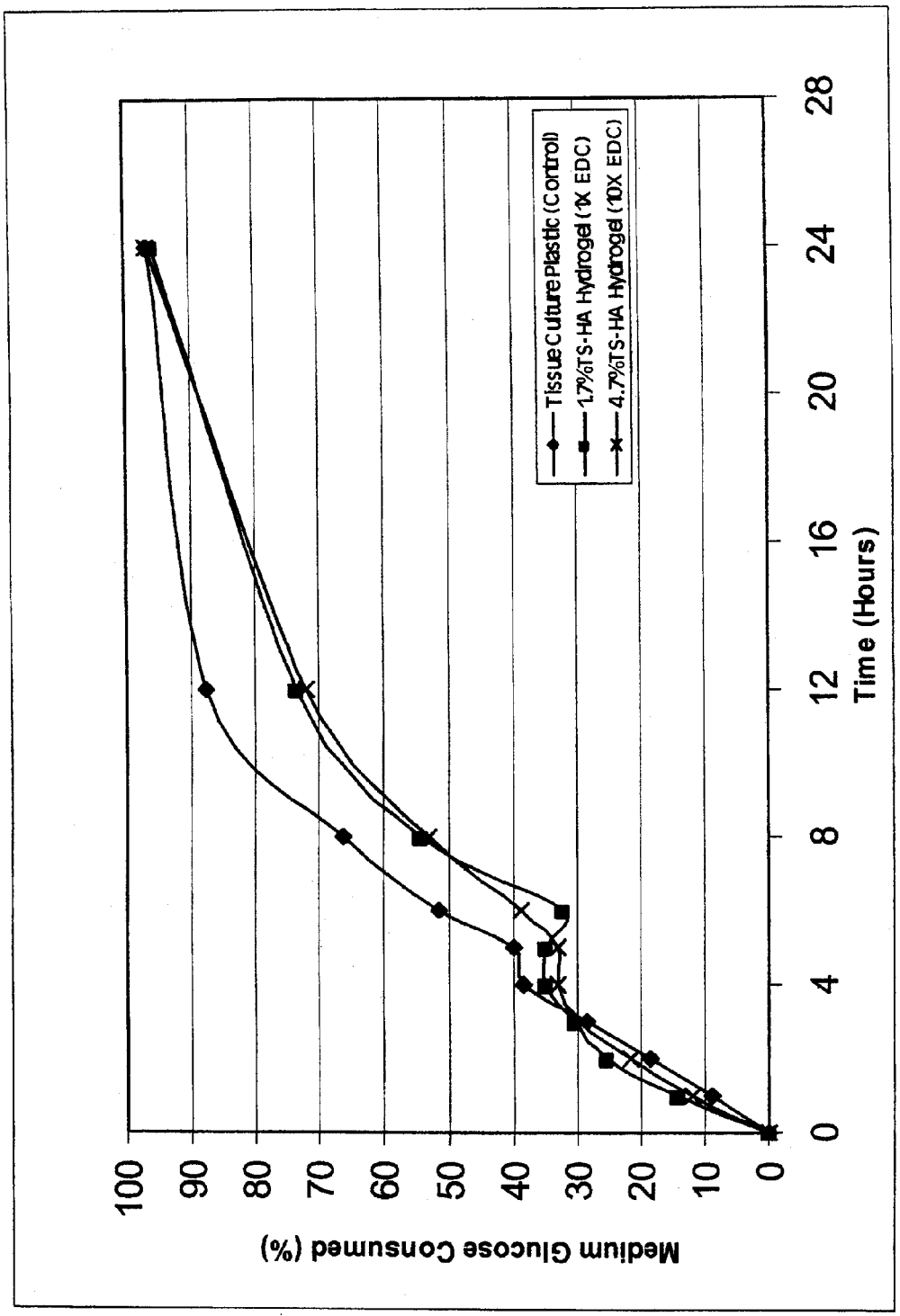
FIG. 5 is a graph showing comparative data of glucose utilization for chondrocytes embedded in T-HA hydrogels (1.7% and 4.7% T-HA) compared to cultured on tissue culture plastic (control).

Rat chondrocytes were embedded in (cross-linked) T-HA hydrogels to measure their ability to survive the cross-linking reaction. Isolated chondrocytes were suspended in the 1.7% and 4.7% T-HA hydrogels described in Example 2 by providing these live cells to the first solution to be co-dispersed with the T-HA and peroxidase, followed by introduction of the peroxide-containing second solution to initiate dityramine cross-linking. The chondrocyte-embedded 1.7% and 4.7% T-HA hydrogels exhibited uniformly distributed chondrocytes with the optical clarity of the gels allowing visualization throughout the gel. Glucose utilization was used as an indicator of cell viability after cross-linking to form the hydrogels as chondrocytes are voracious with respect to glucose consumption, depleting the medium of glucose in less than 24 hours. The results showed that chondrocytes embedded in T-HA hydrogels showed essentially the same glucose consumption profile over 24 hours as the same chondrocytes cultured in monolayer (FIG. 5). This continued for up to 7 days indicating that the cells were alive and metabolically active. Medium glucose was measured by standard hexokinase assay.

Fluorescent images of frozen sections of T-HA hydrogels containing both chondrocytes and cartilage tissue were also generated. HA samples from both the hydrogel scaffold and cartilage matrix were visualized by fluorescent staining with biotinylated HA binding protein (b-HABP) reagent while cell nuclei were visualized with standard DAPI stain. The b-HABP reagent is prepared from purified cartilage aggrecan (the G1 domain only) and link protein, and recognizes and irreversibly binds to stretches of native HA equivalent to those normally bound by aggrecan and link protein in cartilage. The results showed a more intense staining of the T-HA hydrogel with b-HABP than the cartilage as the hyaluronan in the tissue is already occupied by native aggrecan and link protein. No visible distinction could be seen between the T-HA scaffold of the hydrogel and the matrix of suspended cartilage tissue suggesting seamless integration. These results demonstrated the feasibility of maintaining the viability of chondrocytes during the hydrogel cross-linking reactions, and the ability of the hydrogel to integrate seamlessly into existing cartilage matrix, both of which are advantageous for application to cartilage repair. The results also demonstrated that sufficient stretches of the T-HA remain chemically unaltered, and available for binding by newly synthesized aggrecan and link protein in situ. The results also demonstrated that oxygen, carbon dioxide, glucose and insulin are diffusible through T-HA hydrogels according to the invention at a rate that is not limiting to chondrocyte metabolism, which is important not only to the development of cartilage substitutes but to other applications such as glucose sensor design and development of an artificial kidney.

In order to include cells such as chondrocytes in hydrogels molded into intricate anatomical shapes using the freeze/thaw technique described in Example 4, it is desirable that the enzyme driven cross-linking reaction proceed in the presence of standard cell freezing solutions such as those containing 10% dimethylsulfoxide (DMSO)/90% fetal bovine serum (FBS). This has been demonstrated in the laboratory for all of the T-HA hydrogel formulations described in Example 3. The ability to directly incorporate a solution containing 90% FBS also demonstrates the ability to include bioactive factors such as growth factors, hormones and factors controlling cell differentiation, as these are normal components of FBS.

Example 6

An experiment was conducted whereby a T-HA hydrogel as described hereinabove was implanted into Yucatan minipigs in order to repair articular cartilage defects. Following is a description of that experiment, including the experimental methods and results obtained, after a brief discussion of the background for this application.

Background

Tissue Description

Articular Cartilage Structure and Function—As discussed above, articular cartilage is the resilient load-bearing tissue that forms the articulating surfaces of diarthrodial joints. It absorbs mechanical shock and deflects or spreads applied load over greater surface area of subchondral bone. It consists primarily of a large extracellular matrix (ECM) with a sparse population of highly specialized cells (chondrocytes) distributed throughout the tissue. The primary components of the ECM are water, cartilage aggregates and type II collagen. Cartilage aggregates are composed of hyaluronan (HA), aggrecan (the large cartilage-specific proteoglycan), and link protein (LP), a small glycoprotein. Aggrecan contains a central core protein to which is attached ~100 chondroitin sulfate (CS) chains. The core protein has three globular domains with the N-terminal globular 1 (G1) domain having binding sites for both HA and LP. LP has sequence homology to the G1 domain of aggrecan, and contains binding sites for both HA and the G1 domain of aggrecan. Each cartilage aggregate is composed of a single HA chain, to which are attached hundreds of aggrecan/LP duplexes. These large cartilage aggregates are trapped at one fifth of their free solution volume within a tight meshwork of type II collagen fibers, which resist further swelling. This molecular architecture contributes to the tissues mechanical properties and function as described below.

Swelling Pressure—The HA and CS chains in cartilage aggregates contain repeating carboxyl and/or sulfate groups. In solution, these groups become ionized ($COO^-$ and $SO_3^-$), and in the physiologic environment they require positive counter ions such as $Na^+$ to maintain overall electroneutrality. These free-floating ions within the interstitial water are present at a higher concentration than that found in the surrounding fluids (i.e. synovial fluid) giving rise to an osmotic pressure (Donnan pressure). In cartilage, ions are prevented from flowing out of the tissue along the concentration gradient by the fixed nature of their negative counter ions (i.e. the $COO^-$ and $SO_3^-$ groups on the HA and/or CS chains), and the need to maintain electroneutrality. Water flow into the tissue to equilibrate the concentration gradient is resisted by the inextensible nature of the collagen meshwork preventing further swelling.

Alternatively, tight cartilage aggregate packing causes the fixed-negative charge groups to be spaced only 10 to 15 angstroms apart, resulting in strong charge-to-charge repulsive forces (electrorepulsive forces). As with the Donnan effect, the tendency to swell to lessen these repulsive forces is resisted by the inextensible nature of the collagen meshwork. When compressed, the distances between charge groups decrease, thus increasing the charge-to-charge repulsive forces and increasing the free-floating positive counter ions concentration. Thus both the Donnan and electrorepulsion effects are intensified by compression. Both effects contribute to the swelling pressure of articular cartilage and its ability to resist deformation and absorb compressive loads.

Stress Shielding Effect—Articular cartilage is often described as a viscoelastic, biphasic material, composed of a solid phase (cartilage aggregates, collagen, etc.) and a fluid phase (water and dissolved ions). The macromolecular architecture of the ECM of articular cartilage functions to deflect applied forces during loading from the wear susceptible solid phase of the tissue to the wear resistant fluid phase or water. This stress shielding occurs due to the elegant design of the cartilage ECM which produces a material with very low permeability creating a drag during interstitial fluid flow. Interstitial fluid pressure is generated during compressive loading, and during dynamic loading, is the primary force responsible for supporting the applied load with matrix compression a minor factor. During compression, the porosity is reduced further, which increases the already high frictional drag forces. The load support is gradually transferred from the fluid phase (as the fluid pressure dissipates) to the solid phase. Typically, for normal cartilage, this equilibration process takes 2.5 to 6.0 hours to achieve. Thus, load support through fluid pressurization predominates within the tissue.

Need for Synthetic Material

Increased water content and decreased proteoglycan content are the most apparent early changes in osteoarthritic cartilage. These changes reflect an increase in tissue permeability. Increased permeability diminishes the fluid pressurization mechanism of load support in cartilage (stress shielding), requiring the collagen-aggrecan solid matrix to bear more load, which may be an important contributing factor in the development and progression of cartilage degeneration. Bioartificial cartilage substitutes that do not mimic the low permeability of normal, healthy articular cartilage may be predisposed to degeneration by a similar mechanism.

One of the most difficult challenges facing orthopedic surgeons is treating patients who have suffered focal cartilage lesions, but are too young or too active for a total joint replacement. These localized cartilage defects can be very debilitating. Restoring these localized areas without a total joint replacement would be a preferred approach with significant benefits including reduced surgical requirements, shorter recovery times, lower cost, and slowing or arresting the further degradation of the load bearing surface.

This example demonstrates the application of a tyramine-substituted HA (T-HA) hydrogel for repair of this type of localized cartilage defect.

Experimental Description

Design of Extracellular Matrix Material having Desired Properties

Natural articular cartilage has the elastic as well as physical and chemical properties described above, which impart its unique ability to absorb mechanical loads and to deflect impact loads away from the subchondral bone. To produce a suitable synthetic cartilage material made from a T-HA hydrogel as disclosed herein, it was important to design the macromolecular network for the hydrogel so as to emulate those properties as nearly as possible through judicious selection of reagent concentrations, cross-linking conditions, incorporated living cells as well as other molecules, etc.

The results from confined compression testing of T-HA hydrogels (see Example 3 above) provided an initial basis for the synthesis of an appropriate synthetic T-HA material having properties matched to those measured for normal articular cartilage. They also illustrate the spectrum of material properties that can be manufactured from a single formulation of T-HA. Based on those data, a T-HA hydrogel composed of, inter alia a macromolecular network of dityramine cross-linked hyaluronan molecules was selected based on the following criteria in order to produce a synthetic implantable cartilage material.

A material composed solely of HA was chosen because hydrogel compositions with the compressive properties of cartilage could be formed using HA alone as the scaffold material (Example 3), while avoiding possible host response to the protein component of aggrecan if it were used as a scaffold material. Reaction conditions (tyramine/EDC ratio) were chosen to produce a percent tyramine substitution of 5% (Example 2) as this provided sufficient cross-linking to produce a material with the compressive properties of cartilage (Example 3) while maintaining the majority of the native HA structure. HA was substituted with ~5% tyramine, as described in Example 1, except that the HA was dissolved at 5 mg/ml rather than 1 mg/ml to conserve reagents. The absolute concentration of all other reagents remained the same so that the tyramine and EDC were at a 2-fold rather than 10-fold molar excess based on the molar concentration of HA carboxyl groups. A concentration of 125 mg/ml of HA in sterile saline was chosen as this concentration in saline had a compressive aggregate modulus most closely resembling that of articular cartilage (saline data not shown). It was also the concentration deemed most appropriate based on the experience of our clinician collaborator. Peroxidase was added at 10 U/ml prior to application in an in situ cross-linking protocol as described below. The in situ cross-linking protocol was chosen as it provided the best opportunity for integration with surrounding cartilage matrix. It also allowed easy and complete filling of the surgically produced cartilage defect without the need to know or measure the defect's exact dimensions. Pre-cast (in vitro cross-linked) plugs would either require exact dimensions or sculpting of pre-formed shapes to fit the defect. No cells or bioactive factors where added in this experiment as this experiment was intended to evaluate the hydrogel material independent of complicating factors derived from inclusion of cells or bioactive factors. However, cells or bioactive factors could be included as described hereinabove to produce desired effects.

Surgical Procedure

Pre-Operative—After arrival in the biological resource unit, Yucatan minipigs (~7-8 months of age, ~30-35 kg) were maintained for a minimum of 7 days to ensure full acclimatization. After pre-medication with Ketamine (20 mg/kg I.M.) as anesthesia and Ambipen (40,000 U/kg I.M.) as prophylaxis antibiotic, the animal's rear legs were shaved and painted in Betadyne as simultaneous bilateral surgery of both knees was performed. A general anesthesia was maintained by inhalation with Isoflurane (1-2.5% volume) in $O_2$ following intubation. Thiopental was used as needed (to effect 25 mg/ml I.V.). During surgery, the animal was monitored for heart rate, respiration rate, body temperature, etc.

Opening—A longitudinal midline skin incision was made and carried down sharply through the pre-patellar bursa.

Electrocautery was used for hemostasis. The lateral border of the patella was identified and a lateral para-patellar arthrotomy was performed. The lateral retinaculum and musculature were tagged with #1 vicryl suture. The patella was dislocated medially to expose the femoral trochlea.

Figure 6:
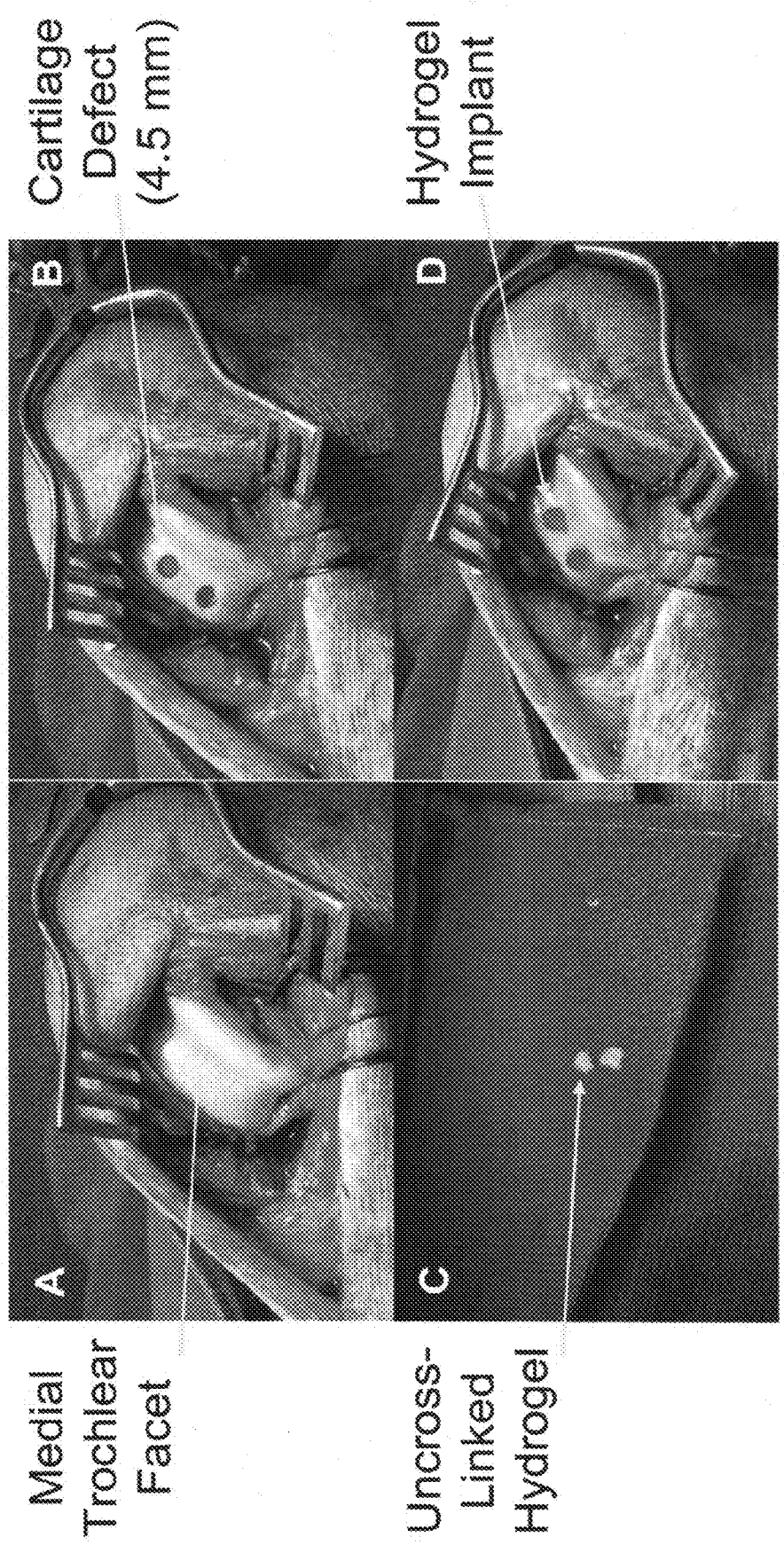
FIG. 6 is a series of four photographs illustrating a surgical procedure to implant a T-HA hydrogel into articular cartilage defects according to an aspect of the invention described in Example 6.

Cartilage repair—As seen in FIG. 6, two circular full thickness chondral defects (~4.5 mm in diameter, panel B of FIG. 6) were created in the medial trochlear facet of the femoral chondyle (panel A of FIG. 6) using an Acufex 4.5 mm mosaiaplasty chisel and a sharp, curved currette taking care as much as possible not to disrupt the osteochondral plate. The defects were filled with in situ cross-linked T-HA hydrogel (125 mg/ml in sterile saline) as follows to produce a hydrogel implant having the composition described above in order to reproduce the in vitro measured compressive properties of natural cartilage as described above. Initially, each defect was rinsed with 0.01 cc of 0.6% hydrogen peroxide, and then immediately blotted dry with sterile gauze. Subsequently, a plug containing 0.15 cc of uncross-linked hydrogel paste (panel C of FIG. 6) having the composition and prepared as described above was inserted into and used to fill each defect with the surgeon smoothing the surface of the hydrogel implant with fingertips to match the contour of the articular surface. A sterile piece of filter paper (Whatman 50) soaked in 0.6% hydrogen peroxide was pressed against the surface of the hydrogel implants for five minutes to cross-link the hydrogel in the defect. During the 5 minutes, the filter paper was rubbed back and forth across the implant surface to prevent integration with the filter paper, and to effectively polish the implant surface. After 5 minutes the filter paper was removed, excess hydrogel trimmed from the site, and then ~0.01 cc (1 drop) of 0.6% hydrogen peroxide added to the surface of each implant plug (panel D of FIG. 6). The Patella was reduced anatomically over the femoral trochlea. The Patella was dislocated and reduced again to ensure secure primary stability of the hydrogel.

Closing—The joint was irrigated with sterile saline. The wounds were closed in layers with vicryl sutures. Specifically, the arthrotomy was closed with interrupted #1 vicryl suture, the subcutaneous tissue was closed with interrupted 2-0 vicryl suture and the skin layers were closed with interrupted 3-0 vicryl suture. No restriction of movement was required after surgery.

Post-Operative—The animal returned to full weight bearing immediately following surgery. Analgesia was provided by Buprenorphine (0.02 mg/kg I.M.) for 24 hours and a Fentanyl Patch (50 mcg/hr) for 3 post-operative days. Post-operative prophylactic antibiotic in the form of cephalexin 500 mg twice per day was given for 7 days. The animals were kept in a conventional animal run.

Figure 7:
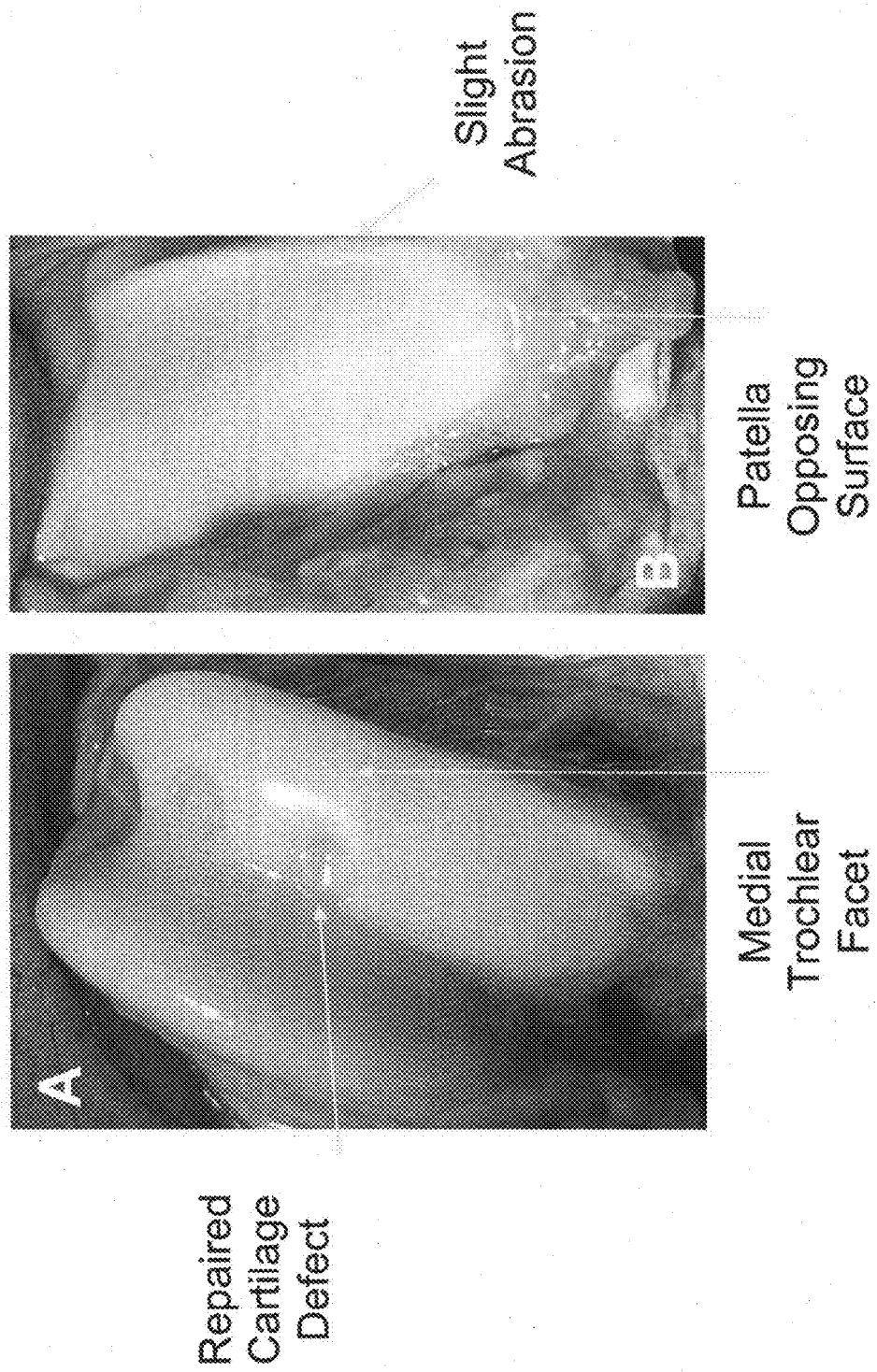
FIG. 7 is a series of two photographs showing the T-HA hydrogel implants one month after implantation into the medial trochlar facet of a Yucatan pig as described in Example 6, as well as the opposing (articulating) patella surface.

Post-Implantation Data—At one month post-implantation, the animal was euthanized with overdose of the barbiturate, Beuthanasia D Special (1 ml/10 kg B.W., I.V.) under general anesthesia. After euthanasia, the entire knee joint was carefully dissected, macroscopically evaluated and photo documented. As seen in FIG. 7, macroscopic inspection of the knees at 1 month revealed no significant effusion and no evidence of inflammatory reaction. The lesions were partially filled with a white material (the implanted T-HA hydrogel as well as other factors or cells which may have migrated into the hydrogel post-operatively) and the surrounding articular cartilage and opposing articular surface (patella) were normal in appearance except for a slight abrasion appearing on the opposing articular surface as seen in panel B of FIG. 7. It is not evident this abrasion was the result of rubbing against the implants, particularly given its location on the Patella in a position which does not appear as though it would have abraded against the implants during normal articulation of the joint.

The results indicate no apparent negative effect on joint health as a result of the hydrogen peroxide or peroxidase reaction used for in situ cross-linking of the hydrogel, and demonstrated the utility of the hydrogels disclosed herein, comprising a dityramine cross-linked hyaluronan macromolecular network, as a synthetic implantable extracellular matrix for use as a synthetic in vivo cartilage replacement or implant material.

Example 7

An experiment was conducted whereby a T-HA hydrogel as described hereinabove was implanted into canine and rabbit models in order to repair vocal cord defects as well as to augment vocal cords. Following is a description of that experiment, including the experimental methods and results obtained, after a brief discussion of the background for this application.

Background

Tissue Description

The vocal cords are complex, multilayered structures under very fine neuromuscular control. The overlying mucosa is composed of a non-keratinized, stratified squamous epithelium, with a multilayered, lamina propria deep to the epithelium. Underlying the lamina propria is a muscular layer consisting of the thyroarytenoid muscle which inserts into the thyroid cartilage anteriorly and the vocal process of the arytenoid cartilage posteriorly. The thyroarytenoid muscle can stiffen or relax, altering the tension on the lamina propria and thereby altering the vibratory dynamics of the epithelium, which produces the finely coordinated vibrations responsible for high quality speech production.

The biomechanics of human voice production have been attributed to the action of certain biological macromolecules naturally found within the extracellular matrix (ECM) of the lamina propria. Hyaluronan (HA) is a ubiquitous molecule, which is most concentrated in specialized tissues such as the vocal cords, synovial fluid, umbilical cord, dermis, and cartilage. In these tissues, its function is manifold, influencing tissue viscosity, shock absorption, wound healing, and space filling.

The unique structure of HA elucidates its multiple functions. It consists of D-glucuronic acid and N-acetylglucosamine arranged in repeating disaccharide chains, containing as many as 30,000 repeating disaccharide units with a mass of more than 10 megadaltons. As HA is a polysaccharide instead of a protein, it is non-antigenic. Under biological conditions, it is a negatively charged, randomly coiled polymer, filling a volume more than 1,000 times greater than expected based on molecular weight and composition alone. The strong negative charges attract cations and water, allowing it to assume the form of a strongly hydrated gel, and giving HA its unique viscoelastic and shock-absorbing property.

Vocal cord viscoelasticity is essential to high quality voice production, as it directly affects the initiation and maintenance of phonation and the regulation of vocal cord fundamental frequency. HA in the human glottis is concentrated in the lamina propria and its importance has been quantified by comparing the biomechanical properties of cadaveric vocal cords with and without HA. Treatment of the vocal cords with hyaluronidase led to a 35% average reduction in vocal cord stiffness and a 70% mean reduction in high frequency vocal fold viscosity, thus illustrating the significance of HA in these tissues.

Need for a Synthetic Material

Vocal Cord Repair—Defects in the vocal cords have a dramatic effect on vocal production. Arising either de novo, or resulting from surgical intervention, heterogeneous masses within the vocal cords disrupt the finely coordinated vibrations responsible for high quality speech production. Patients with de novo lesions usually present early in the disease course, due to persistent hoarseness. When presenting with an early stage malignant process (T1-T2 in the Tumor, Node, Metastasis staging system), patients undergo rapid treatment consisting of either external beam radiation therapy or endoscopic surgery. Such patients are counseled that poor post-treatment voice quality is an expected side effect of effective tumor eradication. When presenting with a presumed benign process, patients are faced with a conundrum, for the surgical treatment often produces speech quality as poor as that caused by the lesion itself. Unfortunately, current standard laryngeal operative technique cannot provide for effective removal of either benign or malignant lesions without causing poor vocal outcomes secondary to vocal fold scarring. This is due to the mechanism of wound healing in the unique anatomy of the larynx. The superficial, vibratory surfaces of the vocal cords become tethered to the deeper layers by the post-treatment scar, preventing physiologic phonatory oscillation.

HA in the human glottis is concentrated in the lamina propria, a histological layer separating the vocalis muscle from the overlying epithelium. The lamina propria allows the epithelium to vibrate over the taut vocalis muscle, like waves propagating over a pond. This "mucosal wave" is the sine qua non of effective speech production. In the presence of benign or malignant lesions of the vocal cords, the mucosal wave is disrupted. Even in the normal process of healing, scar bands and disorganized collagen "tether" the superficial mucosa to the deeper layers of the vocal cords, disrupting the normal mucosal wave and impairing vocal production. The shock absorbing nature of HA allows it to act as a tissue damper, protecting the mucosal surfaces from the oscillatory trauma experienced during phonation. HA also appears to facilitate wound repair by minimizing fibrosis and scarring, thereby protecting the vocal cord from the permanent damage resulting from trauma.

The development of a technique, permitting the restoration of a fully vibratory phonatory surface on vocal cords undergoing laser or cold surgical treatment, would enable a large population of patients with both benign and malignant processes to undergo treatment of their tumors with the expectation of unprecedented post-operative speech outcomes.

Vocal Cord Augmentation—A variety of disorders and diseases adversely affect glottic function, vocal quality and the ability to communicate. Approximately 7 million people in the United States suffer from dysphonia or voice impairment, and those affected by vocal cord paresis/paralysis are a significant subset of this population. It is estimated that 1-4% of all cardiac and thyroid surgeries in the United States result in vocal cord paresis or complete paralysis due to inadvertent vagus nerve or recurrent laryngeal nerve injury during surgery.

Another condition affecting vocal cord function is unilateral vocal fold paralysis (UVP). In UVP the problem is malposition of an insensate vocal cord. While medialization results immediately following nerve injury due to opposing tensions of the laryngeal adductors and abductors, the paralyzed vocal cord rapidly lateralizes to a paramedian position. The arytenoid cartilage prolapses into the larynx following recurrent laryngeal nerve injury, resulting in a change in vertical height of the vocal cord, as well as decreased dynamic tension often resulting in vocal fold bowing. Atrophy with resultant shortening and bowing of the vocal cord occurs later as the thyroarytenoid muscle atrophies due to a lack of neural stimulation. As a result of atrophy and lateralization, the contralateral vocal cord cannot fully contact the paralyzed cord, leading to manifestations of UVP.

Such manifestations include breathy hoarseness, a weak cough, an inability to valsalva (protect the airway), and difficulty swallowing; complications include aspiration (solids and liquids) and recurrent pneumonia. This can result in a life-threatening condition due to increased incidence of recurrent pulmonary infections.

As only one functional vocal cord is required for normal voice production, successful treatment consists of "medialization" of the paralyzed vocal fold, thereby enabling it to contact the contralateral mobile vocal fold. This normalizes voice production and prevents aspiration minimizing the risk of aspiration pneumonia. Vocal fold paralysis is currently treated in two ways: open trans-cervical approaches or trans-oral endoscopic vocal cord injection, also known as injection laryngoplasty therapy (ILT). Ishiki-type I thyroplasty is the most commonly performed trans-cervical approach, where a "window" is created in the thyroid cartilage to allow placement of a silastic implant into the body of the atrophic, paralyzed vocal fold, in effect pushing it into a more medial position. This procedure has a permanent effect, although complications include implant migration, extrusion, or infection.

In ILT, the paralyzed vocal cord is medialized by the endoscopic injection of an exogenous substance. A wide variety of synthetic and biologic materials are currently available as an injectant for treatment of UVP, including: gelfoam, hydroxyapatite, autologous fat or facia, acellular cadaveric dermis (Cymetra®), collagen or Teflon®/Gortex®. Unfortunately, all have proven to be less than ideal with none fulfilling all desired criteria for the ideal material for long-term vocal cord augmentation. Such limitations create the need for either re-injection or over-injection to account for the projected loss of volume.

A biocompatible, injectable material such as a T-HA hydrogel as disclosed herein can be designed to mimic the rheological properties of the natural vocal cord tissue and persist indefinitely in vivo without migration. The design, chemistry, and material properties of a T-HA hydrogel as described herein can be tuned to produce an injectable bio-implant that is uniquely suited to otolaryngology treatments such as ILT through judicious selection of component concentrations and cross-linking methodologies as described hereinabove.

A suitable biocompatible, high-longevity synthetic material also is desirable to treat pre-existing sulcus or scarring that can develop due to trauma or develop spontaneously with aging. Such a material also could be used advantageously in place of saline as a diagnostic and surgical aid prior to vocal cord surgery. Conventionally, saline is injected within the HA matrix of the vocal cord lamina propria between a lesion to be surgically removed and the underlying ligament. This is done to: a) determine if the lesion involves the underlying ligament; and b) to make the surgery easier by increasing the distance between the lesion and the ligament (cold instruments), or providing a heat sink (laser). Ligament involvement complicates the surgery with penetration of the ligament to be avoided if possible. This procedure could benefit from the incorporation of hepatocyte growth factors in the hydrogel, which is used to increase HA production in the lamina propria and decrease collagen production associated with scarring.

Experimental Description

Design of Extracellular Matrix Material having Desired Properties

An ideal synthetic matrix or biomaterial for vocal cord augmentation will have the following characteristics: 1) biocompatible, so there is no unfavorable immunologic response; 2) easily injectable to allow a surgeon to control the exact amount and location of injection through a small needle; 3) readily available with minimal preparation for optimal time efficiency and potential application to the outpatient office setting; 4) possess the same or similar biomechanical properties to the vocal fold component being augmented to cause minimal alteration in the natural function of the augmented structure; 5) resistant to resorption or migration, so that the initial augmentation result is maintained; and 6) easily removable in the event of revision surgery.

The T-HA hydrogels disclosed herein meet all six of these criteria, most important being that its biomechanical properties can be tuned through judicious selection of reactant/synthesis parameters and GAG (e.g. HA) concentration to produce the necessary macromolecular network for producing a hydrogel having desired viscoelastic and biomechanical properties. Specifically, results of both in vitro and in vivo preliminary studies have allowed favorable comparisons to be drawn against the above criteria. First, transplantation of T-HA hydrogels into various animal species including rat, rabbit, dog and pig all have demonstrated little to no host immune response. Second, uncross-linked T-HA hydrogels at the concentrations required for vocal cord augmentation at the lamina propria or muscle level easily pass through a 21 gauge needle. Third, medical-grade HA is readily available and has been used for years in FDA-approved formulations such as Healon and Restylane. Furthermore, uncross-linked T-HA hydrogel and hydrogen peroxide (cross-linking agent) solutions can be readily pre-made, in off-the-shelf formulations that require no preparation by the surgeon. Fourth, the T-HA hydrogels disclosed herein can be formulated to match the mechanical properties of the various tissues of the glottis including the lamina propria, thyroarytenoid muscle, and thyroid or arytenoid cartilages. Fifth, the unique cross-links and non-protein nature of the T-HA hydrogels have demonstrated resistance to resorption in in vivo experiments. This implies that the initial augmentation result will be maintained. Finally, formation of a solid continuous implant through the novel in situ cross-linking protocol made possible through the non-immunogenic enzyme-driven cross-linking architecture described herein should prevent migration and allow for easy location and removal of the hydrogel implant should revision surgery be required.

With respect to the fourth point above, the results from confined compression testing of T-HA hydrogels (see Example 3 above) provided an initial basis for the synthesis of an appropriate synthetic T-HA material having properties matched to those of normal vocal cord tissue. Based on those data, a T-HA hydrogel composed of, inter alia a macromolecular network of dityramine cross-linked hyaluronan molecules was selected based on the following criteria in order to produce a synthetic implantable vocal cord repair or augmentation material.

Choices of scaffold material (HA alone), percent tyramine substitution (~5%), protocol for tyramine substitution of HA (modified from Example 1), and the non-incorporation of cells and bioactive factors were as described in Example 6. A concentration range of between 2.5 and 10 mg/ml of T-HA hydrogel in sterile saline most closely matched the rheological and vibratory properties of the vocal cord lamina propria. The 2.5 mg/ml concentration of T-HA hydrogel was deemed most appropriate based on the extensive clinical experience of our clinician collaborators with both the vocal cord tissue and other injectable materials used for vocal cord repair and augmentation. In vitro cross-linked hydrogel was used rather than an in situ cross-linking protocol based on the experience of our clinician collaborators with other injectable materials for vocal cord repair and augmentation. In vitro cross-linking was as described in Example 1. Based on the results of the rabbit and canine experiments described below a preferred embodiment for vocal cord augmentation using the disclosed hydrogel material as envisioned by the inventors would use the in situ cross-linking protocol and a T-HA concentration to more closely match injection into the deeper muscle layers of the vocal cord.

Surgical Procedure

Pre-Operative—After arrival in the biological resource unit, mongrel dogs or New Zealand white rabbits (depending on the experiment, described below) were maintained for 7 days for full acclimatization. After pre-medication and general anesthesia per IACUC-approved protocols, each animal was intubated and maintained in stage III surgical anesthesia. The animal was positioned supine. After grasping and superiorly retracting the tongue, a Dedo laryngoscope was placed transorally providing good exposure of the larynx. The tip of the laryngoscope was positioned several centimeters proximal to the superior surface of the true vocal cords. The laryngoscope was then suspended. A rigid videostroboscopic telescope was positioned above the true vocal cords, permitting complete inspection and imaging of the larynx.

Vocal Cord Repair—For vocal cord repair, lateral-based microflaps were raised in both vocal cords of dogs, and then soft tissue defects were created equivalent to 50% of the vocal cord mass, including lamina propria and underlying muscle. One side underwent soft tissue reconstruction (filling) with the T-HA hydrogel, while the contralateral side served as an unrepaired (unfilled) control. The microflap was then redraped over the hydrogel such that the epithelium was completely continuous. This study used 2.5 mg/ml ex vivo cross-linked T-HA hydrogel in saline (5% tyramine substituted) prepared as described above to approximate the rheological properties of the lamina propria. After surgery, the dogs were weaned from the anesthesia and transferred to the recovery room. The animals received analgesia for 1 to 2 days per IACUC-approved protocols.

Injection Laryngoplasty Therapy (Vocal Cord Augmentation)—After anesthesia, a 27 gauge laryngeal needle was used to inject approximately 0.25 ml of 2.5 mg/ml ex vivo cross-linked T-HA hydrogel in saline (5% tyramine substituted) at the left anterior and posterior membranous vocal cord of rabbits. The injections were made in the superficial layer of the lamina propria.

Based on the results from the above experiments with dogs (vocal cord repair) and rabbits (ILT), the following preferred embodiment for vocal cord augmentation using the disclosed hydrogel material is envisioned by the inventors. For ILT, the lateralized and atrophied vocal cord are injected with 50 mg/ml of the uncross-linked T-HA hydrogel in saline (5% tyramine substituted) with peroxidase at the level of the thyroarytenoid muscle. Preferably one bolus of hydrogel would be used to obtain the desired medialization, but no more than two. A 21 gauge laryngeal needle is used to inject the hydrogel. Cross-linking would be initiated by injection of a small volume of dilute hydrogen peroxide through a 27 gauge needle into the center of the implanted bolus of hydrogel using the 21 gauge needle, which would not have been withdrawn, for purpose of orientation. Cross-linking of the hydrogel into a solid implant would be achieved within minutes and verified by feel. After surgery, the animals would be weaned from the anesthesia and transferred to the recovery room. The animals would receive analgesia for 1 to 2 days per IACUC-approved protocols. At the time of euthanasia, the vocal cords of each animal would be carefully dissected, macroscopically evaluated and photo documented.

Post-Implantation Data

Figure 8:
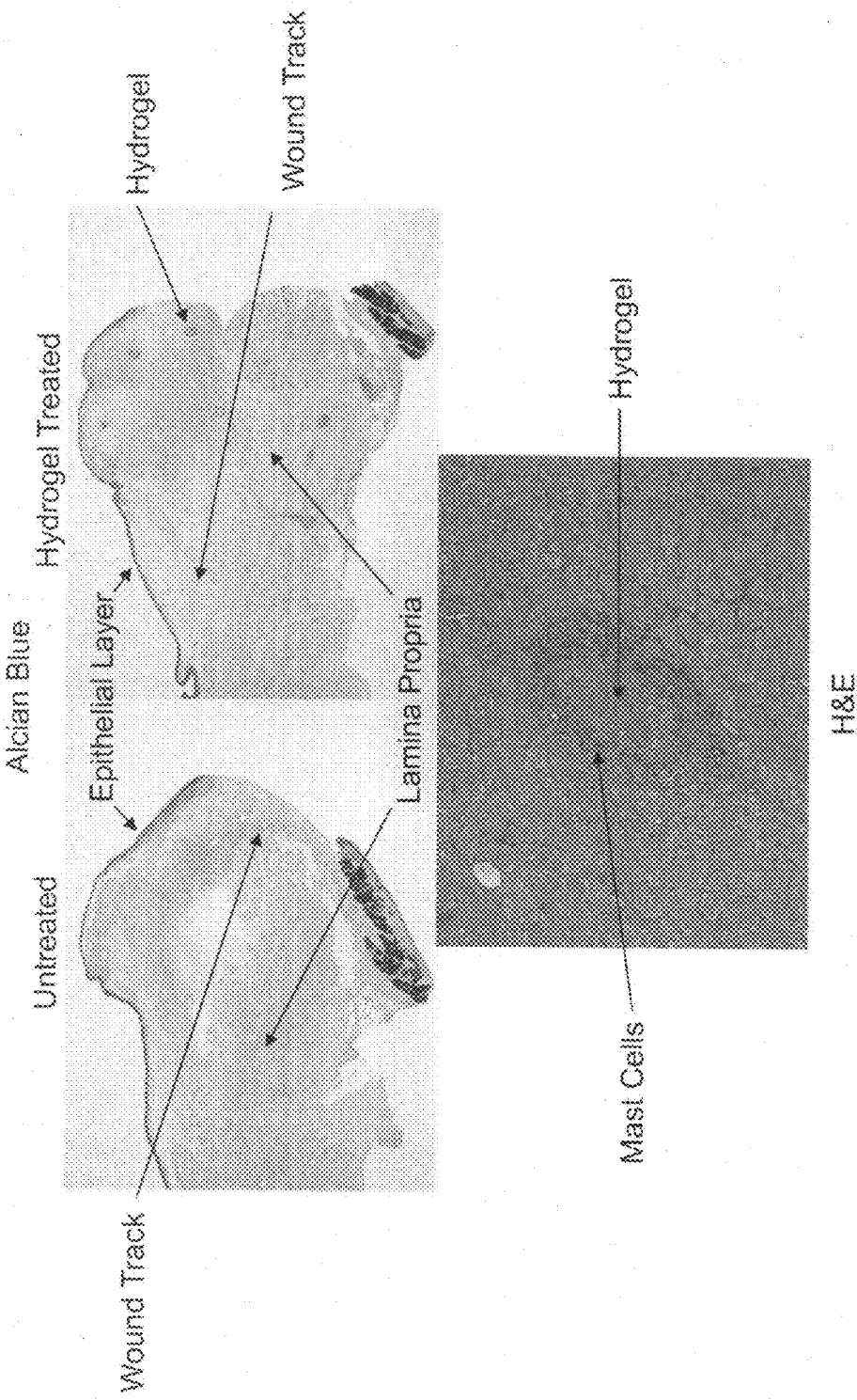
FIG. 8 is a series of photographs illustrating the histological results of control side (unfilled) and experimental side (TB-HA hydrogel filled) canine vocal cords; 3 months post-operatively, following a vocal cord repair procedure using a T-HA hydrogel as a synthetic vocal cord material as described in Example 7.

Vocal Cord Repair—At the time of euthanasia, the vocal cords of the dogs were carefully dissected, macroscopically evaluated and photo documented. The degree of wound healing was assessed histologically by a consulting pathologist with specific attention paid to inflammatory infiltrates, HA staining (normal matrix production), hydrogel staining and collagen staining (scarring). FIG. 8 shows representative histological results of control side (unfilled) and experimental side (T-HA hydrogel filled) vocal cords stained with alcian blue for one of the dogs three months following surgery. Gross observation indicated a more normal appearance and vibratory properties for the T-HA hydrogel-treated vocal cord compared to untreated controls. The histological results indicated significant scarring in the untreated control vocal cord along the wound track as indicated by a lack of deposition of GAG (i.e., HA) and increased collagen deposition when compared to the T-HA-filled wound track of the experimentally repaired vocal cord.

Only small foci of T-HA hydrogel could be found in the experimental vocal cord at 12 weeks, which show a minimal foreign body response with a layer of surrounding mast cells observed. This may indicate degradation of the T-HA hydrogel with concomitant deposition of normal HA-containing tissue matrix. However, given the low concentration (2.5 mg/ml) and thus the very fluid nature of the hydrogel used in this study, it is more likely that much of the hydrogel was lost from the wound site prior to closure of the site as the epithelial microflap knitted to the opposed underlying tissue. Hydrogel between the microflap and opposed underlying tissue is actually predicted to inhibit the knitting process contributing to hydrogel loss from the wound site. Thus, the positive wound healing effect seen is believed due to only a thin layer of hydrogel retained at the wound site rather than the volume-filling bolus of hydrogel initially implanted. These results indicate the ability of the hydrogel to prevent scarring and match the rheologic properties of the lamina propria.

Figure 9:
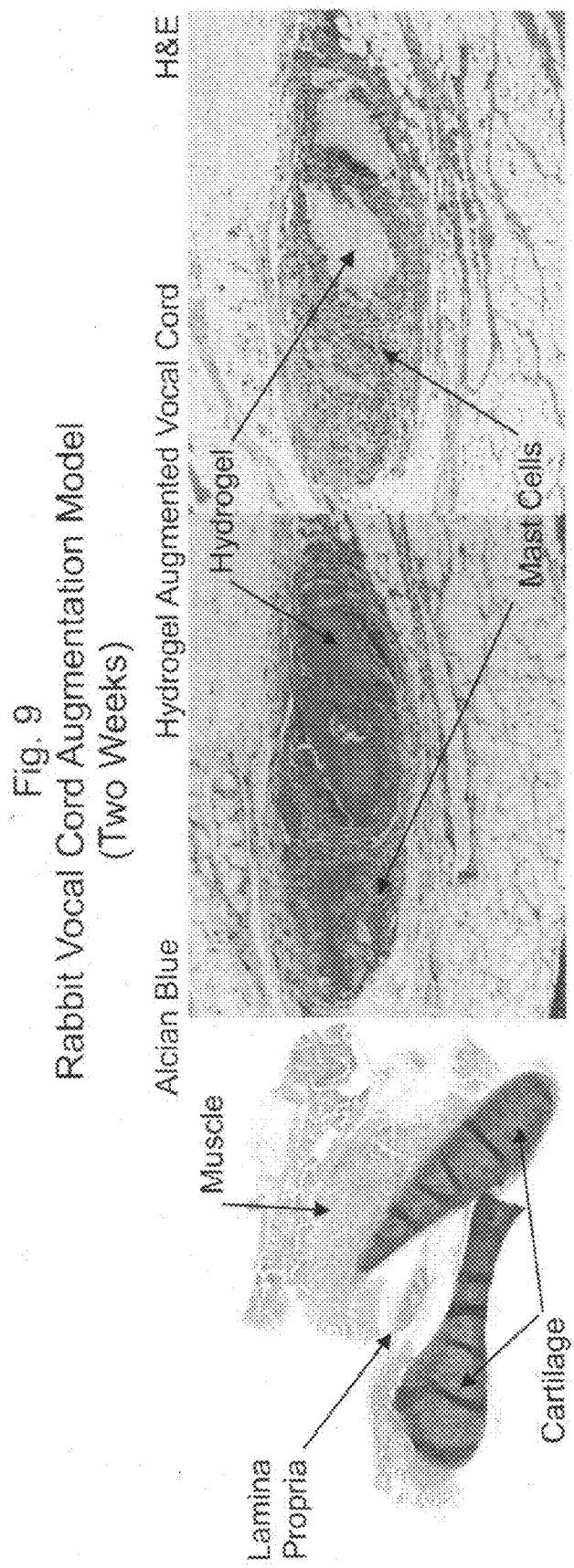
FIG. 9 is a series of photographs illustrating the histological results of surgically augmented vocal cords in a rabbit model using a T-HA hydrogel as a synthetic vocal cord material, also as described in Example 7.

Injection Laryngoplasty Therapy (Vocal Cord Augmentation)—At the time of euthanasia, the vocal cords of the rabbits were carefully dissected, macroscopically evaluated and photo documented. Histological evaluation by a consulting pathologist was used to assess the inflammatory response and retention of the hydrogel. Representative histological results with Alcian Blue staining to detect the hydrogel and hematoxylin & eosin (H&E) for general morphology are shown in FIG. 9 for one of the rabbits that underwent the augmentation procedure at two weeks post-operatively. As seen in the figure, pockets of T-HA hydrogel could be found in the injected vocal cords at 2 weeks, which show a minimal foreign body response with a layer of surrounding mast cells observed.

Example 8

An experiment was conducted whereby a T-HA hydrogel as described hereinabove was implanted into a rabbit model in order to fill the vitreous cavity of the eye in order to prevent or treat vitreo-retinal diseases such as retinal detachment. Following is a description of that experiment, including the experimental methods and results obtained, after a brief discussion of the background for this application.

Background

Tissue Description and the Need for a Synthetic Material

Vitreo-retinal diseases, such as retinal detachment, diabetic retinopathy and others, are among the most common causes of blindness. The vitreous cavity of the eye normally is filled with a gel like substance. In retinal detachment surgery, the vitreous is surgically removed (a procedure called "vitrectomy"), the retina is re-attached against the back wall of the eye, and a replacement substance is injected into the vitreous cavity. Vitreous substitutes are used for a number of different purposes in the vitreous cavity of the eye. These include (1) achieving a long term tamponade after retinal re-attachment surgery to keep the retina apposed to the wall of the eye; (2) in intra-operative procedures such as unfolding of retinal tears, the removal of subretinal fluid and the flotation and removal of dislocated intraocular lens components; (3) for developing a sustained release system that could maintain therapeutic drug levels in the posterior segment of the eye over long periods of time.

A number of different compounds are used as vitreous substitutes after retinal re-attachment surgery. These compounds have physical properties that permit successful retinal re-attachment but fail in other important surgical goals. Gases injected into the eye provide short term retinal tamponade but re-absorb quickly and cause significant optical distortion while they are in the eye. Perfluorocarbon liquids are effective intra-operative tools for flattening the detached retina but cause unacceptable toxicity when left in the eye for prolonged periods of time. Silicon oil is used as a medium term retinal tamponade but also carries a risk of toxicity and causes significant optical distortion.

Alternatively, substitute vitreous compounds are desirable for use as safe, long term or time-released drug delivery vehicles in the eye. Many chronic inflammatory and infectious conditions of the eye, such as sarcoidosis, idiopathic posterior uveitis and cytomegalovirus retinitis, necessitate intraocular injections of medication. Repeat intra-ocular injections pose risks such as bleeding, retinal detachment and infection. A stable, non-toxic vehicle is needed for sustained intravitreal drug delivery.

Hyaluronan (HA) is an acellular substance that is an essential component of natural vitreous in humans and other mammals. Formulations of hyaluronan are already in use in some ophthalmic surgical procedures. For example, sodium hyaluronate is the most commonly used viscoelastic surgical device for anterior segment and cataract surgery. Unfortunately, sodium hyaluronate and other previously tested hyaluronan substitutes are dissolved relatively quickly in human tissues. These substances have not proven effective in vitreous surgery because of their failure to provide long-term retinal tamponade.

Experimental Description

Design of Extracellular Matrix Material having Desired Properties

The most common need for a vitreous replacement is during retinal detachment surgery. A significant challenge is maintaining the retina flat against the wall of the eye for a prolonged period of time post-operatively. An ideal vitreous substitute should be optically clear to allow maximum visual rehabilitation during the recovery period. Finally, retinal detachments that occur inferiorly in the eye pose a particular challenge. For the retina to remain flat post-operatively, the vitreous replacement must be directly apposed to the area of the retinal tear. To tamponade inferior breaks the patient must often lie in a face down position for weeks after the surgery. None of the vitreous substitutes in use today satisfy all of the current clinical needs.

There is a need for a non-toxic, optically clear, vitreous substitute that will result in improved surgical results and post-operative visual rehabilitation in patients undergoing retinal detachment surgery.

Hydrogels made from a tyramine-substituted and cross-linked hyaluronan (T-HA) macromolecular network as disclosed herein present an ideal choice for a synthetic vitreous material. Specifically, the novel enzyme-driven cross-linking chemistry described above for cross-linking the tyramine-substituted hyaluronan macromolecules using a peroxidase and $H_2O_2$ allows the resulting hydrogels to be cross-linked ex vivo, and to remain stable in animal tissues. For example, studies in rats have demonstrated that this material does not degrade over several months when injected subcutaneously (see Example 9). At low concentrations the hydrogels are optically clear, easily injected through a syringe or a vitrectomy port and have a specific gravity higher than water. These physical properties make T-HA gels an ideal substrate for vitreous replacement.

Based in part on confined compression testing data reported in Example 3 above, it was possible to design a T-HA hydrogel composed of, inter alia a macromolecular network of dityramine cross-linked hyaluronan molecules, having elastic and other physical properties matched to natural vitreous material in order to produce a synthetic implantable vitreous substitute.

Choices of scaffold material (HA alone), percent tyramine substitution (~5%), protocol for tyramine substitution of HA (modified from Example 1), and exclusion of cells and bioactive factors were as described in Example 6. A concentration range of between 2.5 and 10 mg/ml of T-HA hydrogel in sterile saline most closely matched the rheologic, optical (clarity, refractive index) and gravimetric (density) properties of the vitreous of the eye. The 10 mg/ml concentration of T-HA hydrogel was deemed most appropriate based on the extensive clinical experience of our clinician collaborators. In vitro cross-linked hydrogel was used rather than an in situ cross-linking protocol based on the experience of our clinician collaborators with the potential sensitivity of the thin, highly-specialized layer of cells in the retina. In vitro cross-linking was as described in Example 1. An insoluble steroid was added to the cross-linked T-HA to allow visualization by the surgeons during the operative procedure because the hydrogel material itself was optically transparent and colorless.

Surgical Procedure

Rabbits underwent unilateral vitrectomy surgery (left eye only) using standard vitreoretinal surgical techniques with replacement of the natural vitreous of the eye with the T-HA hydrogel described above in order to evaluate the hydrogel material as a vitreous substitute. Following general anesthesia (ketamine: 50 mg/kg; xylazine: 5 mg/kg), the rabbit was prepped and draped in a sterile fashion. The left eye was dilated with mydriacyl and phenylephrine. Two drops of topical Ciloxan was instilled over the eye before and after the case. Topical proparacaine drops were instilled. Under an operating microscope, a 270° conjunctival peritomy was performed using wescott scissors. An infusion port was created 2.5 mm posterior to the limbus and the infusion cannula was secured to the sclera using 7-0 vicryl suture. A lens ring was sutured to the sclera using 7-0 vicryl suture. A 30° prism vitrectomy lens was placed on the lens ring. A second port was created and the vitrectomy instrument was inserted into the vitreous cavity. A complete core and peripheral vitrectomy was performed. At this point one of the ports was sutured closed with a 7-0 vicryl suture. The BSS bottle was lowered to patient level and ~1.2 cc of a mixture of 3 mg/ml preservative free triamcinolone acetonide (steroid) and the T-HA hydrogel (10 mg/ml, 5% tyramine substitution) in BSS was injected into the vitreous cavity through an 18 gauge syringe. The steroid is the same as usually administered after vitreoretinal surgery with its milky appearance allowing visualization of the otherwise optically transparent hydrogel material. As the milky solution was injected it was directly visualized filling the vitreous cavity. The infusion was stopped when at 50% fill or when the T-HA material was seen backing up through the irrigation canula (100% fill). After filling the vitreous cavity 7-0 vicryl suture was used to close the remaining ports. 8-0 vicryl suture was used to close the conjunctiva. Topical bacitracin ointment was placed on the eye after closing. A topical antibiotic/bacitracin ointment was applied to the eye bid×1 week, and the rabbit was placed in a recovery cage. After the rabbit had regained sternal recumbancy, it was returned to its home cage.

Post-Implantation Data

At 1 month post-implantation, rabbits were anesthetized with ketamine (50 mg/kg; 10 mg/kg/hr thereafter) and xylazine (5 mg/kg; 0.5 mg/kg/hr thereafter), the pupils dilated with eye drops (1% tropicamide; 2.5% phenylephrine), and the corneal surface anesthetized with an eye drop (0.5% proparacaine). After full pupil dilation, the status of the retina and eye were examined by indirect opthalmoscopy followed by fundus photography. In addition, intraocular pressure (IOP) was measured using a Tonopen, a device that is used clinically and which makes minimal contact with the corneal surface. Finally, the rabbit was placed on a heating pad in darkness for 1 hour, and electroretinograms (ERGs) recorded for both control and vitreous replaced eyes in response to flashes of light. ERG electrodes consist of a corneal contact lens and two platinum 0.5 inch Grass needle electrodes, placed in the cheek and trunk. While still under anesthesia, the rabbit was euthanized by using an intravenous dose of Beuthanasia D Special (1 ml/5 kg). Both control and vitreous replaced eyes were then enucleated and fixed in 10% buffered formalin for 24 hours, for histological evaluation.

Figure 10:
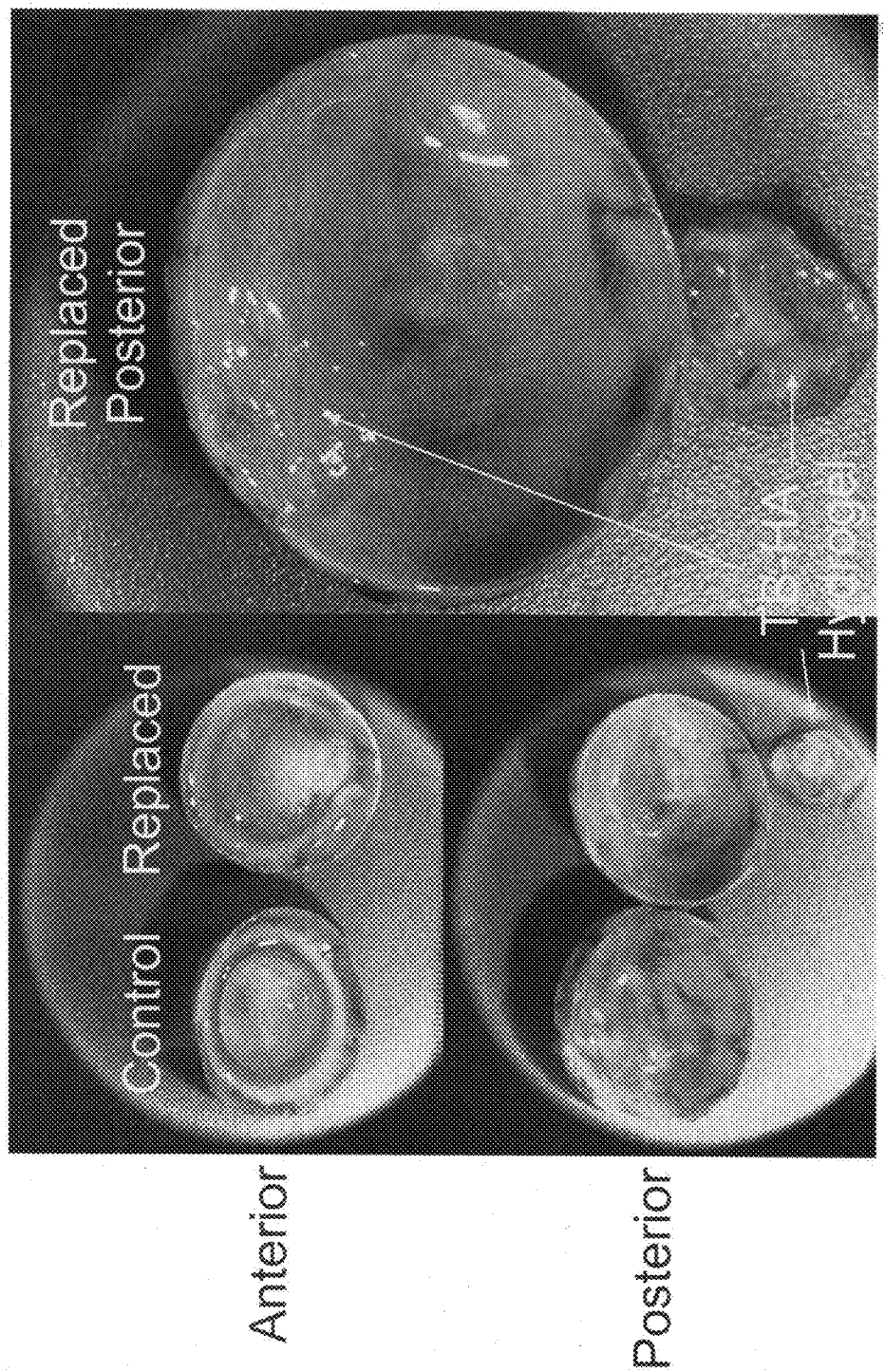
FIG. 10 is a series of photographs of control (unoperated) and experimental (surgically replaced) eyes one month post-operative, following a vitreous replacement procedure using T-HA hydrogel as a synthetic vitreous material as described in Example 8.
Figure 11:
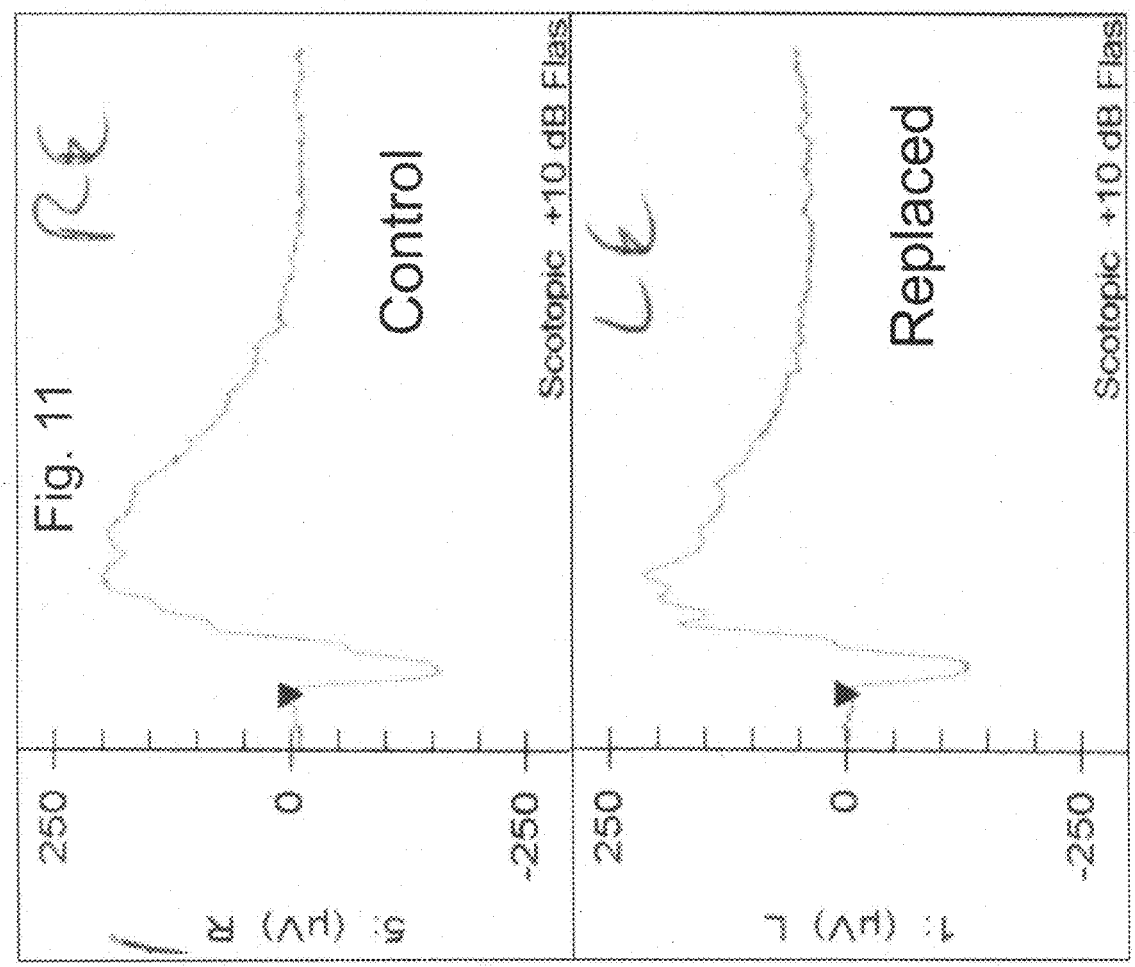
FIG. 11 shows comparative electroretinogram (ERG) results recorded for both control and vitreous replaced eyes in response to flashes of light in a rabbit model as described in Example 8.
Figure 12:
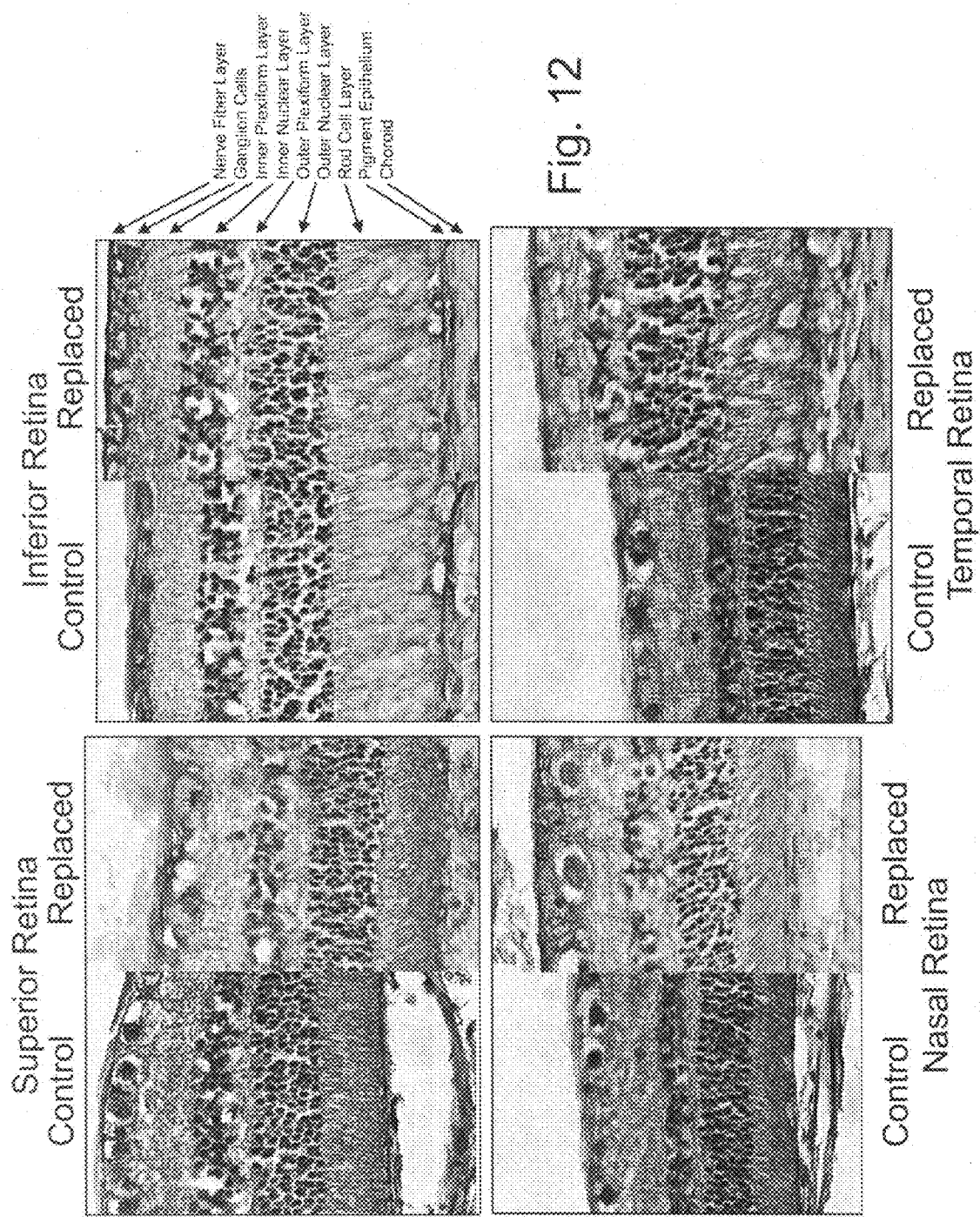
FIG. 12 is a series of electron micrographs of the retina from four quadrants of control (unoperated) and experimental (surgically replaced) eyes one month post-operative, following a vitreous replacement procedure using T-HA hydrogel as a synthetic vitreous material as described in Example 8.

The results at 1 month post-implantation, indicated minimal post-operative inflammation of the surgically treated eye with normal IOP. By one week, a cataract had formed in the vitreous replaced eye relative to the un-operated eye and to BSS control operated eyes creating a limited view of the posterior segment of the experimental eye. Gross observation of the sectioned eyes showed the cataract in the anterior segment of the vitreous replaced eye (FIG. 10). The remainder of the anterior segment as well as the entire posterior segment of the eye looked similar by gross observation (FIG. 10). Hydrogel was recovered from the experimental eye at 1 month post-implantation, and was a clear gel-like substance similar to its pre-injection form (FIG. 10). The ERG for the vitreous replaced eye was normal compared to the un-operated control eye, and indicated that the retinal cells were alive and remained functional (FIG. 11). Finally electron micrographs from the four quadrants of the retina show normal morphology for the retina from the vitreous replaced eye compared to the normal un-operated eye (FIG. 12). These data indicate the T-HA hydrogel can be used as a vitreous substitute without causing infection or inflammation of the eye, and without damaging the retina, and illustrate a method by which the T-HA hydrogel can be used as a retinal tamponade for reattachment of a detached retina.

Related Opthalmologic Applications

In addition to the foregoing retinal tamponade application following retinal reattachment surgery, the T-HA hydrogel described in this example also could be used for the following related applications:

- as a vitreous replacement for intra-operative procedures such as unfolding of retinal tears, the removal of subretinal fluid and floatation and removal of dislocated intraocular lens components.
- as a vitreous replacement incorporating a sustained release drug delivery system to maintain therapeutic drug levels (steroids, antibiotics, anti-viral drugs, etc.) in the posterior segment of the eye over long periods of time to treat chronic inflammatory and infectious conditions of the eye such as sarcoidosis, idiopathic posterior uveitis and cytomegalovirus retinitis.
- for anterior segment surgery including as a substitute for plastic polymer inserts in corneal refractive surgery. These inserts, implanted surgically in the cornea, are used to change the shape of the cornea and correct mild myopia. The optical clarity and biocompatibility of the T-HA hydrogel with human tissues make it well suited to this application.
- as a substitute for partial or full thickness corneal grafting procedures, e.g. for anterior segment surgery, necessitated as a result of corneal scarring from infection, keratinous, or other causes. The optical and physical properties of the hydrogels make them compatible with use as corneal tissue substitutes.
- as a viscoelastic device during anterior segment and cataract surgery. At low concentrations, hydrogels can maintain anterior chamber shape and pressure while allowing the surgeon to clearly visualize ocular structures.
- for oculoplastic surgery including subcutaneous injection to smooth wrinkles in the face.
- for oculoplastic surgery as an ocular implant in patients undergoing enucleation or exoneration surgery. The hydrogel formed in the dimensions of a human eye can be used as an implant to fill the orbit and improve cosmetic appearance of the individual after globe removal.
- to coat MEMS devices for use in vitreo-retinal surgery.
- to expand the utility of laser vision correction surgery (LASIK) to include those cases where volume needs to be added to the cornea rather than removed to correct vision. Corrective laser surgery would be used to produce the exact dimensions required for optimal visual outcome following implantation of an intentionally oversized plug of the hydrogel.
- as a replacement for the typical gases, perfluorocarbon liquids and silicon oils normally used as tamponades in eye surgery. These applications include but are not limited to the following: giant retinal tears, proliferative vitreoretinopathy (PVR), large breaks with "fishmouth" phenomenon, posterior breaks or macular holes, the restoration of intraocular volume after drainage of subretinal fluid, total retinal detachment with multiple breaks and large meridional folds, retinal detachment caused by ocular trauma or complicated by PVR or associated with choroidal coloboma, dislocated lenses, suprachoroidal and submacular hemorrhage, rhegmatogenous retinal detachments without PVR, severe proliferative diabetic retinopathy, chronic uveitis with profound hypotony, and infectious retinitis.

Example 9

An experiment was conducted whereby plugs of T-HA hydrogels as described hereinabove were implanted subcutaneously into immunocompetent rats in order to investigate and demonstrate their in vivo persistence and longevity as well as to measure any host immune response. As described in detail above, hydrogels comprising a cross-linked macromolecular network (such as a tyramine-substituted and cross-linked hyaluronan network) can be prepared having a range of physical and viscoelastic properties. These materials, for example, can be tuned to emulate natural soft tissue and could be used for repair or augmentation of soft tissue defects, as in plastic surgery or reconstructive surgery. In particular, as described in detail in Examples 3 and 4 above, the viscoelasticity, rigidity and other physical properties of the material can be tuned across a wide range to emulate like properties of a wide variety of native soft tissues, and the material can be cast or formed into a variety of complex anatomical shapes which would make it ideal for casting replacement or reconstructed tissue components; e.g., in the shape of an ear or of a nose for facial reconstruction.

While it already was clear from the noted examples that these materials could be cast into appropriate shapes and could be given appropriate physical properties, the present experiment demonstrates the feasibility of using the T-HA hydrogels as synthetic tissue matrix or replacement materials in vivo. Following is a description of the experiment, including the experimental methods and results obtained, after a brief discussion of the background for this application.

Background

Tissue Description and the Need for a Synthetic Material

The availability of biomaterials for soft tissue augmentation and head and neck reconstruction has remained a fundamental challenge in the field of plastic and reconstructive surgery. Significant research and investment has been undertaken for the development of a material with appropriate biological compatibility and life span. The present focus in tissue engineering has been directed at attempts toward fibroblast and chondrocyte cultures as a method of creating endogenous cartilage and collagen bearing structures useful for implantation. The archetypal standard of this avenue of research has been the nude mouse with a neo-cartilage ear on its back. This is based on the concept of chondrocyte culture on a poly-lactic or poly-glycolic acid framework. The presumption is that the chondrocytes can produce the extracellular matrix (ECM) for the production of cartilage and create a new functional biological filling agent with complete compatibility. The outcomes of this research have not been promising in regards to their clinical application. When placed in immunocompetent animals the structural integrity of the neo-cartilage has been shown to fail as the framework is absorbed. Fundamentally, while chondrocytes can successfully be cultured and propagated they apparently cannot be made to produce cartilage on a framework prior to its hydrolysis by the host defense mechanisms.

Conventionally, clinicians have been limited by the use of xenogenic materials such as bovine collagen and unmodified hyaluronan (HA) as well as synthetic materials such as silicone, silastic and hydroxyapatite. The synthetic materials are prone to foreign body reactions and infection while the biological substrates are prone to breakdown over time. In addition, synthetic PTFE (gortex) polymers and silastic offer less tissue reactivity but do not offer tissue integration and also can represent long term risks of foreign body infections and extrusion.

Instead of a tissue engineering model where chondrocytes are required to produce a cartilage ECM, the hydrogels disclosed herein are or can be based on the same materials that provide cartilage its functionality and feel (HA). In the present invention, hyaluronan is used directly as the substrate for the creation of a stable tissue engineered material to replace natural HA-rich soft tissues. In essence, the HA-based hydrogels used in herein incorporate the same material that gives cartilage its form and structural characteristics, but it is modified (tyramine-substituted and cross-linked) to make the material resistant to biological degradation. Thus, an ideal synthetic extracellular matrix material suitable for in vivo implantation and longevity is achieved.

Experimental Description

Design of Extracellular Matrix Material having Desired Properties

To provide a synthetic soft-tissue and cartilage substitute for use in head and neck reconstruction based on the disclosed HA materials the following points were considered: 1) optimization of enzyme-selective cross-linked hydrogels using hyaluronan as the scaffold material; and 2) application of T-HA hydrogels as cartilage substitutes and soft-tissue fillers. These include characterization of the effect of the cross-linked hydrogels in vivo.

Again, based in part on confined compression testing data reported in Example 3 above, it was possible to design T-HA hydrogels composed of, inter alia a macromolecular network of dityramine cross-linked hyaluronan molecules, having elastic and other physical properties matched to natural soft tissues which were suitable for in, vivo rat implantation to determine their immunogenic and longevity characteristics.

Choices of scaffold material (HA alone), percent tyramine substitution (~5%), protocol for tyramine substitution of HA (modified from Example 1), and exclusion of cells and bioactive factors were as described in Example 6. A concentration range of between 6.25 and 100 mg/ml of T-HA hydrogel encompassed the wide spectrum of physical properties required of a material for facial reconstruction. Therefore the same five concentration used in Example 3 were deemed appropriate for testing in a subcutaneous rat model based on the extensive clinical experience of our clinician collaborators. In vitro cross-linked hydrogels were used so as to produce hydrogels of defined shape for analysis of shape retention, a property deemed important by our clinician collaborators. In vitro cross-linking was as described in Example 1.

Surgical Procedure

T-HA hydrogel plugs of defined shape, mass and volume (7 mm in diameter and 3 mm in thickness) and defined mechanical properties based on HA concentration were surgically implanted subcutaneously in the backs of immunocompetent rats to allow evaluation of their in vivo persistence and host immune response based on previously published protocols for the evaluation of collagen and other HA-based hydrogels. After induction of anesthesia with intraperitoneal injection of ketamine (100 mg/kg) and xylazine (5 mg/kg), the rat received a single intramuscular injection of 60,000 units of procaine penicillin for infection prophylaxis. A 1 cm stab incision was made with a #11 surgical blade in the lower lumbar region of the rat. A 14 g needle was used as a trocar to dissect in the subcutaneous plane to create a pocket. Three preformed hydrogel plugs (~7.1 mm diameter×3 mm thick) of one of the HA concentrations to be tested were inserted into the surgical pocket. A single absorbable stitch (3-0 Chromic) was placed to re-approximate the skin edge. At 1 week, 1 month, 3 months, and 6 months post-implantation, rats were sacrificed by $CO_2$ asphyxiation and the T-HA hydrogel plugs with surrounding tissue excised and stored in formalin at 4° C. until time for histological evaluation.

Post-Implantation Data

Hydrogel compositions tested included plugs made from concentrations of 6.25, 12.5, 25, 50, and 100 mg/ml of HA, generating hydrogel plugs with a wide spectrum of physical properties ranging from that of gel to a paste to a rubber-like material (see Example 3). Implanted T-HA hydrogel plugs were collected at 1 week, 1 month, 3 months, and 6 months post-implantation. Excised plugs were evaluated for their in vivo persistence and host immune response.

Figure 13:
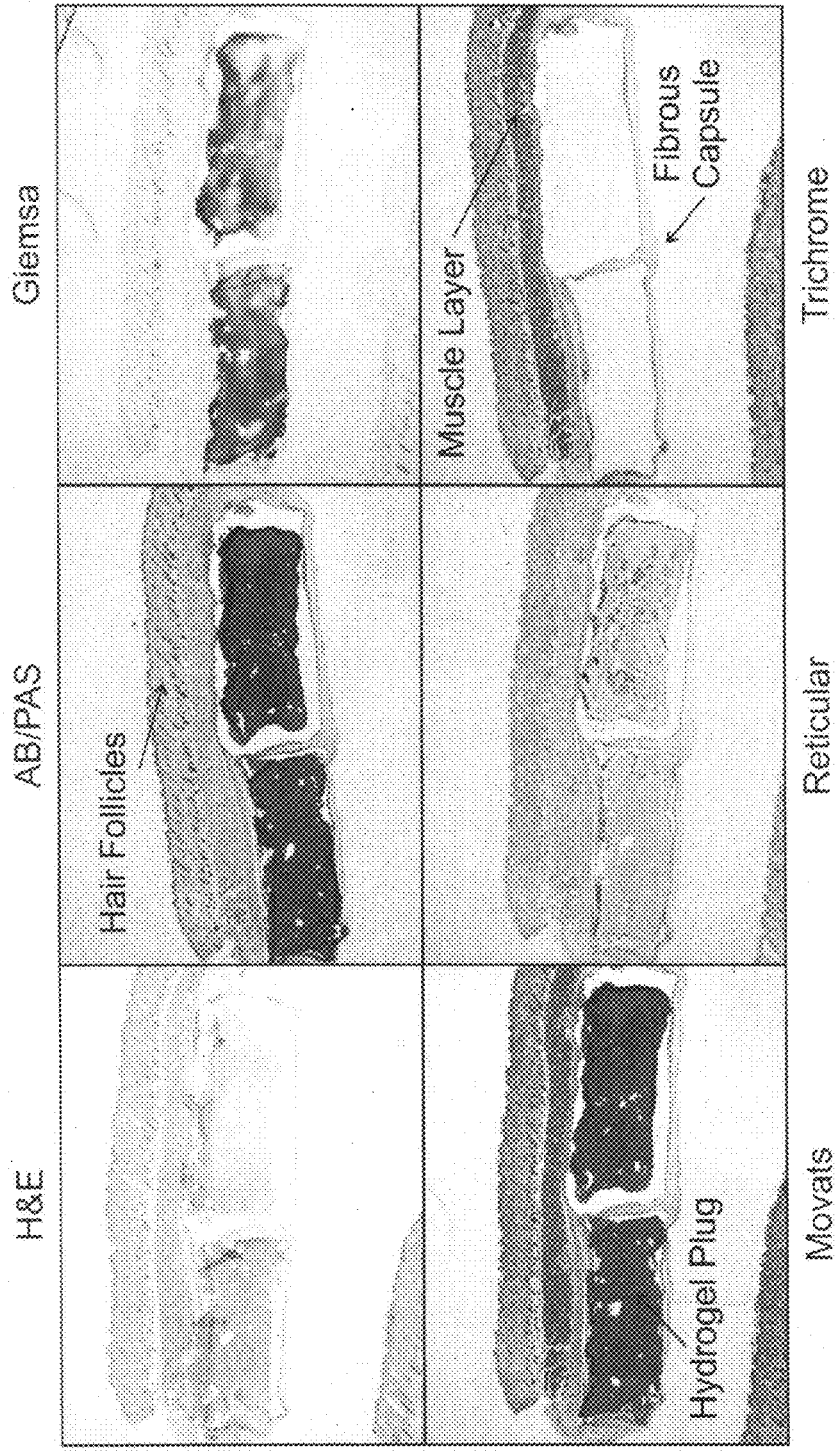
FIG. 13 is a series of photographs showing representative results of histological results for a 100 mg/ml T-HA hydrogel plug implanted subcutaneously into an immunocompetent rat at one month post-operatively as described in Example 9.

FIG. 13 shows representative results of histological staining with H&E, alcian blue, MC/giemsa, Movats, Reticular, and Trichrome stains for the 100 mg/ml TB-HA hydrogel plug from the 1-month time point. Clearly defined in FIG. 13 are the surface hair follicles, the superficial muscle layer, the hydrogel plug, and the thin fibrous capsule surrounding the hydrogel plug as a result of a minimal foreign body response. An artifact exists as a result of hydrogel shrinkage from the paraffin embedding process, which can be avoided through the use of frozen sections. The results show very little immune response with only a thin layer of mast cells surrounding the plug, and no evidence for host cell infiltration into the plug. When measured, the volume of the void left by the plug during histological processing is 3 mm (the original plug thickness) indicating little to no biodegradation or deformation of the hydrogel matrix. Staining indicated that the plugs had little protein, such as collagen or elastin, deposited within them and remained primarily composed of HA hydrogel. These results indicate that the hydrogel plugs over a broad range of five concentrations persisted through 6 months with little evidence of degradation, host immune response, and cellular infiltration providing a wide range of injectable materials for use in soft tissue reconstruction.

Example 10

It will be apparent from the foregoing discussion and the Examples that hydrogels described herein composed of a cross-linked (in situ or ex vivo) macromolecular network of hyaluronan molecules cross-linked via a suitable dihydroxyphenyl cross-linking chemistry as herein described are suitable as a synthetic, implantable extracellular matrix tissue material for a variety of tissue engineering and repair applications. A particular such application for which the disclosed hydrogel materials will have particular utility is in the repair or augmentation of the mitral valve in a heart.

The mitral valve is one of the most complex connective tissue structures in the body. It consists of two leaflets and numerous chordae tendineae. These chordae have a highly aligned collagenous core and a thin outer sheath of elastic fibers and endothelial cells. Both leaflets are laminated tissues containing a heavily collagenous layer on the ventricular side, a predominantly elastic layer on the atrial side, and an inner spongiosa layer containing abundant proteoglycans (PGs) and hyaluronan (HA). The relative thicknesses of these layers vary between the two leaflets and also within each leaflet from its attachment edge to its free edge.

The variability of the different leaflet layers, and hence the structural constituents within the mitral valve, are determined by the specific functional roles of the leaflets and chordae.

The closed valve maintains a balance of tensile and compressive loads, in which the chordae and the flat central region of the anterior leaflet are in tension, whereas the free edge of the anterior leaflet and most of the posterior leaflet are in appositional compression. Accordingly, the most collagenous components of the mitral apparatus are the chordae and the portion of the anterior leaflet between the annulus and the upper appositional border. In the posterior leaflet and in the free edge of the anterior leaflet, the collagenenous layer is relatively thinner, whereas the PG rich spongiosa is substantially thicker. The wide diversity of glycosaminoglycans (GAGs) and their parent PGs exert considerable yet variable control over the physical properties of the extracellular matrix.

Functional mitral regurgitation (MR) refers to the regurgitation that occurs with a structurally normal valve as a consequence of left ventricular (LV) dysfunction, and as a result, almost half the patients with LV dysfunction have at least moderate MR. Functional MR plays a pivotal role in the pathophysiology of congestive heart failure (CHF), a major cause of cardiac morbidity and mortality. Several studies have shown that the presence of functional MR in patients with CHF is associated with poor outcomes. Although this observation could suggest that MR is merely an indicator of CHF severity, it is also increasingly apparent that the development of the MR hastens the progression of CHF. The precise mechanism of functional MR remains controversial and can relate to mitral annular dilatation in the septal-lateral (S-L) axis or tethering of the leaflets secondary to progressive ventricular remodeling. MR leads to greater volume overload of the LV with progressive annular dilatation and increased MR, creating a "vicious cycle" which exacerbates the problem. MR is commonly considered to be one of the initiators of CHF, as well as an ongoing impetus of the progression of the disease.

Surgical annuloplasty is a widely used method for mitral valve repair and can provide long-term benefit. However, the surgical procedure requires access to and manipulation of the valve annulus via atriotomy. In addition, the procedure requires the patient to be placed on cardiopulmonary bypass (CPB). The prolonged CPB time has been suggested as a cause of not only postoperative LV dysfunction but also main organ dysfunction. The use of heparin during CPB results in an increased risk of bleeding complications. The increased morbidity and mortality profile leads many care providers directly to non-treatment options of MR in the earlier stage heart failure patients.

Recently, several minimally invasive methods of mitral valve repair have been developed. For example, several investigators have reported the preliminary methodology of off-pump mitral valve repair procedures through a thoracic incision. Others have reported new devices that can be inserted percutaneously into the coronary sinus and great cardiac vein to reduce the S-L dimension of the mitral annulus. There are the possibilities of adverse effects, however, such as obstruction or disturbance of the coronary circulation, by chronic placement of the device in the coronary sinus.

Surgical therapy for functional MR, including mitral valve repair with an annuloplasty ring and replacement with an artificial valve has been limited in patients with severe CHF by relatively high operative mortality rates due to the effects of CPB. Therefore, there is a need for a minimally invasive procedure that will not compromise coronary circulation and will allow for reduction of the S-L dimension of the mitral annulus to reduce functional MR as well as other forms of MR. Myxomatous changes in mitral valve tissues can lead to leaflet prolapse and mitral regurgitation.

The T-HA hydrogel materials disclosed herein could be adapted for this purpose; i.e. mitral annular remodeling resulting from a nonabsorbable substance injection (namely a T-HA hydrogel material designed to have the necessary viscoelastic and other physical properties) into the posterior mitral annulus using an epicardial approach. This procedure would enable the S-L dimension to be efficiently reduced, thus reducing MR, without employing CPB or implanting a device into the coronary sinus. This mitral annular remodeling procedure could be modified to allow for percutaneously injection of the substance through the coronary sinus.

This application for a T-HA hydrogel as disclosed herein would enable a nonabsorbable substance to be percutaneously injected through the coronary sinus for severe CHF patients with functional MR who are unable to receive conventional mitral valve surgery. This minimally invasive approach would obviate the need for CPB and sternotomy, as well as diminish the risk of major side effects from conventional surgical therapy such as postoperative LV dysfunction and resulting poor organ perfusion. In addition, such a procedure would provide patients with mild to moderate CHF with an option for early restoration of mitral valve competence, arresting the initiation and progression of devastating heart failure.

In particular, a hydrogel composed of a cross-linked macromolecular network as described herein, particularly of HA, could be designed based on the principles as elucidated in Example 3 above, in order to produce a hydrogel material having all of the following characteristics which would be considered desirable for this application:

Injectable and nonabsorbable;
Low-grade inflammatory reaction;
Low evidence of foreign body migration;
Ease of collagen encapsulation which contributes to the prevention of migration;
Not especially malleable nor especially rigid.

A protocol has been established for the injection of a T-HA hydrogel material to augment the mitral valve of a beating heart. That protocol is described as follows.

Injection Procedure—Two dimensional epicardial echocardiography (2D EE) and transesophageal echocardiography (2D TEE) are performed to evaluate LV end-diastolic and end-systolic volumes (EDV and ESV), stroke volume (SV), ejection fraction (EF), the S-L dimension of mitral annulus, and the degree of MR. Hemodynamic data such as LVP, LAP, the central venous pressure (CVP), the pulmonary arterial pressure (PAP), the pulmonary capillary wedge pressure (PCWP), CO, LAD flow, and LCX flow should be collected. LV end-diastolic and end-systolic pressure-volume relations can be obtained by transient IVC occlusion using an occlusion catheter to assess LV contractility and compliance (baseline before injection).

A commercially available cardiac stabilizer used for off-pump coronary bypass grafting can be used to stabilize the target region. Under 2D TEE guidance, the uncross-linked T-HA hydrogel composition (50 mg/ml in sterile saline) is injected into the posterior mitral annulus from the outside of the heart while the heart is beating. During the injection, 2D can be used to assess the position of the tip of the needle for the injection, the range occupied by the substance in the posterior annulus. Once an appropriate fill and repositioning of the mitral valve has been accomplished, cross-linking is initiated by injection of 0.2 cc of 0.6% hydrogen peroxide. After completion of cross-linking of the hydrogel implant, data including hemodynamics, coronary flow, LV pressure-volume loops (LV P-V loops), 2D EE, and 2D TEE should be collected (data after injection).

The foregoing injection methodology was developed and evaluated using cadaveric dog and pig hearts as models. FIG. 14 shows a cadaveric dog heart in which a T-HA hydrogel material was injected and cross-linked in situ via the foregoing injection methodology. To produce the T-HA hydrogel material for this experiment, the scaffold material (HA alone), percent tyramine substitution (~5%), protocol for tyramine substitution of HA (modified from Example 1) and non-inclusion of cells and bioactive factors were as described in Example 6. Concentrations of 25, 50 and 100 mg/ml of T-HA hydrogel in saline most closely matched those of cardiac (heart) tissue required for mitral valve closure. The 50 mg/ml T-HA hydrogel was deemed most appropriate for a mitral annular remodeling procedure by percutaneously injection based on the extensive clinical experience of our clinician collaborators. Peroxidase would be added at 10 U/ml prior to application in an in situ cross-linking protocol as the one described below. The in situ cross-linking protocol is preferred as it would allow the uncross-linked T-HA to pass through an appropriately sized needle while the cross-linked hydrogel may not. In addition, the in situ cross-linking protocol allows the surgeon first to properly position (close) the mitral valves by injection of the uncross-linked hydrogel and then cross-link the hydrogel into a solid implant only after visual confirmation that the mitral valve had been properly repositioned.

In FIG. 14, the implanted hydrogel was bisected post-implantation to demonstrate its solid, viscoelastic character following in situ cross-linking, as well as to evaluate its placement in the heart. In particular, these models were used to 1) evaluate the appropriate concentration of hydrogel required to both mimic the consistency of cardiac muscle after cross-linking yet pass through the injection port prior to cross-linking; 2) demonstrate reproducibility for the in vivo cross-linking protocols for complete cross-linking in vivo at the required volumes (~2 ml); and development suitable injection techniques. All of these goals were met, establishing confidence that the injection procedure as well as a suitable T-HA hydrogel can precisely accommodate anatomical constraint on the mitral annulus.

Although the above-described embodiments constitute the preferred embodiments, it will be understood that various changes or modifications can be made thereto without departing from the spirit and the scope of the present invention as set forth in the appended claims.

What is claimed is:

1. A synthetic macromolecular network comprising macromolecules selected from the group consisting of a) polycarboxylate molecules that have been substituted at $CO_2H$ sites thereon with a hydroxyphenyl compound at a substitution rate less than 10 percent based on a total number of $CO_2H$ sites on the polycarboxylate molecules, b) polyamines that have been substituted at primary amine sites thereon with a hydroxyphenyl compound, and c) copolymers thereof; and at least one dihydroxyphenyl linkage linking different macromolecules or linking different sites on the same macromolecule.

2. A synthetic macromolecular network according to claim 1, all said macromolecules being of the same kind.

3. A synthetic macromolecular network according to claim 1, said macromolecules being polycarboxylates.

4. A synthetic macromolecular network according to claim 1, said macromolecules being polyamines.

5. A synthetic macromolecular network according to claim 1, said macromolecules being hyaluronan.

6. A synthetic macromolecular network according to claim 1, said macromolecules comprising molecules selected from the group consisting of peptides and proteins.

7. A synthetic macromolecular network according to claim 1, further comprising a population of viable living cells within said macromolecular network.

8. A synthetic macromolecular network according to claim 1, further comprising bioactive factors within said macromolecular network.

9. A synthetic macromolecular network according to claim 1, said macromolecules comprising peptides and/or proteins as said polycarboxylate molecules, wherein at least one dihydroxyphenyl linkage is formed between two hydroxyphenyl groups attached respectively to adjacent peptides and/or proteins.

10. A synthetic macromolecular network according to claim 1, said hydroxyphenyl compound being tyramine or tyrosine.

11. A synthetic macromolecular network according to claim 1, said macromulecules comprising polycarboxylate molecules having a hydroxyphenyl compound substitution rate less than 9 percent based on the total number of $CO_2H$ sites present on said polycarboxylate molecules.

12. A synthetic macromolecular network according to claim 1, said macromolecules comprising polycarboxylate molecules having a hydroxyphenyl compound substitution rate less than 6 percent based on the total number of $CO_2H$ sites present on said polycarboxylate molecules.

13. A synthetic macromolecular network according to claim 1, said macromolecules comprising a plurality of tyramine-substituted hyaluronan molecules, at least two adjacent hyaluronan molecules being linked by a dityramine linkage.

14. A synthetic macromolecular network according to claim 13, having a tyramine substitution rate on said hyaluronan molecules of less than 50% based on the total number of $CO_2H$ sites present on said hyaluronan molecules.

15. A synthetic macromolecular network according to claim 13, having a tyramine substitution rate on said hyaluronan molecules of less than 10% based on the total number of $CO_2H$ sites present on said hyaluronan molecules.

16. A synthetic macromolecular network according to claim 13, having a tyramine substitution rate on said hyaluronan molecules of about or less than 5% based on the total number of $CO_2H$ sites present on said hyaluronan molecules.

17. A synthetic, implantable cartilage material comprising the synthetic macromolecular network according to claim 13.

18. A synthetic, implantable vocal cord material comprising the synthetic macromolecular network according to claim 13.

19. A synthetic, implantable vitreous material comprising the synthetic macromolecular network according to claim 13.

20. A synthetic, implantable soft tissue material comprising the synthetic macromolecular network according to claim 13.

21. A synthetic macromolecular network according to claim 13, further comprising a population of viable living cells within said macromolecular network.

22. A synthetic macromolecular network according to claim 13, further comprising bioactive factors within said macromolecular network.

23. A hydrogel comprising the synthetic macromolecular network according to claim 13.

24. A synthetic, implantable cartilage material comprising the synthetic macromolecular network according to claim 1.

25. A synthetic, implantable vocal cord material comprising the synthetic macromolecular network according to claim 1.

26. A synthetic, implantable vitreous material comprising the synthetic macromolecular network according to claim 1.

27. A synthetic, implantable soft tissue material comprising the synthetic macromolecular network according to claim 1.

28. A macromolecular network comprising a plurality of hydroxyphenyl-substituted hyaluronan molecules linked by dihydroxyphenyl linkages and containing a population of viable living cells within the macromolecular network.

29. The macromolecular network of claim 28, wherein the living cells include cells selected from the group consisting of chondrocytes, progenitor cells, and stem cells.

30. The macromolecular network of claim 28, further comprising one or more bioactive factors.

31. The macromolecular network of claim 30, wherein the bioactive factors include bioactive factors selected from the group consisting of growth factors, hormones, and factors controlling cell differentiation.

32. The macromolecular network of claim 28, wherein the macromolecular network is a hydrogel.

33. The macromolecular network of claim 28, wherein the degree of hydroxyphenyl substitution is less than 20% based on the total quantity of carboxyl groups present in the hyaluronan molecules.

34. The macromolecular network of claim 28, wherein the degree of hydroxyphenyl substitution is less than 10% based on the total quantity of carboxyl groups present in the hyaluronan molecules.

35. The macromolecular network of claim 28, wherein the degree of hydroxyphenyl substitution is between 1.7% and 4.7% based on the total quantity of carboxyl groups present in the hyaluronan molecules.

36. The macromolecular network of claim 28, wherein the degree of hydroxyphenyl substitution is between 4% and 6% based on the total quantity of carboxyl groups present in the hyaluronan molecules.

37. The macromolecular network of claim 28, wherein the hydroxyphenyl substituted onto hyaluronan molecules comprises tyramine.

38. The macromolecular network of claim 28, wherein the rigidity, rheology and texture of the network are jelly-like.

39. The macromolecular network of claim 28, wherein the rigidity, rheology and texture of the network are gelatin-like.

40. The macromolecular network of claim 28, wherein the rigidity, rheology and texture of the network are dough-like.

41. The macromolecular network of claim 28, wherein the rigidity, rheology and texture of the network are that of a resilient rubber-like composition.

42. The macromolecular network of claim 28, wherein the rigidity, rheology and texture of the network are that of a cartilage-like material.

43. A hydrogel comprising a macromolecular network comprising a plurality of tyramine-substituted hyaluronan molecules linked by dityramine linkages and containing a population of viable living cells within the macromolecular network, wherein the degree of tyramine substitution is less than 10% based on the total quantity of carboxyl groups present in the hyaluronan molecules.

44. The macromolecular network of claim 43, wherein the living cells include cells selected from the group consisting of chondrocytes, progenitor cells, and stem cells.

45. The macromolecular network of claim 43, further comprising one or more bioactive factors.

46. The macromolecular network of claim 45, wherein the bioactive factors include bioactive factors selected from the group consisting of growth factors, hormones, and factors controlling cell differentiation.

47. The macromolecular network of claim 43, wherein the degree of hydroxyphenyl substitution is between 1.7% and 4.7% based on the total quantity of carboxyl groups present in the hyaluronan molecules.

48. The macromolecular network of claim 43, wherein the degree of hydroxyphenyl substitution is between 4% and 6% based on the total quantity of carboxyl groups present in the hyaluronan molecules.

* * * * *